(12) United States Patent
Hennequin

(10) Patent No.: US 7,371,765 B2
(45) Date of Patent: May 13, 2008

(54) QUINOLINE DERIVATIVES HAVING VEGF INHIBITING ACTIVITY

(75) Inventor: Laurent Francois Andre Hennequin, Alderley Park (GB)

(73) Assignee: AstraZeneca AB, Sodertalje (SE)

( * ) Notice: Subject to any disclaimer, the term of this patent is extended or adjusted under 35 U.S.C. 154(b) by 471 days.

(21) Appl. No.: 10/332,274

(22) PCT Filed: Aug. 8, 2001

(86) PCT No.: PCT/GB01/03553

§ 371 (c)(1),
(2), (4) Date: Jan. 7, 2003

(87) PCT Pub. No.: WO02/12226

PCT Pub. Date: Feb. 14, 2002

(65) Prior Publication Data

US 2003/0199491 A1    Oct. 23, 2003

(30) Foreign Application Priority Data

Aug. 9, 2000    (EP) .................................. 00402254

(51) Int. Cl.
| A61K 31/47 | (2006.01) |
| A61K 31/54 | (2006.01) |
| A61K 31/497 | (2006.01) |
| A01N 43/42 | (2006.01) |
| C07D 215/00 | (2006.01) |
| C07D 215/38 | (2006.01) |
| C07D 279/10 | (2006.01) |
| C07D 279/12 | (2006.01) |
| C07D 401/00 | (2006.01) |
| C07D 295/00 | (2006.01) |

(52) U.S. Cl. ...................... 514/312; 514/313; 514/314; 514/228.2; 514/253.06; 544/58.2; 544/363; 546/153; 546/159

(58) Field of Classification Search ........... 514/252.06, 514/706, 186; 544/128
See application file for complete search history.

(56) References Cited

U.S. PATENT DOCUMENTS

| 3,755,332 A | 8/1973 | Wasley et al. |
| 5,409,930 A | 4/1995 | Spada et al. |
| 5,480,883 A | 1/1996 | Spada et al. |
| 5,646,153 A | 7/1997 | Spada et al. |
| RE36,256 E | 7/1999 | Spada et al. |
| 6,002,008 A | 12/1999 | Wissner et al. |
| 6,162,804 A | 12/2000 | Bilodeau et al. |

FOREIGN PATENT DOCUMENTS

| EP | 0326330 B1 | 8/1989 |
| EP | 0 860 433 A1 | 8/1998 |
| EP | 860433 A1 * | 8/1998 |
| EP | 1029853 A1 | 8/2000 |
| GB | 2 345 486 A | 7/2000 |
| WO | 87/04321 | 7/1987 |
| WO | 92/20642 | 11/1992 |
| WO | 96/30370 | 10/1996 |
| WO | 97/03069 | 1/1997 |
| WO | 97/17329 | 5/1997 |
| WO | 98/02434 | 1/1998 |
| WO | 98/13350 A | 4/1998 |
| WO | 98/14431 | 4/1998 |
| WO | WO 98/13350 * | 4/1998 |
| WO | WO9813350 A1 * | 4/1998 |
| WO | 98/54093 | 12/1998 |
| WO | 99/21859 | 5/1999 |
| WO | 99/35132 | 7/1999 |
| WO | 99/35146 | 7/1999 |
| WO | 00/12497 | 3/2000 |
| WO | 00/18761 | 4/2000 |
| WO | 00/44728 | 8/2000 |
| WO | 01/02369 | 1/2001 |

* cited by examiner

Primary Examiner—James O. Wilson
Assistant Examiner—Erich A. Leeser
(74) Attorney, Agent, or Firm—Morgan, Lewis & Bockius LLP

(57) ABSTRACT

The invention relates to compounds of formula (I) wherein: either any one of $G_1$, $G_2$, $G_3$, $G_4$ and $G_5$ is nitrogen and the other four are —CH—, or $G_1$, $G_2$, $G_3$, $G_4$ and $G_5$ are all —CH—; Z is —O—, —NH—, —S—, —CH$_2$— or a direct bond; Z is linked to any one of $G_1$, $G_2$, $G_3$ and $G_4$; n is an integer from 0 to 5; m is an integer from 0 to 3; $R^a$ represents hydrogen or fluoro; $R^b$, $R^1$ and $R^2$ are defined herein and salt thereof, process for the preparation so such compounds, pharmaceutical compositions containing a compound of formula I or a pharmaceutically acceptable salt thereof as active ingredient and the use of a compound of formula I in the manufacture of a medicament for the production of an antiangiogenic and/or vascular permeability reducing effect in warm-blooded animals. The compounds of formula I and the pharmaceutically acceptable salts thereof inhibit the effects of VEGF, a property of value in the treatment of a number of diseases states including cancer and rheumatoid arthritis.

15 Claims, No Drawings

QUINOLINE DERIVATIVES HAVING VEGF INHIBITING ACTIVITY

The present invention relates to quinoline derivatives, processes for their preparation, pharmaceutical compositions containing them as active ingredient, methods for the treatment of disease states associated with angiogenesis and/or increased vascular permeability, to their use as medicaments and to their use in the manufacture of medicaments for use in the production of antiangiogenic and/or vascular permeability reducing effects in warm-blooded animals such as humans.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57–66; Folkman, 1995, Nature Medicine 1: 27–31). Alteration of vascular permeability is thought to play a role in both normal and pathological physiological processes (Cullinan-Bove et al, 1993, Endocrinology 133: 829–837; Senger et al, 1993, Cancer and Metastasis Reviews, 12: 303–324). Several polypeptides with in vitro endothelial cell growth promoting activity have been identified including, acidic and basic fibroblast growth factors (aFGF & bFGF) and vascular endothelial growth factor (VEGF). By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848–859; Kolch et al, 1995, Breast Cancer Research and Treatment, 36:139–155) and vascular permeability (Connolly et al, 1989, J. Biol. Chem. 264: 20017–20024). Antagonism of VEGF action by sequestration of VEGF with antibody can result in inhibition of tumour growth (Kim et al, 1993, Nature 362: 841–844). Basic FGF (bFGF) is a potent stimulator of angiogenesis (e.g. Hayek et al, 1987, Biochem. Biophys. Res. Commun. 147: 876–880) and raised levels of FGFs have been found in the serum (Fujimoto et al, 1991, Biochem. Biophys. Res. Commun. 180: 386–392) and urine (Nguyen et al, 1993, J. Natl. Cancer. Inst. 85: 241–242) of patients with cancer.

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity which leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt or Flt1, the kinase insert domain-containing receptor, KDR (also referred to as Flk-1), and another fms-like tyrosine kinase receptor, Flt4. Two of these related RTKs, Flt and KDR, have been shown to bind VEGF with high affinity (De Vries et al, 1992, Science 255: 989–991; Terman et al, 1992, Biochem. Biophys. Res. Comm. 1992, 187: 1579–1586). Binding of VEGF to these receptors expressed in heterologous cells has been associated with changes in the tyrosine phosphorylation status of cellular proteins and calcium fluxes.

The present invention is based on the discovery of compounds that surprisingly inhibit the effects of VEGF, a property of value in the treatment of disease states associated with angiogenesis and/or increased vascular permeability such as cancer, diabetes, psoriasis, rheumatoid arthritis, Kaposi's sarcoma, haemangioma, acute and chronic nephropathies, atheroma, arterial restenosis, autoimmune diseases, acute inflammation, excessive scar formation and adhesions, lymphoedema, endometriosis, dysfunctional uterine bleeding and ocular diseases with retinal vessel proliferation. Compounds of the present invention generally possess higher potency against VEGF receptor tyrosine kinase than against epidermal growth factor (EGF) receptor tyrosine kinase. Compounds of the invention which have been tested possess activity against VEGF receptor tyrosine kinase such that they may be used in an amount sufficient to inhibit VEGF receptor tyrosine kinase whilst demonstrating no significant activity against EGF receptor tyrosine kinase. As well as possessing activity against VEGF receptor tyrosine kinase, compounds of the present invention possess activity against FGF R1 receptor tyrosine kinase.

According to one aspect of the present invention there is provided the use of a compound of the formula I:

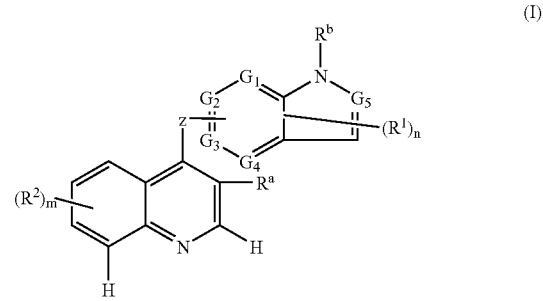

(I)

wherein:
either any one of $G_1$, $G_2$, $G_3$, $G_4$ and $G_5$ is nitrogen and the other four are —CH—, or $G_1$, $G_2$, $G_3$, $G_4$ and $G_5$ are all —CH—;

Z is —O—, —NH—, —S—, —CH$_2$— or a direct bond; Z is linked to any one of $G_1$, $G_2$, $G_3$ and $G_4$ which is a free carbon atom;

n is an integer from 0 to 5; any of the substituents $R^1$ may be attached at any free carbon atom of the indole, azaindole or indazole group, such free carbon atoms may be $G_1$, $G_2$, $G_3$, $G_4$ or $G_5$ or may be at the 3-position of the indole, azaindole or indazole group;

m is an integer from 0 to 3;

$R^a$ represents hydrogen or fluoro;

$R^b$ represents hydrogen, $C_{1-4}$alkyl, $C_{1-4}$alkoxyC$_{1-4}$alkyl, aminoC$_{1-4}$alkyl, C$_{1-3}$alkylaminoC$_{1-4}$alkyl, di(C$_{1-3}$alkyl)aminoC$_{1-4}$alkyl, C$_{2-5}$alkynylaminoC$_{1-4}$alkyl, C$_{2-5}$alkynylaminoC$_{1-4}$alkyl, —C$_{1-5}$alkyl(ring A) wherein ring A is selected from azetidinyl, pyrrolidinyl, piperidinyl, piperazinyl, morpholino and thiomorpholino and wherein ring A may bear one or more substituents selected from C$_{1-4}$alkyl, C$_{2-5}$alkenyl, C$_{2-5}$alkynyl, hydroxy, oxo, halogeno, cyano, cyanoC$_{1-4}$alkyl, C$_{1-4}$alkylsulphonyl and C$_{1-4}$alkanoyl;

$R^1$ represents hydrogen, oxo, hydroxy, halogeno, C$_{1-4}$alkyl, C$_{1-4}$alkoxy, C$_{1-4}$alkoxyC$_{1-4}$alkyl, aminoC$_{1-4}$alkyl, $C_{1-3}$alkylamino$C_{1-4}$alkyl, di($C_{1-3}$alkyl)amino$C_{1-4}$alkyl, -$C_{1-5}$alkyl(ring B) wherein ring B is selected from azetidinyl, pyrrolidinyl, piperidinyl, piperazinyl, N-methylpiperazinyl, N-ethylpiperazinyl, morpholino and thiomorpholino;

$R^2$ represents hydrogen, hydroxy, halogeno, cyano, nitro, trifluoromethyl, $C_{1-3}$alkyl, $C_{1-3}$alkoxy, $C_{1-3}$alkylsulphanyl, —$NR^3R^4$ (wherein $R^3$ and $R^4$, which may be the same or different, each represents hydrogen or $C_{1-3}$alkyl), or $R^5X^1$— (wherein $X^1$ represents a direct bond, —O—, —$CH_2$—, —OC(O)—, —C(O)—, —S—, —SO—, —$SO_2$—, —$NR^6$C(O)—, —C(O)$NR^7$—, —$SO_2NR^8$—, —$NR^9SO_2$— or —$NR^{10}$— (wherein $R^6$, $R^7$, $R^8$, $R^9$ and $R^{10}$ each independently represents hydrogen, $C_{1-3}$alkyl or $C_{1-3}$alkoxy$C_{2-3}$alkyl), and $R^5$ is selected from one of the following twenty-two groups:

1) hydrogen, oxiranyl$C_{1-4}$alkyl or $C_{1-5}$alkyl which may be unsubstituted or which may be substituted with one or more groups selected from hydroxy, fluoro, chloro, bromo and amino;

2) $C_{1-5}$alkyl$X^2$C(O)$R^{11}$ (wherein $X^2$ represents —O— or —$NR^{12}$— (in which $R^{12}$ represents hydrogen, $C_{1-3}$alkyl or $C_{1-3}$alkoxy$C_{2-3}$alkyl) and $R^{11}$ represents $C_{1-3}$alkyl, —$NR^{13}R^{14}$ or —$OR^{15}$ (wherein $R^{13}$, $R^{14}$ and $R^{15}$ which may be the same or different each represents hydrogen, $C_{1-5}$alkyl or $C_{1-3}$alkoxy$C_{2-3}$alkyl));

3) $C_{1-5}$alkyl$X^3R^{16}$ (wherein $X^3$ represents —O—, —S—, —SO—, —$SO_2$—, —OC(O)—, —$NR^{17}$C(O)—, —C(O)$NR^{18}$—, —$SO_2NR^{19}$—, —$NR^{20}SO_2$— or —$NR^{21}$— (wherein $R^{17}$, $R^{18}$, $R^{19}$, $R^{20}$ and $R^{21}$ each independently represents hydrogen, $C_{1-3}$alkyl or $C_{1-3}$alkoxy$C_{2-3}$alkyl) and $R^{16}$ represents hydrogen, $C_{1-3}$alkyl, cyclopentyl, cyclohexyl or a 4-, 5- or 6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ring D (wherein f is 0 or or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl));

4) $C_{1-5}$alkyl$X^4C_{1-5}$alkyl$X^5R^{22}$ (wherein $X^4$ and $X^5$ which may be the same or different are each —O—, —S—, —S—, —$SO_2$—, —$NR^{23}$C(O)—, —C(O)$NR^{24}$—, —$SO_2NR^{25}$—, $NR^{26}SO_2$— or —$NR^{27}$— (wherein $R^{23}$, $R^{24}$, $R^{25}$, $R^{26}$ and $R^{27}$ each independently represents hydrogen, $C_{1-3}$alkyl or $C_{1-3}$alkoxy$C_{2-3}$alkyl) and $R^{22}$ represents hydrogen, $C_{1-3}$alkyl or $C_{1-3}$alkoxy$C_{2-3}$alkyl);

5) $R^{28}$ (wherein $R^{28}$ is a 4-, 5- or 6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkanoyl, $C_{1-4}$alkoxy$C_{1-4}$alkyl, $C_{1-4}$alkylsulphonyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$akyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl));

6) $C_{1-5}$alkyl$R^{28}$ (wherein $R^{28}$ is as defined hereinbefore);

7) $C_{2-5}$alkenyl$R^{28}$ (wherein $R^{28}$ is as defined hereinbefore);

8) $C_{2-5}$alkynyl$R^{28}$ (wherein $R^{28}$ is as defined hereinbefore);

9) $R^{29}$ (wherein $R^{29}$ represents a pyridone group, a phenyl group or a 5-6-membered aromatic heterocyclic group (linked via carbon or nitrogen) with 1–3 heteroatoms selected from O, N and S, which pyridone, phenyl or aromatic heterocyclic group may carry up to 5 substituents selected from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —C(O)$NR^{30}R^{31}$, —$NR^{32}$C(O)$R^{33}$ (wherein $R^{30}$, $R^{31}$, $R^{32}$ and $R^{33}$, which may be the same or different, each represents hydrogen, $C_{1-4}$alkyl or $C_{1-3}$alkoxy$C_{2-3}$alkyl) and a group —(—O—)$_f$($C_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl));

10) $C_{1-5}$alkyl$R^{29}$ (wherein $R^{29}$ is as defined hereinbefore);

11) $C_{2-5}$alkenyl$R^{29}$ (wherein $R^{29}$ is as defined hereinbefore);

12) $C_{2-5}$alkynyl$R^{29}$ (wherein $R^{29}$ is as defined hereinbefore);

13) $C_{1-5}$alkyl$X^6R^{29}$ (wherein $X^6$ represents —O—, —S—, —SO—, —$SO_2$—, —$NR^{34}$C(O)—; —C(O)$N^{35}$—, —$SO_2NR^{36}$—, —$NR^{37}SO_2$— or —$NR^{38}$— (wherein $R^{34}$, $R^{35}$, $R^{36}$, $R^{37}$ and $R^{38}$ each independently represents hydrogen, $C_{1-3}$alkyl or $C_{1-3}$alkoxy$C_{2-3}$alkyl) and $R^{29}$ is as defined hereinbefore);

14) $C_{2-5}$alkenyl$X^7R^{29}$ (wherein $X^7$ represents —O—, —S—, —SO—, —$SO_2$—, —$NR^{39}$C(O)—, —C(O)$NR^{40}$—, —$SO_2NR^{41}$—, —$NR^{42}SO_2$— or —$NR^{43}$— (wherein $R^{39}$, $R^{40}$, $R^{41}$, $R^{42}$ and $R^{43}$ each independently represents hydrogen, $C_{1-3}$alkyl or $C_{1-3}$alkoxy$C_{2-3}$alkyl) and $R^{29}$ is as defined hereinbefore);

15) $C_{2-5}$alkynyl$X^8R^{29}$ (wherein $X^8$ represents —O—, —S—, —SO—, —$SO_2$—, —$NR^{44}$C(O)—, —C(O)$NR^{45}$—, —$SO_2NR^{46}$—, —$NR^{47}SO_2$— or —$NR^{48}$— (wherein $R^{44}$, $R^{45}$, $R^{46}$, $R^{47}$ and $R^{48}$ each independently represents hydrogen, $C_{1-3}$alkyl or $C_{1-3}$alkoxy$C_{2-3}$alkyl) and $R^{29}$ is as defined hereinbefore);

16) $C_{1-4}$alkyl$X^9C_{1-4}$alkyl$R^{29}$ (wherein $X^9$ represents —O—, —S—, —SO—, —$SO_2$—, —$NR^{49}$C(O)—, —C(O)$NR^{50}$—, —$SO_2NR^{51}$—, —$NR^{52}SO_2$— or —$NR^{53}$— (wherein $R^{49}$, $R^{50}$, $R^{51}$, $R^{52}$ and $R^{53}$ each independently represents hydrogen, $C_{1-3}$alkyl or $C_{1-3}$alkoxy$C_{2-3}$alkyl) and $R^{29}$ is as defined hereinbefore);

17) $C_{1-4}$alkyl$X^9C_{1-4}$alkyl$R^{28}$ (wherein $X^9$ and $R^{28}$ are as defined hereinbefore);

18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

20) $C_{2-5}$alkenyl$X^9C_{1-4}$alkyl$R^{28}$ (wherein $X^9$ and $R^{28}$ are as defined hereinbefore);

21) $C_{2-5}$alkynylX$^9$C$_{1-4}$alkylR$^{28}$ (wherein X$^9$ and R$^{28}$ are as defined hereinbefore); and 22) $C_{1-4}$alkylR$^{54}$(C$_{1-4}$alkyl)$_q$(X$^9$)$_r$R$^{55}$ (wherein X$^9$ is as defined hereinbefore, q is 0 or 1, r is 0 or 1, and R$^{54}$ and R$^{55}$ are each independently selected from hydrogen, $C_{1-3}$alkyl, cyclopentyl, cyclohexyl and a 4-, 5- or 6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxyC$_{1-4}$alkyl, $C_{1-4}$alkylsulphonylC$_{1-4}$alkyl, $C_{1-4}$alkoxycarbonyl, $C_{1-4}$aminoalkyl, $C_{1-4}$alkylamino, di(C$_{1-4}$alkyl)amino, $C_{1-4}$alkylaminoC$_{1-4}$alkyl, di(C$_{1-4}$alkyl)aminoC$_{1-4}$alkyl, $C_{1-4}$alkylaminoC$_{1-4}$alkoxy, di(C$_{1-4}$alkyl)aminoC$_{1-4}$alkoxy and a group —(—O—)$_f$(C$_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl), with the proviso that R$^{54}$ cannot be hydrogen);

and additionally wherein any $C_{1-5}$alkyl, $C_{2-5}$alkenyl or $C_{2-5}$alkynyl group in R$^5$X$^1$— may bear one or more substituents selected from hydroxy, halogeno and amino);

or a salt thereof, or a prodrug thereof for example an ester or an amide, in the manufacture of a medicament for use in the production of an antiangiogenic and/or vascular permeability reducing effect in warm-blooded animals such as humans.

According to another aspect of the present invention there is provided the use of a compound of the formula I$^1$:

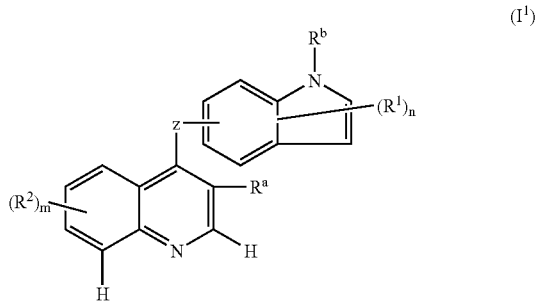

(I$^1$)

wherein:

Z is —O—, —NH—, —S—, —CH$_2$— or a direct bond; Z is linked to the benz ring of the indole group at any of the positions 4-, 5-, 6- or 7- of the indole group;

n is an integer from 0 to 5; any of the substituents R$^1$ may be attached at any free carbon atom of the indole group, such free carbon atoms may be at positions 2-, 3-, 4-, 5-, 6-, or 7- of the indole group;

m is an integer from 0 to 3;

R$^a$ represents hydrogen or fluoro;

R$^b$ represents hydrogen, $C_{1-4}$alkyl, $C_{1-4}$alkoxyC$_{1-4}$alkyl, aminoC$_{1-4}$alkyl, $C_{1-3}$alkylaminoC$_{1-4}$alkyl, di(C$_{1-3}$alkyl)aminoC$_{1-4}$alkyl, —C$_{1-5}$alkyl(ring A) wherein ring A is selected from azetidinyl, pyrrolidinyl, piperidinyl, piperazinyl, N-methylpiperazinyl, N-ethylpiperazinyl, morpholino and thiomorpholino;

R$^1$ represents hydrogen, oxo, hydroxy, halogeno, $C_{1-4}$alkyl, $C_{1-4}$alkoxy, $C_{1-4}$alkoxyC$_{1-4}$alkyl, aminoC$_{1-4}$alkyl, $C_{1-3}$alkylaminoC$_{1-4}$alkyl, di(C$_{1-3}$alkyl)aminoC$_{1-4}$alkyl, —C$_{1-5}$alkyl(ring B) wherein ring B is selected from azetidinyl, pyrrolidinyl, piperidinyl, piperazinyl, N-methylpiperazinyl, N-ethylpiperazinyl, morpholino and thiomorpholino;

R$^2$ represents hydrogen, hydroxy, halogeno, cyano, nitro, trifluoromethyl, $C_{1-3}$alkyl, $C_{1-3}$alkoxy, $C_{1-3}$alkylsulphanyl, —NR$^3$R$^4$ (wherein R$^3$ and R$^4$, which may be the same or different, each represents hydrogen or $C_{1-3}$alkyl), or R$^5$X$^1$— (wherein X$^1$ represents a direct bond, —O—, —CH$_2$—, —OC(O)—, —C(O)—, —S—, —SO—, —SO$_2$—, —NR$^6$C(O)—, —C(O)NR$^7$—, —SO$_2$NR$^8$—, —NR$^9$SO$_2$— or —NR$^{10}$— (wherein R$^6$, R$^7$, R$^8$, R$^9$ and R$^{10}$ each independently represents hydrogen, $C_{1-3}$alkyl or $C_{1-3}$alkoxyC$_{2-3}$alkyl), and R$^5$ is selected from one of the following twenty-two groups:

1) hydrogen, oxiranylC$_{1-4}$alkyl or $C_{1-5}$alkyl which may be unsubstituted or which may be substituted with one or more groups selected from hydroxy, fluoro, chloro, bromo and amino;

2) $C_{1-5}$alkylX$^2$C(O)R$^{11}$ (wherein X$^2$ represents —O— or —NR$^{12}$— (in which R$^{12}$ represents hydrogen, $C_{1-3}$alkyl or $C_{1-3}$alkoxyC$_{2-3}$alkyl) and R$^{11}$ represents $C_{1-3}$alkyl, —NR$^{13}$R$^{14}$ or —OR$^{15}$ (wherein R$^{13}$, R$^{14}$ and R$^{15}$ which may be the same or different each represents hydrogen, $C_{1-5}$alkyl or $C_{1-3}$alkoxyC$_{2-3}$alkyl));

3) $C_{1-5}$alkylX$^3$R$^{16}$ (wherein X$^3$ represents —O—, —S—, —SO—, —SO$_2$—, —OC(O)—, —NR$^{17}$C(O)—, —C(O)NR$^{18}$—, —SO$_2$NR$^{19}$—, —NR$^{20}$SO$_2$— or —NR$^{21}$— (wherein R$^{17}$, R$^{18}$, R$^{19}$, R$^{20}$ and R$^{21}$ each independently represents hydrogen, $C_{1-3}$alkyl or $C_{1-3}$alkoxyC$_{2-3}$alkyl) and R$^{16}$ represents hydrogen, $C_{1-3}$alkyl, cyclopentyl, cyclohexyl or a 4-, 5- or 6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxyC$_{1-4}$alkyl, $C_{1-4}$alkylsulphonylC$_{1-4}$alkyl, $C_{1-4}$alkoxycarbonyl, $C_{1-4}$aminoalkyl, $C_{1-4}$alkylamino, di(C$_{1-4}$alkyl)amino, $C_{1-4}$alkylaminoC$_{1-4}$alkyl, di(C$_{1-4}$alkyl)aminoC$_{1-4}$alkyl, $C_{1-4}$alkylaminoC$_{1-4}$alkoxy, di(C$_{1-4}$alkyl)aminoC$_{1-4}$alkoxy and a group —(—O—)$_f$(C$_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl));

4) $C_{1-5}$alkylX$^4$C$_{1-5}$alkylX$^5$R$^{22}$ (wherein X$^4$ and X$^5$ which may be the same or different are each —O—, —S—, —SO—, —SO$_2$—, —NR$^{23}$C(O)—, —C(O)NR$^{24}$—, SO$_2$NR$^{25}$—, NR$^{26}$SO$_2$— or —NR$^{27}$— (wherein R$^{23}$, R$^{24}$, R$^{25}$, R$^{26}$ and R$^{27}$ each independently represents hydrogen, $C_{1-3}$alkyl or $C_{1-3}$alkoxyC$_{2-3}$alkyl) and R$^{22}$ represents hydrogen, $C_{1-3}$alkyl or $C_{1-3}$alkoxyC$_{2-3}$alkyl);

5) R$^{28}$ (wherein R$^{28}$ is a 4-, 5- or 6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxyC$_{1-4}$alkyl, $C_{1-4}$alkylsulphonylC$_{1-4}$alkyl, $C_{1-4}$alkoxycarbonyl, $C_{1-4}$aminoalkyl, $C_{1-4}$alkylamino, di(C$_{1-4}$alkyl)amino, $C_{1-4}$alkylaminoC$_{1-4}$alkyl, di(C$_{1-4}$ alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl));

6) $C_{1-5}$alkyl$R^{28}$ (wherein $R^{28}$ is as defined hereinbefore);
7) $C_{2-5}$alkenyl$^{28}$ (wherein $R^{28}$ is as defined hereinbefore);
8) $C_{2-5}$alkynyl$R^{28}$ (wherein $R^{28}$ is as defined hereinbefore);
9) $R^{29}$ (wherein $R^{29}$ represents a pyridone group, a phenyl group or a 5–6-membered aromatic heterocyclic group (linked via carbon or nitrogen) with 1–3 heteroatoms selected from O, N and S, which pyridone, phenyl or aromatic heterocyclic group may carry up to 5 substituents selected from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —C(O)N$R^{30}R^{31}$, —N$R^{32}$C(O)$R^{33}$ (wherein $R^{30}$, $R^{31}$, $R^{32}$ and $R^{33}$, which may be the same or different, each represents hydrogen, $C_{1-4}$alkyl or $C_{1-3}$alkoxy$C_{1-3}$alkyl) and a group —(—O—)$_f$($C_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl));
10) $C_{1-5}$alkyl$R^{29}$ (wherein $R^{29}$ is as defined hereinbefore);
11) $C_{2-5}$alkenyl$R^{29}$ (wherein $R^{29}$ is as defined hereinbefore);
12) $C_{2-5}$alkynyl$R^{2-9}$ (wherein $R^{29}$ is as defined hereinbefore);
13) $C_{1-5}$alkyl$X^6R^{29}$ (wherein $X^6$ represents —O—, —S—, —SO—, —SO$_2$—, —N$R^{34}$C(O)—, —C(O)N$R^{35}$—, —SO$_2$N$R^{36}$—, —N$R^{37}$SO$_2$— or —N$R^{38}$— (wherein $R^{34}$, $R^{35}$, $R^{36}$, $R^{37}$ and $R^{38}$ each independently represents hydrogen, $C_{1-3}$alkyl or $C_{1-3}$alkoxy$C_{2-3}$alkyl) and $R^{29}$ is as defined hereinbefore);
14) $C_{2-5}$alkenyl$X^7R^{29}$ (wherein $X^7$ represents —O—, —S—, —SO—, —SO$_2$—, —N$R^{39}$C(O)—, —C(O)N$R^{40}$—, —SO$_2$N$R^{41}$—, —N$R^{42}$SO$_2$— or —N$R^{43}$— (wherein $R^{39}$, $R^{40}$, $R^{41}$, $R^{42}$ and $R^{43}$ each independently represents hydrogen, $C_{1-3}$alkyl or $C_{1-3}$alkoxy$C_{2-3}$alkyl) and $R^{29}$ is as defined hereinbefore);
15) $C_{2-5}$alkynyl$X^8R^{29}$ (wherein $X^8$ represents —O—, —S—, —SO—, —SO$_2$—, —N$R^{44}$C(O)—, —C(O)N$R^{45}$—, —SO$_2$N$R^{46}$—, —N$R^{47}$SO$_2$— or —N$R^{48}$— (wherein $R^{44}$, $R^{45}$, $R^{46}$, $R^{47}$ and $R^{48}$ each independently represents hydrogen, $C_{1-3}$alkyl or $C_{1-3}$alkoxy$C_{2-3}$alkyl) and $R^{29}$ is as defined hereinbefore);
16) $C_{1-4}$alkyl$X^9C_{1-4}$alkyl$R^{29}$ (wherein $X^9$ represents —O—, —S—, —SO—, —SO$_2$—, —N$R^{49}$C(O)—, —C(O)N$R^{50}$—, —SO$_2$N$R^{51}$—, —N$R^{52}$SO$_2$— or —N$R^{53}$— (wherein $R^{49}$, $R^{50}$, $R^{51}$, $R^{52}$ and $R^{53}$ each independently represents hydrogen, $C_{1-3}$alkyl or $C_{1-3}$alkoxy$C_{2-3}$alkyl) and $R^{29}$ is as defined hereinbefore);
17) $C_{1-4}$alkyl$X^9C_{1-4}$alkyl$R^{28}$ (wherein $X^9$ and $R^{28}$ are as defined hereinbefore);
18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;
19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;
20) $C_{2-5}$alkenyl$X^9C_{1-4}$alkyl$R^{28}$ (wherein $X^9$ and $R^{28}$ are as defined hereinbefore);
21) $C_{2-5}$alkynyl$X^9C_{1-4}$alkyl$R^{28}$ (wherein $X^9$ and $R^{28}$ are as defined hereinbefore); and
22) $C_{1-4}$alkyl$R^{54}$($C_{1-4}$alkyl)$_q$($X^9$)$_r$$R^{55}$ (wherein $X^9$ is as defined hereinbefore, q is 0 or 1, r is 0 or 1, and $R^{54}$ and $R^{55}$ are each independently selected from hydrogen, $C_{1-3}$alkyl, cyclopentyl, cyclohexyl and a 4-, 5- or 6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxy alkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl), with the proviso that $R^{54}$ cannot be hydrogen);

and additionally wherein any $C_{1-5}$alkyl, $C_{2-5}$alkenyl or $C_{2-5}$alkynyl group in $R^5X^1$— may bear one or more substituents selected from hydroxy, halogeno and amino);

or a salt thereof, or a prodrug thereof for example an ester or an amide, in the manufacture of a medicament for use in the production of an antiangiogenic and/or vascular permeability educing effect in warm-blooded animals such as humans.

Preferably Z is —O—, —NH—, —S— or a direct bond.
More preferably Z is —O—, —NH— or —S—.
Particularly Z is —O— or —NH—, especially —O—.
Preferably Z is linked to the indole, azaindole or indazole group at the 5- or 6-positions of the indole, azaindole or indazole group.
More preferably Z is linked to the indole, azaindole or indazole group at the 5-position of the indole, azaindole or indazole group.
Preferably Z is linked to an indole group at the 5- or 6-positions of the indole group.
More preferably Z is linked to an indole group at the 5-position of the indole group.
Preferably $R^a$ is hydrogen.
Preferably $R^b$ represents hydrogen, $C_{1-2}$alkyl, $C_{2-3}$alkenylamino$C_{2-3}$alkyl, $C_{2-3}$alkynylamino$C_{2-3}$alkyl or —$C_{2-4}$alkyl (ring A) wherein ring A is selected from piperidinyl and piperazinyl and wherein ring A may bear one or more substituents selected from $C_{1-2}$alkyl, $C_{2-3}$alkenyl, $C_{2-3}$alkynyl, hydroxy, cyano, cyano$C_{1-2}$alkyl, $C_{1-2}$alkylsulphonyl and $C_{1-2}$alkanoyl.
More preferably $R^b$ represents hydrogen, methyl, $C_{2-3}$alkenylamino$C_{2-3}$alkyl, $C_{2-3}$alkylamino$C_{2-3}$alkyl or —$C_{2-3}$alkyl(ring A) wherein ring A is selected from 4-acetylpiperazin-1-yl, 4-methylsulphonylpiperazin-1-yl, 4-cyanopiperazin-1-yl, 4-cyanomethylpiperazin-1-yl, 4-(prop-2-en-1-yl)piperazin-1-yl, 4-(prop-2-yn-1-yl)piperazin-1-yl and 4-hydroxypiperidino.
Particularly $R^b$ is hydrogen or methyl, especially hydrogen.
Advantageously $R^1$ represents hydrogen, oxo, hydroxy, halogeno, $C_{1-4}$alkyl, $C_{1-4}$alkoxy, $C_{1-4}$alkoxy$C_{1-4}$alkyl, aminoC$_{1-4}$alkyl, C$_{1-3}$alkylaminoC$_{1-4}$alkyl, di(C$_{1-3}$alkyl)aminoC$_{1-4}$alkyl, —C$_{1-5}$alkyl(ring B) wherein ring B is selected from azetidin-1-yl, pyrrolidin-1-yl, piperidin-1-yl, piperazin-1-yl, N-methylpiperazin-1-yl, N-ethylpiperazin-1-yl, morpholino and thiomorpholino.

Particularly R$^1$ represents methyl, ethyl, trifluoromethyl or halogeno.

Especially R$^1$ represents methyl, fluoro, chloro or bromo, more especially methyl or fluoro.

Preferably n is an integer from 0 to 3. More preferably n is 0, 1 or 2.

According to one aspect of the present invention G$_1$ is nitrogen and G$_2$, G$_3$, G$_4$ and G$_5$ are —CH— forming an azaindole moiety which may bear one or more substituents R$^1$ as defined hereinbefore.

According to another aspect of the present invention G$_5$ is nitrogen and G$_1$, G$_2$, G$_3$ and G$_4$ are —CH— forming an indazole moiety which may bear one or more substituents R$^1$ as defined hereinbefore.

According to another aspect of the present invention G$_1$, G$_2$, G$_3$, G$_4$ and G$_5$ are all —CH— forming an indole moiety which may bear one or more substituents R$^1$ as defined hereinbefore.

In one embodiment of the invention the optionally substituted indole, azaindole or indazole moiety of formula II:

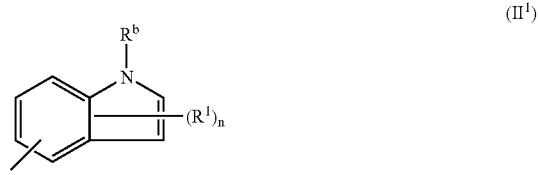

(II)

wherein R$^1$, R$^b$, G$_1$, G$_2$, G$_3$, G$_4$ and G$_5$ and n are as defined hereinbefore;
is selected from the indole moieties:
4-fluoro-2-methylindol-5-yl, 2-methylindol-5-yl, 2-methylindol-6-yl, 2,3-dimethylindol-5-yl, 1-methylindol-5-yl, 1,2-dimethylindol-5-yl, 4-fluoroindol-5-yl, 6-fluoroindol-5-yl, indol-5-yl and 3-methylindol-5-yl,
the azaindole moieties:

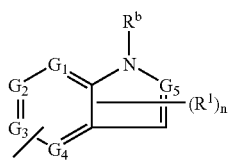

1H-pyrrolo[2,3-b]pyridin-5-yl and 2-methyl-1H-pyrrolo[2,3-b]pyridin-5-yl,
and the indazole moiety:

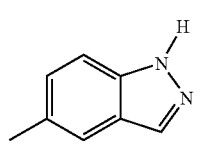

1H-indazol-5-yl.

The indole moieties are preferred over the azaindole and indazole moieties.

In one embodiment of the invention the optionally substituted indole moiety of formula II$^1$:

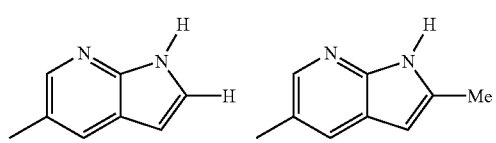

(II$^1$)

wherein R$^1$, R$^b$ and n are as defined hereinbefore;
is selected from 4-fluoro-2-methylindol-5-yl, 2-methylindol-5-yl, 2-methylindol-6-yl, 2,3-dimethylindol-5-yl, 1-methylindol-5-yl, 1,2-dimethylindol-5-yl, 4-fluoroindol-5-yl, 6-fluoroindol-5-yl and indol-5-yl.

Particularly the optionally substituted indole moiety of formula ft is selected from 4-fluoro-2-methylindol-5-yl, 4-fluoroindol-5-yl and 6-fluoroindol-5-yl, more especially from 4-fluoro-2-methylindol-5-yl.

Preferably m is an integer from 0 to 2, more preferably 1 or 2, most preferably 2.

Advantageously X$^1$ represents a direct bond, —O—, —S—, —NR$^6$C(O)—, —NR$^9$SO$_2$— or —NR$^{10}$— (wherein R$^6$, R$^9$ and R$^{10}$ each independently represents hydrogen, C$_{1-2}$alkyl or C$_{1-2}$alkoxyethyl).

Preferably X$^1$ represents a direct bond, —O—, —S—, —NR$^6$C(O)—, —NR$^9$SO$_2$— (wherein R$^6$ and R$^9$ each independently represents hydrogen or C$_{1-2}$alkyl) or NH.

More preferably X$^1$ represents —O—, —S—, —NR$^6$C(O)— (wherein R$^6$ represents hydrogen or C$_{1-2}$alkyl) or NH.

Particularly X$^1$ represents —O— or —NR$^6$C(O)— (wherein R$^6$ represents hydrogen or C$_{1-2}$alkyl), more particularly —O— or —NHC(O)—, especially —O—.

According to another aspect of the present invention X$^1$ represents —O— or a direct bond.

Advantageously X$^2$ represents —O— or NR$^{12}$ (wherein R$^{12}$ represents hydrogen, C$_{1-3}$alkyl or C$_{1-2}$alkoxyethyl).

Advantageously X$^3$ represents —O—, —S—, —SO—, —SO$_2$—, —NR$^{17}$C(O)—, —NR$^{20}$SO$_2$— or —NR$^{21}$— (wherein R$^{17}$, R$^{20}$ and R$^{21}$ each independently represents hydrogen, C$_{1-2}$alkyl or C$_{1-2}$alkoxyethyl).

Preferably X$^3$ represents —O—, —S—, —SO—, —SO$_2$— or NR$^{21}$ (wherein R$^{21}$ represents hydrogen, C$_{1-2}$alkyl or C$_{1-2}$alkoxyethyl).

More preferably X$^3$ represents —O— or —NR$^{21}$— (wherein R$^{21}$ represents hydrogen or C$_{1-2}$alkyl).

According to another aspect of the present invention X$^3$ represents —O—, —SO$_2$—, —NR$^{20}$SO$_2$— or —NR$^{21}$— (wherein R$^{20}$ and R$^{21}$ each independently represents hydrogen, C$_{1-2}$alkyl or C$_{1-2}$alkoxyethyl).

Advantageously X$^4$ and X$^5$ which may be the same or different each represents —O—, —S—, —SO—, —SO$_2$— or NR$^{27}$— (wherein R$^{27}$ represents hydrogen, C$_{1-3}$alkyl or C$_{1-2}$alkoxyethyl).

Preferably X$^4$ and X$^5$ which may be the same or different each represents —O—, —S— or NR$^{27}$— (wherein R$^{27}$ represents hydrogen, C$_{1-2}$alkyl or C$_{1-2}$alkoxyethyl).

More preferably X$^4$ and X$^5$ which may be the same or different each represents —O— or —NH—.

Especially X$^4$ and X$^5$ each represents —O—.

Advantageously $X^6$ represents —O—, —S— or —NR$^{38}$— (wherein R$^{38}$ represents hydrogen, C$_{1-2}$alkyl or C$_{1-2}$alkoxyethyl).

Preferably $X^6$ represents —O— or —NR$^{38}$— (wherein R$^{38}$ represents hydrogen or C$_{1-2}$alkyl).

Especially $X^6$ represents —O—.

Advantageously $X^7$ represents —O—, —S— or NR$^{43}$— (wherein R$^{43}$ represents hydrogen, C$_{1-2}$alkyl or C$_{1-2}$alkoxyethyl).

Preferably $X^7$ represents —O— or —NR$^{43}$— (wherein R$^{43}$ represents hydrogen or C$_{1-2}$alkyl).

Advantageously $X^8$ represents —O—, —S— or —NR$^{48}$— (wherein R$^{48}$ represents hydrogen, C$_{1-2}$alkyl or C$_{1-2}$alkoxyethyl).

Preferably $X^8$ represents —O— or —NR$^{48}$— (wherein R$^{48}$ represents hydrogen or C$_{1-2}$alkyl).

Advantageously $X^9$ represents —O—, —S— or —NR$^{53}$— (wherein R$^{53}$ represents hydrogen, C$_{1-2}$alkyl or C$_{1-2}$alkoxyethyl).

Preferably $X^9$ represents —O— or —NR$^{53}$— (wherein Rs$^3$ represents hydrogen or C$_{1-2}$alkyl).

According to another aspect of the present invention $X^9$ represents —O—, —CONR$^{50}$— or —NR$^{53}$— (wherein R$^{50}$ and R$^{53}$ each independently represents hydrogen or C$_{1-2}$alkyl).

Conveniently R$^{28}$ is pyrrolidinyl, piperazinyl, piperidinyl, imidazolidinyl, azetidinyl, morpholino or thiomorpholino which group may bear 1 or 2 substituents selected from oxo, hydroxy, halogeno, cyano, C$_{1-3}$cyanoalkyl, C$_{1-3}$alkyl, C$_{1-3}$hydroxyalkyl, C$_{1-3}$alkoxy, C$_{1-2}$alkoxyC$_{1-3}$alkyl, C$_{1-2}$alkylsulphonylC$_{1-3}$alkyl, C$_{1-3}$alkoxycarbonyl, C$_{1-3}$alkylamino, di(C$_{1-3}$alkyl)amino, C$_{1-3}$alkylaminoC$_{1-3}$alkyl, di(C$_{1-3}$alkyl)aminoC$_{1-3}$alkyl, C$_{1-3}$alkylaminoC$_{1-3}$alkoxy, di(C$_{1-3}$alkyl)aminoC$_{1-3}$alkoxy and a group —(—O—)$_f$(C$_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from C$_{1-3}$alkyl).

Advantageously R$^{28}$ is pyrrolidinyl, piperazinyl, piperidinyl, azetidinyl, morpholino or thiomorpholino which group may bear 1 or 2 substituents selected from oxo, hydroxy, halogeno, cyano, C$_{1-3}$cyanoalkyl, C$_{1-3}$alkyl, C$_{1-3}$hydroxyalkyl, C$_{1-3}$alkoxy, C$_{1-2}$alkoxyC$_{1-3}$alkyl, C$_{1-2}$alkylsulphonylC$_{1-3}$alkyl, C$_{1-3}$alkoxycarbonyl, C$_{1-3}$alkylamino, di(C$_{1-3}$alkyl)amino, C$_{1-3}$alkylaminoC$_{1-3}$alkyl, di(C$_{1-3}$alkyl)aminoC$_{1-3}$alkyl, C$_{1-3}$alkylaminoC$_{1-3}$alkoxy, di(C$_{1-3}$alkyl)aminoC$_{1-3}$alkoxy and a group —(—O—)$_f$(C$_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

In one embodiment of the present invention R$^{28}$ is pyrrolidinyl, piperazinyl, piperidinyl, azetidinyl, morpholino or thiomorpholino which group may bear 1 or 2 substituents selected from a group —(—O—)$_f$(C$_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

Particularly R$^{28}$ is pyrrolidinyl, piperazinyl, piperidinyl, azetidinyl, morpholino or thiomorpholino which group may bear 1 or 2 substituents selected from oxo, hydroxy, halogeno, cyano, C$_{1-3}$cyanoalkyl, C$_{1-3}$alkyl, C$_{1-3}$hydroxyalkyl, C$_{1-3}$alkoxy, C$_{1-2}$alkoxyC$_{1-3}$alkyl and C$_{1-2}$alkylsulphonylC$_{1-3}$ alkyl.

According to another aspect of the present invention, preferably R$^{28}$ is pyrrolidinyl, piperazinyl, piperidinyl, morpholino or thiomorpholino which group may bear 1 or 2 substituents selected from oxo, hydroxy, halogeno, cyano, C$_{1-3}$cyanoalkyl, C$_{1-3}$alkyl, C$_{1-3}$hydroxyalkyl, C$_{1-3}$alkoxy, C$_{1-2}$alkoxyC$_{1-3}$alkyl and C$_{1-2}$alkylsulphonylC$_{1-3}$alkyl.

Where R$^{29}$ is a 5–6-membered aromatic heterocyclic group, it preferably has 1 or 2 heteroatoms, selected from O, N and S, of which more preferably one is N, and may be substituted as hereinbefore defined.

R$^{29}$ is particularly a pyridone, phenyl, pyridyl, imidazolyl, thiazolyl, thienyl, triazolyl or pyridazinyl group which group may be substituted as hereinbefore defined, more particularly a pyridone, pyridyl, imidazolyl, thiazolyl or triazolyl group, especially a pyridone, pyridyl, imidazolyl or triazolyl group which group may be substituted as hereinbefore defined.

In one embodiment of the invention R$^{29}$ represents a pyridone, phenyl or 5-6-membered aromatic heterocyclic group with 1 to 3 heteroatoms selected from O, N and S, which group may preferably carry up to 2 substituents, more preferably up to one substituent, selected from the group of substituents as hereinbefore defined.

In the definition of R$^{29}$, conveniently substituents are selected from halogeno, C$_{1-4}$alkyl, C$_{1-4}$alkoxy, cyano and a group —(—O—)$_f$(C$_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from C$_{1-3}$alkyl).

In the definition of R$^{29}$, more conveniently substituents are selected from chloro, fluoro, methyl, ethyl and a group —(—O—)$_f$(C$_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

According to another emodiment of the present invention in the definition of R$^{29}$, conveniently substituents are selected from halogeno, C$_{1-4}$alkyl, C$_{1-4}$alkoxy and cyano, more conveniently substituents are selected from chloro, fluoro, methyl and ethyl.

Advantageously R$^{54}$ and R$^{55}$ are each independently a 4-, 5- or 6-membered saturated heterocyclic group with 1–2 heteroatoms, selected independently from O, S and N, which cyclic group may bear 1 or 2 substituents selected from oxo, hydroxy, halogeno, cyano, C$_{1-3}$cyanoalkyl, C$_{1-3}$alkyl, C$_{1-3}$hydroxyalkyl, C$_{1-3}$alkoxy, C$_{1-2}$alkoxyC$_{1-3}$alkyl, C$_{1-2}$alkylsulphonylC$_{1-3}$alkyl, C$_{1-3}$alkoxycarbonyl and a group —(—O—)$_f$(C$_{1-3}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from C$_{1-3}$alkyl).

Preferably R$^{54}$ and R$^{55}$ are each selected from pyrrolidinyl, piperazinyl, piperidinyl, imidazolidinyl, azetidinyl, morpholino and thiomorpholino which group may bear 1 or 2 substituents selected from oxo, hydroxy, halogeno, cyano, C$_{1-3}$cyanoalkyl, C$_{1-3}$alkyl, C$_{1-3}$hydroxyalkyl, C$_{1-3}$alkoxy, C$_{1-2}$alkoxyC$_{1-3}$alkyl, C$_{1-2}$alkylsulphonylC$_{1-3}$alkyl, C$_{1-3}$alkoxycarbonyl and a group —(—O—)$_f$(C$_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from C$_{1-3}$alkyl).

More preferably R$^{54}$ and R$^{55}$ are each selected from pyrrolidinyl, piperazinyl, piperidinyl, azetidinyl, morpholino and thiomorpholino which group may bear 1 or 2 substituents selected from oxo, hydroxy, halogeno, cyano, C$_{1-3}$cyanoalkyl, C$_{1-3}$alkyl, C$_{1-3}$hydroxyalkyl, C$_{1-3}$alkoxy, $C_{1-2}$alkoxy$C_{1-3}$alkyl, $C_{1-2}$alkylsulphonyl$C_{1-3}$alkyl, $C_{1-3}$alkoxycarbonyl and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

Particularly $R^{54}$ and $R^{55}$ are each selected from pyrrolidinyl, piperazinyl, piperidinyl, azetidinyl, morpholino and thiomorpholino which group may bear 1 or 2 substituents selected from a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

More particularly $R^{54}$ and $R^{55}$ are each selected from pyrrolidinyl, piperazinyl, piperidinyl, azetidinyl, morpholino and thiomorpholino which group is unsubstituted.

Conveniently $R^2$ represents hydroxy, halogeno, cyano, nitro, trifluoromethyl, $C_{1-3}$alkyl, amino or $R^5X^1$— [wherein $X^1$ is as hereinbefore defined and $R^5$ is selected from one of the following twenty-two groups:

1) oxiranyl$C_{1-4}$alkyl or $C_{1-5}$alkyl which may be unsubstituted or which may be substituted with one or more groups selected from fluoro, chloro and bromo, or $C_{2-5}$alkyl which may be unsubstituted or substituted with one or more groups selected from hydroxy and amino;
2) $C_{2-3}$alkyl$X^2C(O)R^{11}$ (wherein $X^2$ is as hereinbefore defined and $R^{11}$ represents $C_{1-3}$alkyl, —$NR^{13}R^{14}$ or —$OR^{15}$ (wherein $R^{13}$, $R^{14}$ and $R^{15}$ which maybe the same or different are each $C_{1-4}$alkyl or $C_{1-2}$alkoxyethyl));
3) $C_{2-4}$alkyl$X^3R^{16}$ (wherein $X^3$ is as hereinbefore defined and $R^{16}$ represents hydrogen, $C_{1-3}$alkyl, cyclopentyl, cyclohexyl or a 4-, 5- or 6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-3}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl));
4) $C_{2-3}$alkyl$X^4C_{2-3}$alkyl$X^5R^{22}$ (wherein $X^4$ and $X^5$ are as hereinbefore defined and $R^{22}$ represents hydrogen or $C_{1-3}$alkyl);
5) $R^{28}$ (wherein $R^{28}$ is as defined hereinbefore);
6) $C_{1-5}$alkyl$R^{56}$ (wherein $R^{56}$ is a 4-, 5- or 6-membered saturated heterocyclic group with 1–2 heteroatoms, selected independently from O, S and N, which heterocyclic group is linked to $C_{1-5}$alkyl through a carbon atom and which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkanoyl, $C_{1-4}$alkoxy$C_{1-4}$alkyl, $C_{1-4}$alkylsulphonyl, $C_{1-4}$alkylsulphonyl$C_{1-4}$alkyl, $C_{1-4}$alkoxycarbonyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl)) or $C_{2-5}$alkyl$R^{57}$ (wherein $R^{57}$ is a 4-, 5- or 6-membered saturated heterocyclic group with 1–2 heteroatoms, of which one is N and the other may be selected independently from O, S and N, which heterocyclic group is linked to $C_{2-5}$alkyl through a nitrogen atom and which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkanoyl, $C_{1-4}$alkoxy$C_{1-4}$alkyl, $C_{1-4}$alkylsulphonyl, $C_{1-4}$alkylsulphonyl$C_{1-4}$alkyl, $C_{1-4}$alkoxycarbonyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl));
7) $C_{3-4}$alkenyl$R^{58}$ (wherein $R^{58}$ represents $R^{56}$ or $R^{57}$ as defined hereinbefore);
8) $C_{3-4}$alkyl$R^{58}$ (wherein $R^{58}$ represents $R^{56}$ or $R^{57}$ as defined hereinbefore);
9) $R^{29}$ (wherein $R^{29}$ is as defined hereinbefore);
10) $C_{1-5}$alkyl$R^{29}$ (wherein $R^{29}$ is as defined hereinbefore);
11) $C_{3-5}$alkenyl$^{29}$ (wherein $R^{29}$ is as defined hereinbefore);
12) $C_{3-5}$alkynyl$R^{29}$ (wherein $R^{29}$ is as defined hereinbefore);
13) $C_{1-5}$alkyl$X^6R^{29}$ (wherein $X^6$ and $R^{29}$ are as defined hereinbefore);
14) $C_{4-5}$alkenyl$X^7R^{29}$ (wherein $X^7$ and $R^{29}$ are as defined hereinbefore);
15) $C_{4-5}$alkynyl$X^8R^{29}$ (wherein $X^8$ and $R^{29}$ are as defined hereinbefore);
16) $C_{2-3}$alkyl$X^9C_{1-3}$alkyl$R^{29}$ (wherein $X^9$ and $R^{29}$ are as defined hereinbefore);
17) $C_{2-3}$alkyl$X^9C_{1-3}$alkyl$R^{28}$ (wherein $X^9$ and $R^{28}$ are as defined hereinbefore);
18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;
19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;
20) $C_{2-5}$alkenyl$X^9C_{1-3}$alkyl$R^{28}$ (wherein $X^9$ and $R^{28}$ are as defined hereinbefore);
21) $C_{2-5}$alkynyl$X^9C_{1-3}$alkyl$R^{28}$ (wherein $X^9$ and $R^{28}$ are as defined hereinbefore); and
22) $C_{1-3}$alkyl$R^{54}$($C_{1-4}$alkyl)$_q$($X^9$)$_r$$R^{55}$ (wherein $X^9$, q, r, $R^{54}$ and $R^{55}$ are as defined hereinbefore);

and additionally wherein any $C_{1-5}$alkyl, $C_{2-5}$alkenyl or $C_{2-5}$alkynyl group in $R^5X^1$— may bear one or more substituents selected from hydroxy, halogeno and amino].

Advantageously $R^2$ represents hydroxy, halogeno, cyano, nitro, trifluoromethyl, $C_{1-3}$alkyl, amino or $R^5X^1$— wherein $X^1$ is as hereinbefore defined and $R^5$ is selected from one of the following twenty-two groups:

1) $C_{1-4}$alkyl which may be unsubstituted or which may be substituted with one or more groups selected from fluoro, chloro and bromo, or $C_{2-5}$alkyl which may be unsubstituted or substituted with one or more groups selected from hydroxy and amino;

2) $C_{2-3}$alkyl$X^2C(O)R^{11}$ (wherein $X^2$ is as hereinbefore defined and $R^{11}$ represents —$NR^{13}R^{14}$ or —$OR^{15}$ (wherein $R^{13}$, $R^{14}$ and $R^{15}$ which may be the same or different are each $C_{1-4}$alkyl or $C_{1-2}$alkoxyethyl));

3) $C_{2-4}$alkyl$X^3R^{16}$ (wherein $X^3$ is as hereinbefore defined and $R^{16}$ is a group selected from $C_{1-3}$alkyl, cyclopentyl, cyclohexyl, pyrrolidinyl, piperazinyl, piperidinyl, imidazolidinyl, azetidinyl and tetrahydropyranyl, which $C_{1-3}$alkyl group may bear 1 or 2 substituents selected from oxo, hydroxy, halogeno and $C_{1-2}$alkoxy and which cyclopentyl, cyclohexyl, pyrrolidinyl, piperazinyl, piperidinyl, imidazolidinyl, azetidinyl or tetrahydropyranyl group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl$C_{1-3}$alkyl, $C_{1-3}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from $C_{1-3}$alkyl));

4) $C_{2-3}$alkyl$X^4C_{2-3}$alkyl$X^5R^{22}$ (wherein $X^4$ and $X^5$ are as hereinbefore defined and $R^{22}$ represents hydrogen or $C_{1-3}$alkyl);

5) $R^{28}$ (wherein $R^{28}$ is as defined hereinbefore);

6) $C_{1-4}$alkyl$R^{59}$ (wherein $R^{59}$ is a group selected from pyrrolidinyl, piperazinyl, piperidinyl, imidazolidin-1-yl, azetidinyl, 1,3-dioxolan-2-yl, 1,3-dioxan-2-yl, 1,3-dithiolan-2-yl and 1,3-dithian-2-yl, which group is linked to $C_{1-4}$alkyl through a carbon atom and which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkanoyl, $C_{1-2}$alkoxy$C_{1-3}$alkyl, $C_{1-2}$alkylsulphonyl, $C_{1-2}$alkylsulphonyl$C_{1-3}$alkyl, $C_{1-3}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from $C_{1-3}$alkyl)) or $C_{2-4}$alkyl$R^{60}$ (wherein $R^{60}$ is a group selected from morpholino, thiomorpholino, azetidin-1-yl, pyrrolidin-1-yl, piperazin-1-yl and piperidino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkanoyl, $C_{1-2}$alkoxy$C_{1-3}$alkyl, $C_{1-2}$alkylsulphonyl, $C_{1-2}$alkylsulphonyl$C_{1-3}$alkyl, $C_{1-3}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from $C_{1-3}$alkyl));

7) $C_{3-4}$alkenyl$R^{61}$ (wherein $R^{61}$ represents $R^{59}$ or $R^{60}$ as defined hereinbefore);

8) $C_{3-4}$alkynyl$R^{61}$ (wherein $R^{61}$ represents $R^{59}$ or $R^{60}$ as defined hereinbefore);

9) $R^{29}$ (wherein $R^{29}$ is as defined hereinbefore);

10) $C_{1-4}$alkyl$R^{29}$ (wherein $R^{29}$ is as defined hereinbefore);

11) 1-$R^{29}$prop-1-en-3-yl or 1-$R^{29}$but-2-en-4-yl (wherein $R^{29}$ is as defined hereinbefore with the proviso that when $R^5$ is 1-$R^{29}$prop-1-en-3-yl, $R^{29}$ is linked to the alkenyl group via a carbon atom);

12) 1-$R^{29}$prop-1-yn-3-yl or 1-$R^{2-9}$but-2-yn-4-yl (wherein $R^{29}$ is as defined hereinbefore with the proviso that when R is 1-$R^{29}$prop-1-yn-3-yl, $R^{29}$ is linked to the alkynyl group via a carbon atom);

13) $C_{1-5}$alkyl$X^6R^{29}$ (wherein $X^6$ and $R^{29}$ are as defined hereinbefore);

14) 1-($R^{29}X^7$)but-2-en-4-yl (wherein $X^7$ and $R^{29}$ are as defined hereinbefore);

15) 1-($R^{29}X^8$)but-2-yn-4-yl (wherein $X^8$ and $R^{29}$ are as defined hereinbefore);

16) $C_{2-3}$alkyl$X^9C_{1-3}$alkyl$R^{29}$ (wherein $X^9$ and $R^{29}$ are as defined hereinbefore);

17) $C_{2-3}$alkyl$X^9C_{1-3}$alkyl$R^{28}$ (wherein $X^9$ and $R^{28}$ are as defined hereinbefore);

18) $C_{2-5}$alkenyl which may be unsubstituted or which may be substituted with one or more fluorine atoms or with one or two groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

19) $C_{2-5}$alkynyl which may be unsubstituted or which may be substituted with one or more fluorine atoms or with one or two groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

20) $C_{2-4}$alkenyl$X^9C_{1-3}$alkyl$R^{28}$ (wherein $X^9$ and $R^{28}$ are as defined hereinbefore);

21) $C_{2-4}$alkynyl$X^9C_{1-3}$alkyl$R^{28}$ (wherein $X^9$ and $R^{28}$ are as defined hereinbefore); and 22) $C_{1-3}$alkyl$R^{54}(C_{1-3}$alkyl$)_q(X^9)_rR^{55}$ (wherein $X^9$, q, r, $R^{54}$ and $R^{55}$ are as defined hereinbefore);

and additionally wherein any $C_{1-5}$alkyl, $C_{2-5}$alkenyl or $C_{2-5}$alkynyl group in $R^5X^1$— may bear one or more substituents selected from hydroxy, halogeno and amino].

Preferably $R^2$ represents hydroxy, halogeno, nitro, trifluoromethyl, $C_{1-3}$alkyl, cyano, amino or $R^5X^1$— [wherein $X^1$ is as hereinbefore defined and $R^5$ is selected from one of the following twenty groups:

1) $C_{1-3}$alkyl which may be unsubstituted or which may be substituted with one or more groups selected from fluoro, chloro and bromo, or $C_{2-3}$alkyl which maybe unsubstituted or substituted with one or more groups selected from hydroxy and amino;

2) 2-(3,3-dimethylureido)ethyl, 3-(3,3-dimethylureido)propyl, 2-(3-methylureido)ethyl, 3-(3-ethylureido)propyl, 2-ureidoethyl, 3-ureidopropyl, 2-(N,N-dimethylcarbamoyloxy)ethyl, 3-N,N-dimethylcarbamoyloxy)propyl, 2-(N-methylcarbamoyloxy)ethyl, 3-(N-methylcarbamoyloxy)propyl, 2-(carbamoyloxy)ethyl, 3-(carbamoyloxy)propyl, or 2-N-methyl-N-(butoxycarbonyl)amino)ethyl;

3) $C_{2-3}$alkyl$X^3R^{16}$ (wherein $X^3$ is as hereinbefore defined and $R^{16}$ is a group selected from $C_{1-3}$alkyl, cyclopentyl, cyclohexyl, pyrrolidinyl, piperidinyl, piperazinyl, azetidinyl, imidazolidinyl and tetrahydropyranyl which group is linked to $X^3$ through a carbon atom and which $C_{1-3}$alkyl group may bear 1 or 2 substituents selected from hydroxy, halogeno and $C_{1-2}$alkoxy and which cyclopentyl, cyclohexyl, pyrrolidinyl, piperidinyl, piperazinyl, azetidinyl, imidazolidinyl or tetrahydropyranyl group may bear one substituent selected from oxo, hydroxy, halogeno, cyano, $C_{1-2}$cyanoalkyl, $C_{1-2}$alkyl, $C_{1-2}$hydroxyalkyl, $C_{1-2}$alkoxy, $C_{1-2}$alkoxy$C_{1-3}$alkyl, $C_{1-2}$alkylsulphonyl$C_{1-3}$alkyl, $C_{1-2}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$akyl, $C_{1-3}$alkylamino$C_{1-3}$alkoxy, di($C_{1-3}$alkyl)amino$C_{1-3}$ alkoxy and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino));

4) $C_{2-3}$alkyl$X^4C_{2-3}$alkyl$X^5R^{22}$ (wherein $X^4$ and $X^5$ are as hereinbefore defined a represents hydrogen or $C_{1-2}$alkyl);

5) $R^{28}$ (wherein $R^{28}$ is as defined hereinbefore);

6) $C_{1-3}$alkyl$R^{59}$ (wherein $R^{59}$ is a group selected from pyrrolidinyl, piperazinyl, piperidinyl, azetidinyl, imidazolidinyl, 1,3-dioxolan-2-yl, 1,3-dioxan-2-yl, 1,3-dithiolan-2-yl and 1,3-dithian-2-yl, which group is linked to $C_{1-3}$alkyl through a carbon atom and which group may bear 1 or 2 substituents selected from oxo, hydroxy, halogeno, cyano, $C_{1-2}$cyanoalyl, $C_{1-2}$alkyl, $C_{1-2}$hydroxyalkyl, $C_{1-2}$alkoxy, $C_{1-2}$alkanoyl, $C_{1-2}$alkoxy$C_{1-3}$alkyl, $C_{1-2}$alkylsulphonyl, $C_{1-2}$alkylsulphonyl$C_{1-3}$alkyl, $C_{1-2}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$ alkoxy and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino)) or $C_{2-3}$alkyl$R^{60}$ (wherein $R^{60}$ is a group selected from morpholino, thiomorpholino, azetidin-1-yl, pyrrolidin-1-yl, piperazin-1-yl and piperidino which group may bear 1 or 2 substituents selected from oxo, hydroxy, halogeno, cyano, $C_{1-2}$cyanoalkyl, $C_{1-2}$alkyl, $C_{1-2}$hydroxyalkyl, $C_{1-2}$alkoxy, $C_{1-2}$alkanoyl, $C_{1-2}$alkoxy$C_{1-3}$alkyl, $C_{1-2}$alkylsulphonyl, $C_{1-2}$alkylsulphonyl$C_{1-3}$alkyl, $C_{1-2}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$ alkoxy and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino));

7) $R^{29}$ (wherein $R^{29}$ is as defined hereinbefore);

8) $C_{1-4}$alkyl$R^{29}$ (wherein $R^{29}$ is as defined hereinbefore);

9) 1-$R^{29}$but-2-en-4-yl (wherein $R^{29}$ is as defined hereinbefore);

10) 1-$R^{29}$but-2-yn-4-yl (wherein $R^{29}$ is as defined hereinbefore);

11) $C_{1-3}$alkyl$X^6R^{29}$ (wherein $X^6$ and $R^{29}$ are as defined hereinbefore);

12) 1-($R^{29}X^7$)but-2-en-4-yl (wherein $X^7$ and $R^{29}$ are as defined hereinbefore);

13) 1-($R^{29}X^8$)but-2-yn-4-yl (wherein $X^8$ and $R^{29}$ are as defined hereinbefore);

14) $C_{2-3}$alkyl$X^9C_{1-3}$alkyl$R^{29}$ (wherein $X^9$ and $R^{29}$ are as defined hereinbefore);

15) $C_{2-3}$alkyl$X^9C_{1-3}$alkyl$R^{28}$ (wherein $X^9$ and $R^{28}$ are as defined hereinbefore);

16) $C_{2-5}$alkenyl which may be unsubstituted or which may be substituted with one or more fluorine atoms or with one or two groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

17) $C_{2-5}$alkynyl which may be unsubstituted or which may be substituted with one or more fluorine atoms or with one or two groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

18) $C_{2-3}$alkenyl$X^9C_{1-3}$alkyl$R^{28}$ (wherein $X^9$ and $R^{28}$ are as defined hereinbefore);

19) $C_{2-3}$alkynyl$X^9C_{1-3}$alkyl$R^{28}$ (wherein $X^9$ and $R^{28}$ are as defined hereinbefore); and 20) $C_{1-3}$alkyl$R^{54}(C_{1-3}$alkyl)$_q(X^9)_rR^{55}$ (wherein $X^9$, q, r, $R^{54}$ and $R^{55}$ are as defined hereinbefore);

and additionally wherein any $C_{1-5}$alkyl $C_{2-5}$alkenyl or $C_{2-5}$alkynyl group in $R^5X^1$— may bear one or more substituents selected from hydroxy, halogeno and amino].

More preferably $R^2$ represents hydroxy, $C_{1-3}$alkyl, amino or $R^5X^1$— [wherein $X^1$ is as hereinbefore defined and $R^5$ represents methyl, ethyl, benzyl, trifluoromethyl, 2,2,2-trifluoroethyl, 2-hydroxyethyl, 3-hydroxypropyl, 2-methoxyethyl, 3-methoxypropyl, 2-(methylsulphonyl)ethyl, 2-(methylsulphonyl)ethyl, 2-(ethylsulphinyl)ethyl, 2-(ethylsulphonyl)ethyl, 2-N,N-dimethylsulphamoyl)ethyl, 2-(N-methylsulphamoyl)ethyl, 2-sulphamoyl)ethyl, 2-(methylamino)ethyl, 3-(methylamino)propyl, 2-(ethylamino)ethyl, 3-(ethylamino)propyl, 2-(N,N-dimethylamino)ethyl, 3-(N,N-dimethylamino)propyl, 2-(N,N-diethylamino)ethyl, 3-(N,N-diethylamino)propyl, 2-N-methyl-N-methylsulphonylamino)ethyl, 3-(N-methyl-N-methylsulphonylamino)propyl, 2-morpholinoethyl, 3-morpholinopropyl, 2-piperidinoethyl, 3-piperidinopropyl, 2-(methylpiperidino)ethyl, 3-(methylpiperidino)propyl, 2-(ethylpiperidino)ethyl, 3-(ethylpiperidino)propyl, 2-((2-methoxyethyl)piperidino)ethyl, 3-((2-methoxyethyl)piperidino)propyl, 2-((2-methylsulphonyl)ethylpiperidino)ethyl, 3-((2-methylsulphonyl)ethylpiperidino)propyl, piperidin-3-ylmethyl, piperidin-4-ylmethyl, 2-(piperidin-3-yl)ethyl, 2-(piperidin-4-yl)ethyl, 3-(piperidin-3-yl)propyl, 3-(piperidin-4-yl)propyl, 2-(piperidin-2-yl)ethyl, 3-(piperidin-2-yl)propyl, (1-methylpiperidin-3-yl)methyl, (1-methylpiperidin-4-yl)methyl, 2-(4-hydroxypiperidino)ethyl, 3-(4-hydroxypiperidino)propyl, (1-cyanomethylpiperidin-3-yl)methyl, (1-cyanomethylpiperidin-4-yl)methyl, 2-(methylpiperidin-3-yl)ethyl, 2-(methylpiperidin-4-yl)ethyl, 2-(1-cyanomethylpiperidin-3-yl)ethyl, 2-(1-cyanomethylpiperidin-4-yl)ethyl, 3-(methylpiperidin-3-yl)propyl, 3-(methylpiperidin-4-yl)propyl, 3-(1-cyanomethylpiperidin-3-yl)propyl, 3-(1-cyanomethylpiperidin-4-yl)propyl, 2-(ethylpiperidin-3-yl)ethyl, 2-(ethylpiperidin-4-yl)ethyl, 3-(ethylpiperidin-3-yl)propyl, 3-(ethylpiperidin-4-yl)propyl, ((2-methoxyethyl)piperidin-3-yl)methyl, ((2-methoxyethyl)piperidin-4-yl)methyl, 2-((2-methoxyethyl)piperidin-3-yl)ethyl, 2-((2-methoxyethyl)piperidin-4-yl)ethyl, 3-((2-methoxyethyl)piperidin-3-yl)propyl, 3-((2-methoxyethyl)piperidin-4-yl)propyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 1-isopropylpiperidin-2-ylmethyl, 1-isopropylpiperidin-3-ylmethyl, 1-isopropylpiperidin-4-ylmethyl, 2-(1-isopropylpiperidin-2-yl)ethyl, 2-(1-isopropylpiperidin-3-yl)ethyl, 2-(1-isopropylpiperidin-4-yl)ethyl, 3-(1-isopropylpiperidin-2-yl)propyl, 3-(1-isopropylpiperidin-3-yl)propyl, 3-(1-isopropylpiperidin-4-yl)propyl, 2-(piperidin-4-yloxy)ethyl, 3-(piperidin-4-yloxy)propyl, 2-(1-(cyanomethyl)piperidin-4-yloxy)ethyl, 3-(1-(cyanomethyl)piperidin-4-yloxy)propyl, 2-(1-(2-cyanoethyl)piperidin-4-yloxy)ethyl, 3-(1-(2-cyanoethyl)piperidin-4-yloxy)propyl, 2-(piperazin-1-yl)ethyl, 3-(piperazin-1-yl)propyl, (pyrrolidin-2-yl)methyl, 2-(pyrrolidin-1-yl)ethyl, 3-(pyrrolidin-1-yl)propyl, (2-oxo-tetrahydro-2H-pyrrolidin-5-yl)methyl, 5(R)-(2-oxo-tetrahydro-2H-pyrrolidin-5-yl)methyl, (5S)-(2-oxo-tetrahydro-2H-pyrrolidin-5-yl)methyl, (1,3-dioxolan-2-yl)methyl, 2-(1,3-dioxolan-2-yl)ethyl, 2-(2-methoxyethylamino)ethyl, 2-(N-(2-methoxyethyl)-N-methylamino)ethyl, 2-(2-hydroxyethylamino)ethyl, 3-(2-methoxyethylamino)propyl, 3-(N-(2-methoxyethyl)-N-methylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(2-methylimidazol-1-yl)ethyl, 2-(2-ethylimidazol-1-yl)ethyl, 3-(2-methylimidazol-1-yl)propyl, 3-(2-ethylimidazol-1-yl)propyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 3-pyridylmethyl, 2-(3-pyridyl)ethyl, 3-(3-pyridyl)propyl, 2-(4-pyridyloxy)ethyl, 2-(4-pyridylamino)ethyl, 2-(4-oxo-1,4-dihydro-1-pyridyl)ethyl, 2-(2-oxo-imidazolidin-1-yl)ethyl, 3-(2-oxo-imidazolidin-1-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 2-(4-cyanomethylpiperazin-1-yl)ethyl, 3-(4-cyanomethylpiperazin-1-yl)propyl, 2-(4-acetylpiperazin-1-yl)ethyl, 3-(4-acetylpiperazin-1-yl)propyl, 2-(4-methylsulphonylpiperazin-1-yl)ethyl, 3-(4-methylsulphonylpiperazin-1-yl)propyl, 3-(methylsulphinyl)propyl, 3-(methylsulphonyl)propyl, 3-(ethylsulphinyl)propyl, 3-(ethylsulphonyl)propyl, 2-(5-methyl-1,2,4-triazol-1-yl)ethyl, morpholino, 2-((N-(1-methylimidazol-4-ylsulphonyl)-N-methyl)amino)ethyl, 2-((N-(3-morpholinopropylsulphonyl)-N-methyl)amino)ethyl, 2-((N-methyl-N-4-pyridyl)amino)ethyl, 3-(4-oxidomorpholino)propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2-((2-(pyrrolidin-1-yl)ethyl)carbamoyl)vinyl, 3-((2-(pyrrolidin-1-yl)ethyl)carbamoyl)prop-2-en-1-yl, 1-(2-pyrrolidinylethyl)piperidin-4-ylmethyl, 1-(3-pyrrolidinylpropyl)piperidin-4-ylmethyl, 1-(2-piperidinylethyl)piperidin-4-ylmethyl, 1-(3-piperidinylpropyl)piperidin-4-ylmethyl, 1-(2-morpholinoethyl)piperidin-4-ylmethyl, 1-(3-morpholinopropyl)piperidin-4-ylmethyl, 1-(2-thiomorpholinoethyl)piperidin-4-ylmethyl, 1-(3-thiomorpholinopropyl)piperidin-4-ylmethyl, 1-(2-azetidinylethyl)piperidin-4-ylmethyl, 1-(3-azetidinylpropyl)piperidin-4-ylmethyl, 2-(1-(2-pyrrolidinylethyl)piperidin-4-yl)ethyl, 2-(1-(3-pyrrolidinylpropyl)piperidin-4-yl)ethyl, 2-(1-(2-piperidinylethyl)piperidin-4-yl)ethyl, 2-(1-(3-piperidinylpropyl)piperidin-4-yl)ethyl, 2-(1-(2-morpholinoethyl)piperidin-4yl)ethyl, 2-(1-(3-morpholinopropyl)piperidin-4-yl)ethyl, 2-(1-(2-thiomorpholinoethyl)piperidin-4-yl)ethyl, 2-(1-(3-thiomorpholinopropyl)piperidin-4-yl)ethyl, 2-(1-(2-azetidinylethyl)piperidin-4-yl)ethyl, 2-(1-(3-azetidinylpropyl)piperidin-4-yl)ethyl, 3-morpholino-2-hydroxypropyl, (2R)-3-morpholino-2-hydroxypropyl, (2S)-3-morpholino-2-hydroxypropyl, 3-piperidino-2-hydroxypropyl, (2R)-3-piperidino-2-hydroxypropyl, (2S)-3-piperidino-2-hydroxypropyl, 3-pyrrolidin-1-yl-2-hydroxypropyl, (2R)-3-pyrrolidin-1-yl-2-hydroxypropyl, (2S)-3-pyrrolidin-1-yl-2-hydroxypropyl, 3-(1-methylpiperazin-4-yl)-2-hydroxypropyl, (2R)-3-(1-methylpiperazin-4-yl)-2-hydroxypropyl, (2S)-3-(1-methylpiperazin-4-yl)-2-hydroxypropyl, 3-(N,N-diethylamino)-2-hydroxypropyl, (2R)-3-(N,N-diethylamino)-2-hydroxypropyl, (2S)-3-(N,N-diethylamino)-2-hydroxypropyl, 3-(isopropylamino)-2-hydroxypropyl, (2R)-3-(isopropylamino)-2-hydroxypropyl, (2S)-3-(isopropylamino)-2-hydroxypropyl, 3-(N,N-diisopropylamino)-2-hydroxypropyl, (2R)-3-(N,N-diisopropylamino)-2-hydroxypropyl or (2S)-3-(N,N-diisopropylamino)-2-hydroxypropyl].

Particularly $R^2$ represents $C_{1-3}$alkyl, amino or $R^5X^1$— [wherein $X^1$ is as hereinbefore defined and $R^5$ represents ethyl, benzyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(ethylsulphinyl)ethyl, 2-(ethylsulphonyl)ethyl, 2-(N,N-dimethylsulphamoyl)ethyl, 2-(N-methylsulphamoyl)ethyl, 2-sulphamoylethyl, 2-(methylamino)ethyl, 3-(methylamino)propyl, 2-(ethylamino)ethyl, 3-(ethylamino)propyl, 2-(N,N-dimethylamino)ethyl, 3-(N,N-dimethylamino)propyl, 2-(N,N-diethylamino)ethyl, 3-(N,N-diethylamino)propyl, 2-(N-methyl-N-methylsulphonylamino)ethyl, 3-N-methyl-N-methylsulphonylamino)propyl, 2-morpholinoethyl, 3-morpholinopropyl, 2-piperidinoethyl, 3-piperidinopropyl, 2-(methylpiperidino)ethyl, 3-(methylpiperidino)propyl, 2-(ethylpiperidino)ethyl, 3-(ethylpiperidino)propyl, 2-((2-methoxyethyl)piperidino)ethyl, 3-((2-methoxyethyl)piperdino)propyl, 2-((2-methylsulphonyl)ethylpiperidino)ethyl, 3-((2-methylsulphonyl)ethylpiperidino)propyl, piperidin-3-ylmethyl, piperidin-4-ylmethyl, 2-(piperidin-3-yl)ethyl, 2-(piperidin-4-yl)ethyl, 3-(piperidin-3-yl)propyl, 3-(piperidin-4-yl)propyl, 2-(piperidin-2-yl)ethyl, 3-(piperidin-2-yl)propyl, (1-methylpiperidin-3-yl)methyl, (1-methylpiperidin-4-yl)methyl, 2-(4-hydroxypiperidino)ethyl, 3-(4-hydroxypiperidino)propyl, (1-cyanomethylpiperidin-3-yl)methyl, (1-cyanomethylpiperidin-4-yl)methyl, 2-(methylpiperidin-3-yl)ethyl, 2-(methylpiperidin-4-yl)ethyl, 2-(1-cyanomethylpiperidin-3-yl)ethyl, 2-(1-cyanomethylpiperidin-4-yl)ethyl, 3-(methylpiperidin-3-yl)propyl, 3-(methylpiperidin-4-yl)propyl, 3-(1-cyanomethylpiperidin-3-yl)propyl, 3-(1-cyanomethylpiperidin-4-yl)propyl, 2-(ethylpiperidin-3-yl)ethyl, 2-(ethylpiperidin-4-yl)ethyl, 3-(ethylpiperidin-3-yl)propyl, 3-(ethylpiperidin-4-yl)propyl, ((2-methoxyethyl)piperidin-3-yl)methyl, ((2-methoxyethyl)piperidin-4-yl)methyl, 2-((2-methoxyethyl)piperidin-3-yl)ethyl, 2-((2-methoxyethyl)piperidin-4-yl)ethyl, 3-((2-methoxyethyl)piperidin-3-yl)propyl-3-((2-methoxyethyl)piperidin-4-yl)propyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 1-isopropylpiperidin-2-ylmethyl, 1-isopropylpiperidin-3-ylmethyl, 1-isopropylpiperidin-4-ylmethyl, 2-(1-isopropylpiperidin-2-yl)ethyl, 2-(1-isopropylpiperidin-3-yl)ethyl, 2-(1-isopropylpiperidin-4-yl)ethyl, 3-(1-isopropylpiperidin-2-yl)propyl, 3-(1-isopropylpiperidin-3-yl)propyl, 3-(1-isopropylpiperidin-4-yl)propyl, 2-(piperidin-4-yloxy)ethyl, 3-(piperidin-4-yloxy)propyl, 2-(1-(cyanomethyl)piperidin-4-yloxy)ethyl, 3-(1-(cyanomethyl)piperidin-4-yloxy)propyl, 2-(1-(2-cyanoethyl)piperidin-4-yloxy)ethyl, 3-(1-(2-cyanoethyl)piperidin-4-yloxy)propyl, 2-(piperazin-1-yl)ethyl, 3-(piperazin-1-yl)propyl, (pyrrolidin-2-yl)methyl, 2-(pyrrolidin-1-yl)ethyl, 3-(pyrrolidin-1-yl)propyl, (2-oxo-tetrahydro-2H-pyrrolidin-5-yl)methyl, 5(R)-(2-oxo-tetrahydro-2H-pyrrolidin-5-yl)methyl, (5S-(2-oxo-tetrahydro-2H-pyrrolidin-5-yl)methyl, (1,3-dioxolan-2-yl)methyl, 2-(1,3-dioxolan-2-yl)ethyl, 2-(2-methoxyethylamino)ethyl, 2-(N-(2-methoxyethyl)-N-methylamino)

ethyl, 2-(2-hydroxyethylamino)ethyl, 3-(2-methoxyethylamino)propyl, 3-(N-(2-methoxyethyl)-N-methylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(2-methylimidazol-1-yl)ethyl, 2-(2-ethylimidazol-1-yl)ethyl, 3-(2-methylimidazol-1-yl)propyl, 3-(2-ethylimidazol-1-yl)propyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 3-pyridylmethyl, 2-(3-pyridyl)ethyl, 3-(3-pyridyl)propyl, 2-(4-pyridyloxy)ethyl, 2-(4-pyridylamino)ethyl, 2-(4-oxo-1,4-dihydro-1-pyridyl)ethyl, 2-(2-oxo-imidazolidin-1-yl)ethyl, 3-(2-oxo-imidazolidin-1-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 2-(4-cyanomethylpiperazin-1-yl)ethyl, 3-(4-cyanomethylpiperazin-1-yl)propyl, 2-(4-acetylpiperazin-1-yl)ethyl, 3-(4-acetylpiperazin-1-yl)propyl, 2-(4-methylsulphonylpiperazin-1-yl)ethyl, 3-(4-methylsulphonylpiperazin-1-yl)propyl, 3-(methylsulphinyl)propyl, 3-(methylsulphonyl)propyl, 3-(ethylsulphinyl)propyl, 3-(ethylsulphonyl)propyl, 2-(5-methyl-1,2,4-triazol-1-yl)ethyl, morpholino, 2-((N-(1-methylimidazol-4-ylsulphonyl)-N-methyl)amino)ethyl, 2-((N-(3-morpholinopropylsulphonyl)-N-methyl)amino)ethyl, 2-((N-methyl-N-4-pyridyl)amino)ethyl, 3-(4-oxidomorpholino)propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2-((2-(pyrrolidin-1-yl)ethyl)carbamoyl)vinyl, 3-((2-(pyrrolidin-1-yl)ethyl)carbamoyl)prop-2-en-1-yl, 1-(2-pyrrolidinylethyl)piperidin-4-ylmethyl, 1-(3-pyrrolidinylpropyl)piperidin-4-ylmethyl, 1-(2-piperidinylethyl)piperidin-4-ylmethyl, 1-(3-piperidinylpropyl)piperidin-4-ylmethyl, 1-(2-morpholinoethyl)piperidin-4-ylmethyl, 1-(3-morpholinopropyl)piperidin-4-ylmethyl, 1-(2-thiomorpholinoethyl)piperidin-4-ylmethyl, 1-(3-thiomorpholinopropyl)piperidin-4-ylmethyl, 1-(2-azetidinylethyl)piperidin-4-ylmethyl, 1-(3-azetidinylpropyl)piperidin-4-ylmethyl, 2-(1-(2-pyrrolidinylethyl)piperidin-4-yl)ethyl, 2-(1-(3-pyrrolidinylpropyl)piperidin-4-yl)ethyl, 2-(1-(2-piperidinylethyl)piperidin-4-yl)ethyl, 2-(1-(3-piperidinylpropyl)piperidin-4-yl)ethyl, 2-(1-(2-morpholinoethyl)piperidin-4-yl)ethyl, 2-(1-(3-morpholinopropyl)piperidin-4-yl)ethyl, 2-(1-(2-thiomorpholinoethyl)piperidin-4yl)ethyl, 2-(1-(3thiomorpholinopropyl)piperidin-4-yl)ethyl, 2-(1-(2-azetidinylethyl)piperidin-4-yl)ethyl, 2-(1-(3-azetidinylpropyl)piperidin-4-yl)ethyl, 3-morpholino-2-hydroxypropyl, (2R)-3-morpholino-2-hydroxypropyl, (2S)-3-morpholino-2-hydroxypropyl, 3-piperidino-2-hydroxypropyl, (2R)-3-piperidino-2-hydroxypropyl, (2S)-3-piperidino-2-hydroxypropyl, 3-pyrrolidin-1-yl-2-hydroxypropyl, (2R)-3-pyrrolidin-1-yl-2-hydroxypropyl, (2S)-3-pyrrolidin-1-yl-2-hydroxypropyl, 3-(1-methylpiperazin-4-yl)-2-hydroxypropyl, (2R)-3-(1-methylpiperazin-4-yl)-2-hydroxypropyl, (2S)-3-(1-methylpiperazin-4-yl)-2-hydroxypropyl, 3-(N,N-diethylamino)-2-hydroxypropyl, (2R)-3-(N,N-diethylamino)-2-hydroxypropyl, (2S)-3-N,N-diethylamino)-2-hydroxypropyl, 3-(isopropylamino)-2-hydroxypropyl, (2R)-3-(isopropylamino)-2-hydroxypropyl, (2S)-3-(isopropylamino)-2-hydroxypropyl, 3-(N,N-diisopropylamino)-2-hydroxypropyl, (2R)-3-(N,N-diisopropylamino)-2-hydroxypropyl or (2S)-3-(N,N-diisopropylamino)-2-hydroxypropyl].

More particularly $R^2$ represents $C_{1-3}$alkyl, amino or $R^5X^1—$ [wherein $X^1$ is as hereinbefore defined and $R^5$ represents ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(ethylsulphinyl)ethyl, 2-(ethylsulphonyl)ethyl, 2-(N,N-dimethylsulphamoyl)ethyl, 2-(N-methylsulphamoyl)ethyl, 2-sulphamoylethyl, 2-(methylamino)ethyl, 3-(methylamino)propyl, 2-(ethylamino)ethyl, 3-(ethylamino)propyl, 2-(N,N-dimethylamino)ethyl, 3-(N,N-dimethylamino)propyl, 2-(N,N-diethylamino)ethyl, 3-(N,N-diethylamino)propyl, 2-(N-methyl-N-methylsulphonylamino)ethyl, 3-(N-methyl-N-methylsulphonylamino)propyl, 2-morpholinoethyl, 3-morpholinopropyl, 2-piperidinoethyl, 3-piperidinopropyl, 2-(methylpiperidino)ethyl, 3-(methylpiperidino)propyl, 2-(ethylpiperidino)ethyl, 3-(ethylpiperidino)propyl, 2-((2-methoxyethyl)piperidino)ethyl, 3-((2-methoxyethyl)piperidino)propyl, 2-((2-methylsulphonyl)ethylpiperidino)ethyl, 3-((2-methylsulphonyl)ethylpiperidino)propyl, piperidin-3-ylmethyl, piperidin-4-ylmethyl, 2-(piperidin-3-yl)ethyl, 2-(piperidin-4-yl)ethyl, 3-(piperidin-3-yl)propyl, 3-(piperidin-4-yl)propyl, 2-(piperidin-2-yl)ethyl, 3-(piperidin-2-yl)propyl, (1-methylpiperidin-3-yl)methyl, (1-methylpiperidin-4-yl)methyl, 2-(4-hydroxypiperidino)ethyl, 3-(4-hydroxypiperidino)propyl, (1-cyanomethylpiperidin-3-yl)methyl, (1-cyanomethylpiperidin-4-yl)methyl, 2-(methylpiperidin-3-yl)ethyl, 2-(methylpiperidin-4-yl)ethyl, 2-(1-cyanomethylpiperidin-3-yl)ethyl, 2-(1-cyanomethylpiperidin-4-yl)ethyl, 3-(methylpiperidin-3-yl)propyl, 3-(methylpiperidin-4-yl)propyl, 3-(1-cyanomethylpiperidin-3-yl)propyl, 3-(1-cyanomethylpiperidin-4-yl)propyl, 2-(ethylpiperidin-3-yl)ethyl, 2-(ethylpiperidin-4-yl)ethyl, 3-(ethylpiperidin-3-yl)propyl, 3-(ethylpiperdin-4-yl)propyl, ((2-methoxyethyl)piperidin-3-yl)methyl, ((2-methoxyethyl)piperidin-4-yl)methyl, 2-((2-methoxyethyl)piperidin-3-yl)ethyl, 2-((2-methoxyethyl)piperidin-4-yl)ethyl, 3-((2-methoxyethyl)piperidin-3-yl)propyl, 3-((2-methoxyethyl)piperidin-4-yl)propyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4yl)ethyl, 3-((2-methylsulphonylethyl)piperidin-3-yl)propyl, 3-((2-methylsulphonylethyl)piperidin-4-yl)propyl, 1-isopropylpiperidin-2-ylmethyl, 1-isopropylpiperidin-3-ylmethyl, 1-isopropylpiperidin-4-ylmethyl, 2-(1-isopropylpiperidin-2-yl)ethyl, 2-(1-isopropylpiperidin-3-yl)ethyl, 2-(1-isopropylpiperidin-4-yl)ethyl, 3-(1-isopropylpiperidin-2-yl)propyl, 3-(1-isopropylpiperidin-3-yl)propyl, 3-(1-isopropylpiperidin-4-yl)propyl, 2-(piperidin-4-yloxy)ethyl, 3-(piperidin-4-yloxy)propyl, 2-(1-(cyanomethyl)piperidin-4-yloxy)ethyl, 3-(1-(cyanomethyl)piperidin-4-yloxy)propyl, 2-(1-(2-cyanoethyl)piperidin-4-yloxy)ethyl, 3-(1-(2-cyanoethyl)piperidin-4-yloxy)propyl, 2-(piperaziny-1-yl)ethyl, 3-(piperazin-1-yl)propyl, (pyrrolidin-2-yl)methyl, 2-(pyrrolidin-1-yl)ethyl, 3-(pyrrolidin-1-yl)propyl, (2-oxo-tetrahydro-2H-pyrrolidin-5-yl)methyl, 5(R)-(2-oxo-tetrahydro-2H-pyrrolidin-5-yl)methyl, (5S)-(2-oxo-tetrahydro-2H-pyrrolidin-5-yl)methyl, (1,3-dioxolan-2-yl)methyl, 2-(1,3-dioxolan-2-yl)ethyl, 2-(2-methoxyethylamino)ethyl, 2-(N-(2-methoxyethyl)-N-methylamino)ethyl, 2-(2-hydroxyethylamino)ethyl, 3-(2-methoxyethylamino)propyl, 3-(N-(2-methoxyethyl)-N-methylamino)propyl, 3-(2-hydroxyethylamino)propyl, 2-(1,2,3-triazol-1-yl)ethyl, 2-(1,2,3-triazol-2-yl)ethyl, 2-(1,2,4- triazol-1-yl)ethyl, 2-(1,2,4-triazol-4-yl)ethyl, 4-pyridylmethyl, 2-(4-pyridyl)ethyl, 3-(4-pyridyl)propyl, 3-pyridylmethyl, 2-(3-pyridyl)ethyl, 3-(3-pyridyl)propyl, 2-(4-pyridyloxy)ethyl, 2-(4-pyridylamino)ethyl, 2-(4-oxo-1,4-dihydro-1-pyridyl)ethyl, 2-(2-oxo-imidazolidin-1-yl)ethyl, 3-(2-oxo-imidazolidin-1-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 2-(4-cyanomethylpiperazin-1-yl)ethyl, 3-(4-cyanomethylpiperazin-1-yl)propyl, 2-(4-acetylpiperazin-1-yl)ethyl, 3-(4-acetylpiperazin-1-yl)propyl, 2-(4-methylsulphonylpiperazin-1-yl)ethyl, 3-(4-methylsulphonylpiperazin-1-yl)propyl, 3-(methylsulphinyl)propyl, 3-(methylsulphonyl)propyl, 3-(ethylsulphinyl)propyl, 3-(ethylsulphonyl)propyl, 2-(5-methyl-1,2,4-triazol-1-yl)ethyl, morpholino, 2-(N-(3-morpholinopropylsulphonyl)-N-methyl)amino)ethyl, 2-((N-methyl-N-4-pyridyl)amino)ethyl, 3-(4-oxidomorpholino)propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2-((2-(pyrrolidin-1-yl)ethyl)carbamoyl)vinyl, 3-((2-(pyrrolidin-1-yl)ethyl)carbamoyl)prop-2-en-1-yl, 1-(2-pyrrolidinylethyl)piperidin-4-ylmethyl, 1-(3-pyrrolidinylpropyl)piperidin-4-ylmethyl, 1-(2-piperidinylethyl)piperidin-4-ylmethyl, 1-(3-piperidinylpropyl)piperidin-4-ylmethyl, 1-(2-morpholinoethyl)piperidin-4-ylmethyl, 1-(3-morpholinopropyl)piperidin-4-ylmethyl, 1-(2-thiomorpholinoethyl)piperidin-4-ylmethyl, 1-(3-thiomorpholinopropyl)piperidin-4-ylmethyl, 1-(2-azetidinylethyl)piperidin-4-ylmethyl, 1-(3-azetidinylpropyl)piperidin-4-ylmethyl, 2-(1-(2-pyrrolidinylethyl)piperidin-4-yl)ethyl, 2-(1-(3-pyrrolidinylpropyl)piperidin-4-yl)ethyl, 2-(1-(2-piperidinylethyl)piperidin-4-yl)ethyl, 2-(1-(3-piperidinylpropyl)piperidin-4-yl)ethyl, 2-(1-(2-morpholinoethyl)piperidin-4-yl)ethyl, 2-(1-(3-morpholinopropyl)piperidin-4-yl)ethyl, 2-(1-(2-thiomorpholinoethyl)piperidin-4-yl)ethyl, 2-(1-(3-thiomorpholinopropyl)piperidin-4-yl)ethyl, 2-(1-(2-azetidinylethyl)piperidin-4-yl)ethyl, 2-(1-(3-azetidinylpropyl)piperidin-4-yl)ethyl, 3-morpholino-2-hydroxypropyl, (2R)-3-morpholino-2-hydroxypropyl, (2S)-3-morpholino-2-hydroxypropyl, 3-piperidino-2-hydroxypropyl, (2R)-3-piperidino-2-hydroxypropyl, (2S)-3-piperidino-2-hydroxypropyl, 3-pyrrolidin-1-yl-2-hydroxypropyl, (2R)-3-pyrrolidin-1-yl-2-hydroxypropyl, (2S)-3-pyrrolidin-1-yl-2-hydroxypropyl, 3-(1-methylpiperazin-4-yl)-2-hydroxypropyl, (2R)-3-(1-methylpiperazin-4-yl)-2-hydroxypropyl, (2S)-3-(1-methylpiperazin-4-yl)-2-hydroxypropyl, 3-N,N-diethylamino)-2-hydroxypropyl, (2R)-3-(N,N-diethylamino)-2-hydroxypropyl, (2S)-3-(N,N-diethylamino)-2-hydroxypropyl, 3-(isopropylamino)-2-hydroxypropyl, (2R)-3-(isopropylamino)-2-hydroxypropyl, (2S)-3-(isopropylamino)-2-hydroxypropyl, 3-(N,N-diisopropylamino)-2-hydroxypropyl, (2R)-3-N,N-diisopropylamino)-2-hydroxypropyl or (2S)-3-(N,N-diisopropylamino)-2-hydroxypropyl].

In another aspect $R^2$ represents ethoxy, trifluoromethoxy, 2,2,2-trifluoroethoxy, 2-hydroxyethoxy, 3-hydroxypropoxy, 2-methoxyethoxy, 3-methoxypropoxy, 2-(methylsulphinyl)ethoxy, 2-(methylsulphonyl)ethoxy, 2-(ethylsulphinyl)ethoxy, 2-(ethylsulphonyl)ethoxy, 2-(N,N-dimethylsulphamoyl)ethoxy, 2-(N-methylsulphamoyl)ethoxy, 2-sulphamoylethoxy, 2-(methylamino)ethoxy, 3-(methylamino)propoxy, 2-(ethylamino)ethoxy, 3-(ethylamino)propoxy, 2-(N,N-dimethylamino)ethoxy, 3-(N,N-dimethylamino)propoxy, 2-(N,N-diethylamino)ethoxy, 3-(N,N-diethylamino)propoxy, 2-N-methyl-N-methylsulphonylamino)ethoxy, 3-(N-methyl-N-methylsulphonylamino)propoxy, 2-morpholinoethoxy, 3-morpholinopropoxy, 2-piperidinoethoxy, 3-piperidinopoxy, 2-(methylpiperidino)ethoxy, 3-(methylpiperidino)propoxy, 2-(ethylpiperidino)ethoxy, 3-(ethylpiperidino)propoxy, 2-((2-methoxyethyl)piperidino)ethoxy, 3-((2-methoxyethyl)piperidino)propoxy, 2-((2-methylsulphonyl)ethylpiperidino)ethoxy, 3-((2-methylsulphonyl)ethylpiperidino)propoxy, piperidin-3-ylmethoxy, piperidin-4-ylmethoxy, 2-(piperidin-3-yl)ethoxy, 2-(piperidin-4-yl)ethoxy, 3-(piperidin-3-yl)propoxy, 3-(piperidin-4-yl)propoxy, 2-(piperidin-2-yl)ethoxy, 3-(piperidin-2-yl)propoxy, (1-methylpiperidin-3-yl)methoxy, (1-methylpiperidin-4-yl)methoxy, 2-(4-hydroxypiperidino)ethoxy, 3-(4-hydroxypiperidino)propoxy, (1-cyanomethylpiperidin-3-yl)methoxy, (1-cyanomethylpiperidin-4-yl)methoxy, 2-(methylpiperidin-3-yl)ethoxy, 2-(methylpiperidin-4-yl)ethoxy, 2-(1-cyanomethylpiperidin-3-yl)ethoxy, 2-(1-cyanomethylpiperidin-4-yl)ethoxy, 3-(methylpiperidin-3-yl)propoxy, 3-(methylpiperidin-4-yl)propoxy, 3-(1-cyanomethylpiperidin-3-yl)propoxy, 3-(1-cyanomethylpiperidin-4-yl)propoxy, 2-(ethylpiperidin-3-yl)ethoxy, 2-(ethylpiperidin-4-yl)ethoxy, 3-(ethylpiperidin-3-yl)propoxy, 3-(ethylpiperidin-4-yl)propoxy, ((2-methoxyethyl)piperidin-3-yl)methoxy, ((2-methoxyethyl)piperidin-4-yl)methoxy, 2-((2-methoxyethyl)piperidin-3-yl)ethoxy, 2-((2-methoxyethyl)piperidin-4-yl)ethoxy, 3-((2-methoxyethyl)piperidin-3-yl)propoxy, 3-((2-methoxyethyl)piperidin-4-yl)propoxy, (1-(2-methylsulphonylethyl)piperidin-3-yl)methoxy, (1-(2-methylsulphonylethyl)piperidin-4-yl)methoxy, 2-((2-methylsulphonylethyl)piperidin-3-yl)ethoxy, 2-((2-methylsulphonylethyl)piperidin-4-yl)ethoxy, 3-((2-methylsulphonylethyl)piperidin-3-yl)propoxy, 3-((2-methylsulphonylethyl)piperidin-4-yl)propoxy, 1-isopropylpiperidin-2-ylmethoxy, 1-isopropylpiperidin-3-ylmethoxy, 1-isopropylpiperidin-4-ylmethoxy, 2-(1-isopropylpiperidin-2-yl)ethoxy, 2-(1-isopropylpiperidin-3-yl)ethoxy, 2-(1-isopropylpiperidin-4-yl)ethoxy, 3-(1-isopropylpiperidin-2-yl)propoxy, 3-(1-isopropylpiperidin-3-yl)propoxy, 3-(1-isopropylpiperidin-4-yl)propoxy, 2-(piperidin-4-yloxy)ethoxy, 3-(piperidin-4-yloxy)propoxy, 2-(1-(cyanomethyl)piperidin-4-yloxy)ethoxy, 3-(1-(cyanomethyl)piperidin-4-yloxy)propoxy, 2-(1-(2-cyanoethyl)piperidin-4-yloxy)ethoxy, 3-(1-(2-cyanoethyl)piperidin-4-yloxy)propoxy, 2-(piperazin-1-yl)ethoxy, 3-(piperazin-1-yl)propoxy, (pyrrolidin-2-yl)methoxy, 2-(pyrrolidin-1-yl)ethoxy, 3-(pyrrolidin-1-yl)propoxy, (2-oxo-tetrahydro-2H-pyrrolidin-5-yl)methoxy, 5(R)-(2-oxo-tetrahydro-2H-pyrrolidin-5-yl)methoxy, (5S)-(2-oxo-tetrahydro-2H-pyrrolidin-5-yl)methoxy, (1,3-dioxolan-2-yl)methoxy, 2-(1,3-dioxolan-2-yl)ethoxy, 2-(2-methoxyethylamino)ethoxy, 2-(N-(2-methoxyethyl)-N-methylamino)ethoxy, 2-(2-hydroxyethylamino)ethoxy, 3-(2-methoxyethylamino)propoxy, 3-(N-(2-methoxyethyl)-N-methylamino)propoxy, 3-(2-hydroxyethylamino)propoxy, 2-(1,2,3-triazol-1-yl)ethoxy, 2-(1,2,3-triazol-2-yl)ethoxy, 2-(1,2,4-triazol-1-yl)ethoxy, 2-(1,2,4-triazol-4-yl)ethoxy, 4-pyridylmethoxy, 2-(4-pyridyl)ethoxy, 3-(4-pyridyl)propoxy, 3-pyridylmethoxy, 2-(3-pyridyl)ethoxy, 3-(3-pyridyl)propoxy, 2-(4-pyridyloxy)ethoxy, 2-(4-pyridylamino)ethoxy, 2-(4-oxo-1,4-dihydro-1-pyridyl)ethoxy, 2-(2-oxo-imidazolidin-1-yl)ethoxy, 3-(2-oxo-imidazolidin-1-yl)propoxy, 2-thiomorpholinoethoxy, 3-thiomorpholinopropoxy, 2-(1,1-dioxothiomorpholino)ethoxy, 3-(1,1-dioxothiomorpholino)propoxy, 2-(2-methoxyethoxy)ethoxy, 2-(4-methylpiperazin-1-yl)ethoxy, 3-(4-methylpiperazin-1-yl)propoxy, 2-(4-cyanomethylpiperazin-1-yl)ethoxy, 3-(4-cyanomethylpiperazin-1-yl)propoxy, 2-(4-acetylpiperazin-1-yl)ethoxy, 3-(4-acetylpiperazin-1-yl)propoxy, 2-(4-methylsulphonylpiperazin-1-yl)ethoxy, 3-(4-methylsulphonylpiperazin-1-yl)propoxy, 3-(methylsulphinyl)propoxy, 3-(methylsulphonyl)propoxy, 3-(ethylsulphinyl)propoxy, 3-(ethylsulphonyl)propoxy, 2-(5-methyl-1,2,4-triazol-1-yl)ethoxy, 2-(N-(3-morpholinopropylsulphonyl)-N-methyl)amino)ethoxy, 2-(N-methyl-N-4-pyridyl)amino)ethoxy, 3-(4-oxidomorpholino)propoxy, 2-(2-(4-methylpiperazin-1-yl)ethoxy)ethoxy, 3-(2-(4-methylpiperazin-1-yl)ethoxy)propoxy, 2-(2-morpholinoethoxy)ethoxy, 3-(2-morpholinoethoxy)propoxy, 2-(tetrahydropyran-4-yloxy)ethoxy, 3-(tetrahydropyran-4-yloxy)propoxy, 2-((2-(pyrrolidin-1-yl)ethyl)carbamoyl)vinyl, 3-((2-(pyrrolidin-1-yl)ethyl)carbamoyl)prop-2-en-1-yloxy, 1-(2-pyrrolidinylethyl)piperidin-4-ylmethoxy, 1-(3-pyrrolidinylpropyl)piperidin-4-ylmethoxy, 1-(2-piperidinylethyl)piperidin-4-ylmethoxy, 1-(3-piperidinylpropyl)piperidin-4-ylmethoxy, 1-(2-morpholinoethyl)piperidin-4-ylmethoxy, 1-(3-morpholinopropyl)piperidin-4-ylmethoxy, 1-(2-thiomorpholinoethyl)piperidin-4-ylmethoxy, 1-(3-thiomorpholinopropyl)piperidin-4-ylmethoxy, 1-(2-azetidinylethyl)piperidin-4-ylmethoxy, 1-(3-azetidinylpropyl)piperidin-4-ylmethoxy, 2-(1-(2-pyrrolidinylethyl)piperidin-4-yl)ethoxy, 2-(1-(3-pyrrolidinylpropyl)piperidin-4-yl)ethoxy, 2-(1-(2-piperidinylethyl)piperidin-4-yl)ethoxy, 2-(1-(3-piperidinylpropyl)piperidin-4-yl)ethoxy, 2-(1-(2-morpholinoethyl)piperidin-4-yl)ethoxy, 2-(1-(3-morpholinopropyl)piperidin-4-yl)ethoxy, 2-(1-(2-thiomorpholinoethyl)piperidin-4-yl)ethoxy, 2-(1-(3-thiomorpholinopropyl)piperidin-4-yl)ethoxy, 2-(1-(2-azetidinylethyl)piperidin-4-yl)ethoxy, 2-(1-(3-azetidinylpropyl)piperidin-4-yl)ethoxy, 3-morpholino-2-hydroxypropoxy, (2R)-3-morpholino-2-hydroxypropoxy, (2S)-3-morpholino-2-hydroxypropoxy, 3-piperidino-2-hydroxypropoxy, (2R)-3-piperidino-2-hydroxypropoxy, (2S)-3-piperidino-2-hydroxypropoxy, 3-pyrrolidin-1-yl-2-hydroxypropoxy, (2R)-3-pyrrolidin-1-yl-2-hydroxypropoxy, (2S)-3-pyrrolidin-1-yl-2-hydroxypropoxy, 3-(1-methylpiperazin-4-yl)-2-hydroxypropoxy, (2R)-3-(1-methylpiperazin-4-yl)-2-hydroxypropoxy, (2S)-3-(1-methylpiperazin-4-yl)-2-hydroxypropoxy, 3-(N,N-diethylamino)-2-hydroxypropoxy, (2R)-3-(N,N-diethylamino)-2-hydroxypropoxy, (2S)-3-(N,N-diethylamino)-2-hydroxypropoxy, 3-(isopropylamino)-2-hydroxypropoxy, (2R)-3-(isopropylamino)-2-hydroxypropoxy, (2S)-3-(isopropylamino)-2-hydroxypropoxy, 3-(N,N-diisopropylamino)-2-hydroxypropoxy, (2R)-3-(N,N-diisopropylamino)-2-hydroxypropoxy or (2S)-3-(N,N-diisopropylamino)-2-hydroxypropoxy.

According to another aspect of the present invention conveniently $R^2$ represents hydroxy, halogeno, cyano, nitro, trifluoromethyl, $C_{1-3}$alkyl, amino or $R^5X^1$— [wherein $X^1$ is as hereinbefore defined and $R^5$ is selected from one of the following twenty-two groups:

1) oxiranyl$C_{1-4}$alkyl or $C_{1-5}$alkyl which may be unsubstituted or which may be substituted with one or more groups selected from fluoro, chloro and bromo, or $C_{2-5}$alkyl which may be unsubstituted or substituted with one or more groups selected from hydroxy and amino;
2) $C_{2-3}$alkyl$X^2$C(O)$R^{11}$ (wherein $X^2$ is as hereinbefore defined and $R^{11}$ represents $C_{1-3}$alkyl, —N$R^{13}R^{14}$ or —O$R^{15}$ (wherein $R^{13}$, $R^{14}$ and $R^{15}$ which maybe the same or different are each $C_{1-4}$alkyl or $C_{1-2}$alkoxyethyl));
3) $C_{2-4}$alkyl$X^3R^{16}$ (wherein $X^3$ is as hereinbefore defined and $R^{16}$ represents hydrogen, $C_{1-3}$alkyl, cyclopentyl, cyclohexyl or a 4-, 5- or 6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-3}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl));
4) $C_{2-3}$alkyl$X^4C_{2-3}$alkyl$X^5R^{22}$ (wherein $X^4$ and $X^5$ are as hereinbefore defined and $R^{22}$ represents hydrogen or $C_{1-3}$alkyl);
5) $R^{28}$ (wherein $R^{28}$ is as defined hereinbefore);
6) $C_{1-5}$alkyl$R^{56}$ (wherein $R^{56}$ is a 4-, 5- or 6-membered saturated heterocyclic group with 1–2 heteroatoms, selected independently from O, S and N, which heterocyclic group is linked to $C_{1-5}$alkyl through a carbon atom and which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl)) or $C_{2-5}$alkyl$^{57}$ (wherein $R^{57}$ is a 4-, 5- or 6-membered saturated heterocyclic group with 1–2 heteroatoms, of which one is N and the other may be selected independently from O, S and N, which heterocyclic group is linked to $C_{2-5}$alkyl through a nitrogen atom and which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl));
7) $C_{3-4}$alkenyl$R^{58}$ (wherein $R^{58}$ represents $R^{56}$ or $R^{57}$ as defined hereinbefore);
8) $C_{3-4}$alkynyl$R^{58}$ (wherein $R^{58}$ represents $R^{56}$ or $R^{57}$ as defined hereinbefore);
9) $R^{29}$ (wherein $R^{29}$ is as defined hereinbefore);
10) $C_{1-5}$alkyl$R^{29}$ (wherein $R^{29}$ is as defined hereinbefore);
11) $C_{3-5}$alkenyl$R^{29}$ (wherein $R^{29}$ is as defined hereinbefore);
12) $C_{3-5}$alkynyl$R^{29}$ (wherein $R^{29}$ is as defined hereinbefore);
13) $C_{1-5}$alkyl$X^6R^{29}$ (wherein $X^6$ and $R^{29}$ are as defined hereinbefore);
14) $C_{4-5}$alkenyl$X^7R^{29}$ (wherein $X^7$ and $R^{29}$ are as defined hereinbefore);

15) $C_{4-5}$alkynylX$^8$R$^{29}$ (wherein X$^8$ and R$^{29}$ are as defined hereinbefore);
16) $C_{2-3}$alkylX$^9$C$_{1-3}$alkylR$^{29}$ (wherein X$^9$ and R$^{29}$ are as defined hereinbefore);
17) $C_{2-3}$alkylX$^9$C$_{1-3}$alkylR$^{28}$ (wherein X$^9$ and R$^{28}$ are as defined hereinbefore);
18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;
19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;
20) $C_{2-5}$alkenylX$^9$C$_{1-3}$alkylR$^{28}$ (wherein X$^9$ and R$^{28}$ are as defined hereinbefore);
21) $C_{2-5}$alkynylX$^9$C$_{1-3}$alkylR$^{28}$ (wherein X$^9$ and R$^{28}$ are as defined hereinbefore); and
22) $C_{1-3}$alkyl$^{54}$(C$_{1-3}$alkyl)$_q$(X$^9$)$_r$R$^{55}$ (wherein X$^9$, q, r, R$^{54}$ and R$^{55}$ are as defined hereinbefore);

and additionally wherein any $C_{1-5}$alkyl, $C_{2-5}$alkenyl or $C_{2-5}$alkynyl group in R$^5$X$^1$— may bear one or more substituents selected from hydroxy, halogeno and amino].

According to another aspect of the present invention advantageously R$^2$ represents hydroxy, halogeno, cyano, nitro, trifluoromethyl, $C_{1-3}$alkyl, amino or R$^5$X$^1$— [wherein X$^1$ is as hereinbefore defined and R$^5$ is selected from one of the following twenty-two groups:

1) $C_{1-4}$alkyl which may be unsubstituted or which may be substituted with one or more groups selected from fluoro, chloro and bromo, or $C_{2-5}$alkyl which may be unsubstituted or substituted with one or more groups selected from hydroxy and amino;
2) $C_{2-3}$alkylX$^2$C(O)R$^{11}$ (wherein X$^2$ is as hereinbefore defined and R$^{11}$ represents —NR$^{13}$R$^{14}$ or —OR$^{15}$ (wherein R$^{13}$, R$^{14}$ and R$^{15}$ which may be the same or different are each $C_{1-4}$alkyl or $C_{1-2}$alkoxyethyl));
3) $C_{2-1}$alkylX$^3$R$^{16}$ (wherein X$^3$ is as hereinbefore defined and R$^{16}$ is a group selected from $C_{1-3}$alkyl, cyclopentyl, cyclohexyl, pyrrolidinyl, piperazinyl, piperidinyl, imidazolidinyl, azetidinyl and tetrahydropyranyl, which $C_{1-3}$alkyl group may bear 1 or 2 substituents selected from oxo, hydroxy, halogeno and $C_{1-2}$alkoxy and which cyclopentyl, cyclohexyl, pyrrolidinyl, piperazinyl, piperidinyl, imidazolidinyl, azetidinyl or tetrahydropyranyl group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxyC$_{1-3}$alkyl, $C_{1-2}$alkylsulphonylC$_{1-3}$alkyl, $C_{1-3}$alkoxycarbonyl, $C_{1-3}$alkylamino, di($C_{1-3}$alkyl)amino, $C_{1-3}$alkylaminoC$_{1-3}$alkyl, di($C_{1-3}$alkyl)aminoC$_{1-3}$alkyl, $C_{1-3}$alkylaminoC$_{1-3}$alkoxy, di($C_{1-3}$alkyl)aminoC$_{1-3}$alkoxy and a group —(—O—)$_f$(C$_{1-3}$alkyl)$_g$ring D (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from $C_{1-3}$alkyl));
4) $C_{2-3}$alkylX$^4$C$_{2-3}$alkylX$^5$R$^{22}$ (wherein X$^4$ and X$^5$ are as hereinbefore defined and R$^{22}$ represents hydrogen or $C_{1-3}$alkyl);
5) R$^{28}$ (wherein R$^{28}$ is as defined hereinbefore);
6) $C_{1-4}$alkylR$^{59}$ (wherein R$^{59}$ is a group selected from pyrrolidinyl, piperazinyl, piperidinyl, imidazolidin-1-yl, azetidinyl, 1,3-dioxolan-2-yl, 1,3-dioxan-2-yl, 1,3-dithiolan-2-yl and 1,3-dithian-2-yl, which group is linked to $C_{1-4}$alkyl through a carbon atom and which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxyC$_{1-3}$alkyl, $C_{1-2}$alkylsulphonylC$_{1-3}$alkyl, $C_{1-3}$alkoxycarbonyl, $C_{1-3}$alkylamino, di($C_{1-3}$alkyl)amino, $C_{1-3}$alkylaminoC$_{1-3}$alkyl, di($C_{1-3}$alkyl)aminoC$_{1-3}$alkyl, $C_{1-3}$alkylaminoC$_{1-3}$alkoxy, di($C_{1-3}$alkyl)aminoC$_{1-3}$alkoxy and a group —(—O—)$_f$(C$_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from $C_{1-3}$alkyl)) or $C_{2-4}$alkylR$^{60}$ (wherein R$^{60}$ is a group selected from morpholino, thiomorpholino, azetidin-1-yl, pyrrolidin-1-yl, piperazin-1-yl and piperidino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxyC$_{1-3}$alkyl, $C_{1-2}$alkylsulphonylC$_{1-3}$alkyl, $C_{1-3}$alkoxycarbonyl, $C_{1-3}$alkylamino, di($C_{1-3}$alkyl)amino, $C_{1-3}$alkylaminoC$_{1-3}$alkyl, di($C_{1-3}$alkyl)aminoC$_{1-3}$alkyl, $C_{1-3}$alkylaminoC$_{1-3}$alkoxy, di($C_{1-3}$alkyl)aminoC$_{1-3}$alkoxy and a group —(—O—)$_f$(C$_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from $C_{1-3}$alkyl));
7) $C_{3-4}$alkenylR$^{61}$ (wherein R$^{61}$ represents R$^{59}$ or R$^{60}$ as defined hereinbefore);
8) $C_{3-4}$alkenylR$^{61}$ (wherein R$^{61}$ represents R$^{59}$ or R$^{60}$ as defined hereinbefore);
9) R$^{29}$ (wherein R$^{29}$ is as defined hereinbefore);
10) $C_{1-4}$alkylR$^{29}$ (wherein R$^{29}$ is as defined hereinbefore);
11) 1-R$^{29}$prop-1-en-3-yl or 1-R$^{29}$but-2-en-4-yl (wherein R$^{29}$ is as defined hereinbefore the proviso that when R$^5$ is 1-R$^{29}$prop-1-en-3-yl, R$^{29}$ is linked to the alkenyl group via a carbon atom);
12) 1-R$^{29}$prop-1-yn-3-yl or 1-R$^{29}$but-2-yn-4-yl (wherein R$^{29}$ is as defined hereinbefore with the proviso that when R$^5$ is 1-R$^{29}$prop-1-yn-3-yl, R$^{29}$ is linked to the alkynyl group via a carbon atom);
13) $C_{1-5}$alkylX$^6$R$^{29}$ (wherein X$^6$ and R$^{29}$ are as defined hereinbefore);
14) 1-(R$^{29}$X$^7$)but-2-en-4-yl (wherein X$^7$ and R$^{29}$ are as defined hereinbefore);
15) 1-(R$^{29}$X$^8$)but-2-yn-4-yl (wherein X$^8$ and R$^{29}$ are as defined hereinbefore);
16) $C_{2-3}$alkylX$^9$C$_{1-3}$alkylR$^{29}$ (wherein X$^9$ and R$^{29}$ are as defined hereinbefore);
17) $C_{2-3}$alkylX$^9$C$_{1-3}$alkylR$^{28}$ (wherein X$^9$ and R$^{28}$ are as defined hereinbefore);
18) $C_{2-5}$alkenyl which may be unsubstituted or which may be substituted with one or more fluorine atoms or with one or two groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;
19) $C_{2-5}$alkynyl which may be unsubstituted or which may be substituted with one or more fluorine atoms or with one or two groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;
20) $C_{2-4}$alkenylX$^9$C$_{1-3}$alkylR$^{28}$ (wherein X$^9$ and R$^{28}$ are as defined hereinbefore);

21) $C_{2-4}$alkynyl$X^9C_{1-3}$alkyl$R^{28}$ (wherein $X^9$ and $R^{28}$ are as defined hereinbefore); and
22) $C_{1-3}$alkyl$R^{54}(C_{1-3}$alkyl$)_q(X^9)_rR^{55}$ (wherein $X^9$, q, r, $R^{54}$ and $R^{55}$ are as defined hereinbefore);

and additionally wherein any $C_{1-5}$alkyl, $C_{2-5}$alkenyl or $C_{2-5}$alkynyl group in $R^5X^1$— may bear one or more substituents selected from hydroxy, halogeno and amino].

According to another aspect of the present invention preferably $R^2$ represents hydroxy, halogeno, nitro, trifluoromethyl, $C_{1-3}$alkyl, cyano, amino or $R^5X^1$— [wherein $X^1$ is as hereinbefore defined and $R^5$ is selected from one of the following twenty groups:

1) $C_{1-3}$alkyl which may be unsubstituted or which may be substituted with one or more groups selected from fluoro, chloro and bromo, or $C_{2-3}$alkyl which may be unsubstituted or substituted with one or more groups selected from hydroxy and amino;
2) 2-(3,3-dimethylureido)ethyl, 3-(3,3-dimethylureido)propyl, 2-(3-methylureido)ethyl, 3-(3-methylureido)propyl, 2-ureidoethyl, 3-ureidopropyl, 2-(N,N-dimethylcarbamoyloxy)ethyl, 3-N,N-dimethylcarbamoyloxy)propyl, 2-(N-methylcarbamoyloxy)ethyl, 3-(N-methylcarbamoyloxy)propyl, 2-(carbamoyloxy)ethyl, 3-(carbamoyloxy) propyl, or 2-(-N-methyl-N-(butoxycarbonyl)amino)ethyl;
3) $C_{2-3}$alkyl$X^3R^{16}$ (wherein $X^3$ is as hereinbefore defined and $R^{16}$ is a group selected from $C_{1-3}$alkyl, cyclopentyl, cyclohexyl, pyrrolidinyl, piperidinyl, piperazinyl, azetidinyl, imidazolidinyl and tetrahydropyranyl which group is linked to $X^3$ through a carbon atom and which $C_{1-3}$alkyl group may bear 1 or 2 substituents selected from hydroxy, halogeno and $C_{1-2}$alkoxy and which cyclopentyl, cyclohexyl, pyrrolidinyl, piperidinyl, piperazinyl, azetidinyl, imidazolidinyl or tetrahydropyranyl group may bear one substituent selected from oxo, hydroxy, halogeno, cyano, $C_{1-2}$cyanoalkyl, $C_{1-2}$alkyl, $C_{1-2}$hydroxyalkyl, $C_{1-2}$alkoxy, $C_{1-2}$alkoxy$C_{1-3}$alkyl, $C_{1-2}$alkylsulphonyl$C_{1-3}$alkyl, $C_{1-2}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino));
4) $C_{2-3}$alkyl$X^4C_{2-3}$alkyl$X^5R^{22}$ (wherein $X^4$ and $X^5$ are as hereinbefore defined and $R^{22}$ represents hydrogen or $C_{1-2}$alkyl);
5) $R^{28}$ (wherein $R^{28}$ is as defined hereinbefore);
6) $C_{1-3}$alkyl$R^{59}$ (wherein $R^{59}$ is a group selected from pyrrolidinyl, piperazinyl, piperidinyl, azetidinyl, imidazolidinyl, 1,3-dioxolan-2-yl, 1,3-dioxan-2-yl, 1,3-dithiolan-2-yl and 1,3-dithian-2-yl, which group is linked to $C_{1-3}$alkyl through a carbon atom and which group may bear 1 or 2 substituents selected from oxo, hydroxy, halogeno, cyano, $C_{1-2}$cyanoalkyl, $C_{1-2}$alkyl, $C_{1-2}$hydroxyalkyl, $C_{1-2}$alkoxy, $C_{1-2}$alkoxyl$C_{1-3}$alkyl, $C_{1-2}$alkylsulphonyl$C_{1-3}$alkyl, $C_{1-2}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino)) or $C_{2-3}$alkyl$R^{60}$ (wherein $R^{60}$ is a group selected from morpholino, thiomorpholino, azetidin-1-yl, pyrrolidin-1-yl, piperazin-1-yl and piperidino which group may bear 1 or 2 substituents selected from oxo, hydroxy, halogeno, cyano, $C_{1-2}$cyanoalkyl, $C_{1-2}$alkyl, $C_{1-2}$hydroxyalkyl, $C_{1-2}$alkoxy, $C_{1-2}$alkoxy$C_{1-3}$alkyl, $C_{1-2}$alkylsulphonyl$C_{1-3}$alkyl, $C_{1-2}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino));
7) $R^{29}$ (wherein $R^{29}$ is as defined hereinbefore);
8) $C_{1-4}$alkyl$^{29}$ (wherein $R^{29}$ is as defined hereinbefore);
9) 1-$R^{29}$but-2-en-4-yl (wherein $R^{29}$ is as defined hereinbefore);
10) 1-$R^{29}$but-2-yn-4-yl (wherein $R^{29}$ is as defined hereinbefore);
11) $C_{1-3}$alkyl$X^6R^{29}$ (wherein $X^6$ and $R^{29}$ are as defined hereinbefore);
12) 1-($^{29}X^7$)but-2-en-4-yl (wherein $X^7$ and $R^{29}$ are as defined hereinbefore);
13) 1-($R^{29}X^8$)but-2-yn-4-yl (wherein $X^8$ and $R^{29}$ are as defined hereinbefore);
14) $C_{2-3}$alkyl$X^9C_{1-3}$alkyl$R^{29}$ (wherein $X^9$ and $R^{29}$ are as defined hereinbefore);
15) $C_{2-3}$alkyl$X^9C_{1-3}$alkyl$R^{28}$ (wherein $X^9$ and $R^{28}$ are as defined hereinbefore);
16) $C_{2-5}$alkenyl which may be unsubstituted or which may be substituted with one or more fluorine atoms or with one or two groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;
17) $C_{2-5}$alkynyl which may be unsubstituted or which may be substituted with one or more fluorine atoms or with one or two groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;
18) $C_{2-3}$alkenyl$X^9C_{1-3}$alkyl$R^{28}$ (wherein $X^9$ and $R^{28}$ are as defined hereinbefore);
19) $C_{2-3}$alkynyl$X^9C_{1-3}$alkyl$R^{28}$ (wherein $X^9$ and $R^{28}$ are as defined hereinbefore); and
20) $C_{1-3}$alkyl$R^{54}(C_{1-3}$alkyl$)_q(X^9)_rR^{55}$ (wherein $X^9$, q, r, $R^{54}$ and $R^{55}$ are as defined hereinbefore);

and additionally wherein any $C_{1-5}$alkyl, $C_{2-5}$alkenyl or $C_{2-5}$alkynyl group in $R^5X^1$— may bear one or more substituents selected from hydroxy, halogeno and amino].

According to another aspect of the present invention more preferably $R^2$ represents hydroxy, $C_{1-3}$alkyl, amino or $R^5X^1$— [wherein $X^1$ is as hereinbefore defined and $R^5$ represents methyl, ethyl, benzyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(ethylsulphinyl)ethyl, 2-(ethylsulphonyl)ethyl, 2-(N,N-dimethylsulphamoyl)ethyl, 2-(N-methylsulphamoyl)ethyl, 2-sulphamoylethyl, 2-(methylamino)ethyl, 3-(methylamino)propyl, 2-(ethylamino) ethyl, 3-(ethylamino)propyl, 2-(N,N-dimethylamino)ethyl, 3-(N,N-dimethylamino)propyl, 2-(N,N-diethylamino)ethyl, 3-(N,N-diethylamino)propyl, 2-(N-methyl-N-methylsulphonylamino)ethyl, 3-(N-methyl-N-methylsulphonylamino) propyl, 2-morpholinoethyl, 3-morpholinopropyl, 2-piperidinoethyl, 3-piperidinopropyl, 2-(methylpiperidino)ethyl, 3-(methylpiperidino)propyl, 2-(ethylpiperidino)ethyl, 3-(ethylpiperidino)propyl, 2-((2-methoxyethyl)piperidino) ethyl, 3-((2-methoxyethyl)piperidino)propyl, 2-((2-methylsulphonyl)ethylpiperidino)ethyl, 3-((2-methylsulphonyl)

ethylpiperidino)propyl, piperidin-3-ylmethyl, piperidin-4-ylmethyl, 2-(piperidin-3-yl)ethyl, 2-(piperidin-4-yl)ethyl, 3-(piperidin-3-yl)propyl, 3-(piperidin-4-yl)propyl, 2-(piperidin-2-yl)ethyl, 3-(piperidin-2-yl)propyl, (1-methylpiperidin-3-yl)methyl, (1-methylpiperidin-4-yl)methyl, (1-cyanomethylpiperidin-3-yl)methyl, (1-cyanomethylpiperidin-4-yl)methyl, 2-(methylpiperidin-3-yl)ethyl, 2-(methylpiperidin-4-yl)ethyl, 2-(1-cyanomethylpiperidin-3-yl)ethyl, 2-(1-cyanomethylpiperidin-4-yl)ethyl, 3-(methylpiperidin-3-yl)propyl, 3-(methylpiperidin-4-yl)propyl, 3-(1-cyanomethylpiperidin-3-yl)propyl, 3-(1-cyanomethylpiperidin-4-yl)propyl, 2-(ethylpiperidin-3-yl)ethyl, 2-(ethylpiperidin-4-yl)ethyl, 3-(ethylpiperidin-3-yl)propyl, 3-(ethylpiperidin-4-yl)propyl, ((2-methoxyethyl)piperidin-3-yl)methyl, ((2-methoxyethyl)piperidin-4-yl)methyl, 2-((2-methoxyethyl)piperidin-3-yl)ethyl, 2-((2-methoxyethyl)piperidin-4-yl)ethyl, 3-((2-methoxyethyl)piperidin-3-yl)propyl, 3-((2-methoxyethyl)piperidin-4-yl)propyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 1-isopropylpiperidin-2-ylmethyl, 1-isopropylpiperidin-3-ylmethyl, 1-isopropylpiperidin-4-ylmethyl, 2-(1-isopropylpiperidin-2-yl)ethyl, 2-(1-isopropylpiperidin-3-yl)ethyl, 2-(1-isopropylpiperidin-4-yl)ethyl, 3-(1-isopropylpiperidin-2-yl)propyl, 3-(1-isopropylpiperidin-3-yl)propyl, 3-(1-isopropylpiperidin-4-yl)propyl, 2-(piperidin-4-yloxy)ethyl, 3-(piperidin-4-yloxy)propyl, 2-(1-(cyanomethyl)piperidin-4-yloxy)ethyl, 3-(1-(cyanomethyl)piperidin-4-yloxy)propyl, 2-(1-(2-cyanoethyl)piperidin-4-yloxy)ethyl, 3-(1-(2-cyanoethyl)piperidin-4-yloxy)propyl, 2-(piperazin-1-yl)ethyl, 3-(piperazin-1-yl)propyl, (pyrrolidin-2-yl)methyl, 2-(pyrrolidin 1-yl)ethyl, 3-(pyrrolidin-1-yl)propyl, (2-oxo-tetrahydro-2H-pyrrolidin-5-yl)methyl, 5(R)-(2-oxo-tetrahydro-2H-pyrrolidin-5-yl)methyl, (5S)-(2-oxo-tetrahydro-2H-pyrrolidin-5-yl)methyl, (1,3-dioxolan-2-yl)methyl, 2-(1,3-dioxolan-2-yl)ethyl, 2-(2-methoxyethylamino)ethyl, 2-(N-(2-methoxyethyl)-N-methylamino)ethyl, 2-(2-hydroxyethylamino)ethyl, 3-(2-methoxyethylamino)propyl, 3-(N-(2-methoxyethyl)-N-methylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(2-methylimidazol-1-yl)ethyl, 2-(2-ethylimidazol-1-yl)ethyl, 3-(2-methylimidazol-1-yl)propyl, 3-(2-ethylimidazol-1-yl)propyl, 2-(1,2,3-triazol-1-yl)ethyl, 2-(1,2,3-triazol-2-yl)ethyl, 2-(1,2,4-triazol-1-yl)ethyl, 2-triazol-4-yl)ethyl, 4-pyridylmethyl, 2-(4-pyridyl)ethyl, 3-(4-pyridyl)propyl, 2-(4-pyridyloxy)ethyl, 2-(4-pyridylamino)ethyl, 2-(4-oxo-1,4-dihydro-1-pyridyl)ethyl, 2-(2-oxo-imidazolidin-1-yl)ethyl, 3-(2-oxo-imidazolidin-1-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 3-(methylsulphinyl)propyl, 3-(methylsulphonyl)propyl, 3-(ethylsulphinyl)propyl, 3-(ethylsulphonyl)propyl, 2-(5-methyl-1,2,4-triazol-1-yl)ethyl, morpholino, 2-((N-(1-methylimidazol-4-ylsulphonyl)-N-methyl)amino)ethyl, 2-((N-(3-morpholinopropylsulphonyl)-N-methyl)amino)ethyl, 2-((N-methyl-N-4-pyridyl)amino)ethyl, 3-(4-oxidomorpholino)propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2-((2-(pyrrolidin-1-yl)ethyl)carbamoyl)vinyl, 3-((2-(pyrrolidin-1-yl)ethyl)carbamoyl)prop-2-en-1-yl, 1-(2-pyrrolidinylethyl)piperidin-4-ylmethyl, 1-(3-pyrrolidinylpropyl)piperidin-4-ylmethyl, 1-(2-piperidinylethyl)piperidin-4-ylmethyl, 1-(3-piperidinylpropyl)piperidin-4-ylmethyl, 1-(2-morpholinoethyl)piperidin-4-ylmethyl, 1-(3-morpholinopropyl)piperidin-4-ylmethyl, 1-(2-thiomorpholinoethyl)piperidin-4-ylmethyl, 1-(3-thiomorpholinopropyl)piperidin-4-ylmethyl, 1-(2-azetidinylethyl)piperidin-4-ylmethyl or 1-(3-azetidinylpropyl)piperidin-4-ylmethyl, 3-morpholino-2-hydroxypropyl, (2R)-3-morpholino-2-hydroxypropyl, (2S)-3-morpholino-2-hydroxypropyl, 3-piperidino-2-hydroxypropyl, (2R)-3-piperidino-2-hydroxypropyl, (2S)-3-piperidino-2-hydroxypropyl, 3-pyrrolidin-1-yl-2-hydroxypropyl, (2R)-3-pyrrolidin-1-yl-2-hydroxypropyl, (2S)-3-pyrrolidin-1-yl-2-hydroxypropyl, 3-(1-methylpiperazin-4-yl)-2-hydroxypropyl, (2R)-3-(1-methylpiperazin-4-yl)-2-hydroxypropyl, (2S)-3-(1-methylpiperazin-4-yl)-2-hydroxypropyl, 3-(N,N-diethylamino)-2-hydroxypropyl, (2R)-3-N,N-diethylamino-2-hydroxypropyl, (2S)-3-(N,N-diethylamino)-2-hydroxypropyl, 3-(isopropylamino)-2-hydroxypropyl, (2R)-3-(isopropylamino)-2-hydroxypropyl, (2S)-3-(isopropylamino)-2-hydroxypropyl, 3-(N,N-diisopropylamino)-2-hydroxypropyl, (2R)-3-(N,N-diisopropylamino)-2-hydroxypropyl or (2S)-3-(N, N-diisopropylamino)-2-hydroxypropyl].

According to another aspect of the present invention particularly $R^2$ represents $C_{1-3}$alkyl, amino or $R^5X^1$— [wherein $X^1$ is as hereinbefore defined and $R^5$ represents ethyl, benzyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(ethylsulphinyl)ethyl, 2-(ethylsulphonyl)ethyl, 2-(N,N-dimethylsulphamoyl)ethyl, 2-(N-methylsulphamoyl)ethyl, 2-sulphamoylethyl, 2-(methylamino)ethyl, 3-(methylamino)propyl, 2-(ethylamino)ethyl, 3-(ethylamino)propyl, 2-(N,N-dimethylamino)ethyl, 3-(N,N-dimethylamino)propyl, 2-( N,N-diethylamino)ethyl, 3-(N,N-diethylamino)propyl, 2-N-methyl-N-methylsulphonylamino)ethyl, 3-(N-methyl-N-methylsulphonylamino)propyl, 2-morpholinoethyl, 3-morpholinopropyl, 2-piperidinoethyl, 3-piperidinopropyl, 2-(methylpiperidino)ethyl, 3-(methylpiperidino)propyl, 2-(ethylpiperidino)ethyl, 3-(ethylpiperidino)propyl, 2-((2-methoxyethyl)piperidino)ethyl, 3-((2-methoxyethyl)piperidino)propyl, 2-((2-methylsulphonyl)ethylpiperidino)ethyl, 3-((2-methylsulphonyl)ethylpiperidino)propyl, piperidin-3-ylmethyl, piperidin-4-ylmethyl, 2-(piperidin-3-yl) ethyl, 2-(piperidin-4-yl)ethyl, 3-(piperidin-3-yl)propyl, 3-(piperidin-4-yl)propyl, 2-(piperidin-2-yl)ethyl, 3-(piperidin-2-yl)propyl, (1-methylpiperidin-3-yl)methyl, (1-methylpiperidin-4-yl)methyl, (1-cyanomethylpiperidin-3-yl)methyl, (1-cyanomethylpiperidin-4-yl)methyl, 2-(methylpiperidin-3-yl)ethyl, 2-(methylpiperidin-4-yl)ethyl, 2-(1-cyanomethylpiperidin-3-yl)ethyl, 2-(1-cyanomethylpiperidin-4-yl)ethyl, 3-(methylpiperidin-3-yl)propyl, 3-(methylpiperidin-4-yl)propyl, 3-(1-cyanomethylpiperidin-3-yl)propyl, 3-(1-cyanomethylpiperidin-4-yl)propyl, 2-(ethylpiperidin-3-yl)ethyl, 2-(ethylpiperidin-4-yl)ethyl, 3-(ethylpiperidin-3-yl)propyl, 3-(ethylpiperidin-4-yl)propyl, ((2-methoxyethyl)piperidin-3-yl)methyl, ((2-methoxyethyl)piperidin-4-yl)methyl, 2-((2-methoxyethyl)piperidin-3-yl)ethyl, 2-((2-methoxyethyl)piperidin-4-yl)ethyl, 3-((2-methoxyethyl)piperidin-3-yl)propyl, 3-((2-methoxyethyl)piperidin-4-yl)propyl, (1-(2-methylsulphonylethyl)piperidin-3-yl)methyl, (1-(2-methylsulphonylethyl)piperidin-4-yl)methyl, 2-((2- methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 1-isopropylpiperidin-2-ylmethyl, 1-isopropylpiperidin-3-ylmethyl, 1-isopropylpiperidin-4-ylmethyl, 2-(1-isopropylpiperidin-2-yl)ethyl, 2-(1-isopropylpiperidin-3-yl)ethyl, 2-(1-isopropylpiperidin-4-yl)ethyl, 3-(1-isopropylpiperidin-2-yl)propyl, 3-(1-isopropylpiperidin-3-yl)propyl, 3-(1-isopropylpiperidin-4-yl)propyl, 2-(piperidin-4-yloxy)ethyl, 3-(piperidin-4-yloxy)propyl, 2-(1-(cyanomethyl)piperidin-4-yloxy)ethyl, 3-(1-(cyanomethyl)piperidin-4-yloxy)propyl, 2-(1-(2-cyanoethyl)piperidin-4-yloxy)ethyl, 3-(1-(2-cyanoethyl)piperidin-4-yloxy)propyl, 2-(piperazin-1-yl)ethyl, 3-(piperazin-1-yl)propyl, (pyrrolidin-2-yl)methyl, 2-(pyrrolidin-1-yl)ethyl, 3-(pyrrolidin-1-yl)propyl, (2-oxo-tetrahydro-2H-pyrrolidin-5-yl)methyl, 5(R)-(2-oxo-tetrahydro-2H-pyrrolidin-5-yl)methyl, (1,3-dioxolan-2-yl)methyl, 2-(1,3-dioxolan-2-yl)ethyl, 2-(2-methoxyethylamino)ethyl, 2-(N-(2-methoxyethyl)-N-methylamino)ethyl, 2-(2-hydroxyethylamino)ethyl, 3-(2-methoxyethylamino)propyl, 3-(N-(2-methoxyethyl)-N-methylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(2-methylimidazol-1-yl)ethyl, 2-(2-ethylimidazol-1-yl)ethyl, 3-(2-methylimidazol-1-yl)propyl, 3-(2-ethylimidazol-1-yl)propyl, 2-(1,2,3-triazol-1-yl)ethyl, 2-(1,2,3-triazol-2-yl)ethyl, 2-(1,2,4-triazol-1-yl)ethyl, 2-triazol-4-yl)ethyl, 4-pyridylmethyl, 2-(4-pyridyl)ethyl, 3-(4-pyridyl)propyl, 2-(4-pyridyloxy)ethyl, 2-(4-pyridylamino)ethyl, 2-(4-oxo-1,4-dihydro-1-pyridyl)ethyl, 2-(2-oxo-imidazolidin-1-yl)ethyl, 3-(2-oxo-imidazolidin-1-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 3-(methylsulphinyl)propyl, 3-(methylsulphonyl)propyl, 3-(ethylsulphinyl)propyl, 3-(ethylsulphonyl)propyl, 2-(5-methyl-1,2,4-triazol-1-yl)ethyl, morpholino, 2-((N-(1-methylimidazol-4-ylsulphonyl)-N-methyl)amino)ethyl, 2-((N-(3-morpholinopropylsulphonyl)-N-methyl)amino)ethyl, 2-((N-methyl-N-4-pyridyl)amino)ethyl, 3-(4-oxidomorpholino)propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2-((2-(pyrrolidin-1-yl)ethyl)carbamoyl)vinyl, 3-((2-(pyrrolidin-1-yl)ethyl)carbamoyl)prop-2-en-1-yl, 1-(2-pyrrolidinylethyl)piperidin-4-ylmethyl, 1-(3-pyrrolidinylpropyl)piperidin-4-ylmethyl, 1-(2-piperidinylethyl)piperidin-4-ylmethyl, 1-(3-piperidinylpropyl)piperidin-4-ylmethyl, 1-(2-morpholinoethyl)piperidin-4-ylmethyl, 1-(3-morpholinopropyl)piperidin-4-ylmethyl, 1-(2-thiomorpholinoethyl)piperidin-4-ylmethyl, 1-(3-thiomorpholinopropyl)piperidin-4-ylmethyl, 1-(2-azetidinylethyl)piperidin-4-ylmethyl or 1-(3-azetidinylpropyl)piperidin-4-ylmethyl, 3-morpholino-2-hydroxypropyl, (2R)-3-morpholino-2-hydroxypropyl, (2S)-3-morpholino-2-hydroxypropyl, 3-piperidino-2-hydroxypropyl, (2R)-3-piperidino-2-hydroxypropyl, (2S)-3-piperidino-2-hydroxypropyl, 3-pyrrolidin-1-yl-2-hydroxypropyl, (2R)-3-pyrrolidin-1-yl-2-hydroxypropyl, (2S)-3-pyrrolidin-1-yl-2-hydroxypropyl, 3-(1-methylpiperazin-4-yl)-2-hydroxypropyl, (2R)-3-(1-methylpiperazin-4-yl)-2-hydroxypropyl, (2S)-3-(1-methylpiperazin-4-yl)-2-hydroxypropyl, 3-(N,N-diethylamino)-2-hydroxypropyl, (2R)-3-(N,N-diethylamino)-2-hydroxypropyl, (2S)-3-(N,N-diethylamino)-2-hydroxypropyl, 3-(isopropylamino)-2-hydroxypropyl, (2R)-3-(isopropylamino)-2-hydroxypropyl, (2S)-3-(isopropylamino)-2-hydroxypropyl, 3-(N,N-diisopropylamino)-2-hydroxypropyl, (2R)-3-N,N-diisopropylamino)-2-hydroxypropyl or (2S)-3-N, N-diisopropylamino)-2-hydroxypropyl].

According to another aspect of the present invention more particularly $R^2$ represents $C_{1-3}$alkyl, amino or $R^5X^1$— [wherein $X^1$ is as hereinbefore defined and $R^5$ represents ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(ethylsulphinyl)ethyl, 2-(ethylsulphonyl)ethyl, 2-(N,N-dimethylsulphamoyl)ethyl, 2-N-methylsulphamoyl)ethyl, 2-sulphamoylethyl, 2-(methylamino)ethyl, 3-(methylamino)propyl, 2-(ethylamino)ethyl, 3-(ethylamino)propyl, 2-(N,N-dimethylamino)ethyl, 3-(N,N-dimethylamino)propyl, 2-(N,N-diethylamino)ethyl, 3-(N,N-diethylamino)propyl, 2-N-methyl-N-methylsulphonylamino)ethyl, 3-(N-methyl-N-methylsulphonylamino)propyl, 2-morpholinoethyl, 3-morpholinopropyl, 2-piperidinoethyl, 3-piperidinopropyl, 2-(methylpiperidino)ethyl, 3-(methylpiperidino)propyl, 2-(ethylpiperidino)ethyl, 3-(ethylpiperidino)propyl, 2-((2-methoxyethyl)piperidino)ethyl, 3-((2-methoxyethyl)piperidino)propyl, 2-((2-methylsulphonyl)ethylpiperidino)ethyl, 3-((2-methylsulphonyl)ethylpiperidino)propyl, piperidin-3-ylmethyl, piperidin-4-ylmethyl, 2-(piperidin-3-yl)ethyl, 2-(piperidin-4yl)ethyl, 3-(piperidin-3-yl)propyl, 3-(piperidin-4-yl)propyl, 2-(piperidin-2-yl)ethyl, 3-(piperidin-2-yl)propyl, (1-methylpiperidin-3-yl)methyl, (1-methylpiperidin-4-yl)methyl, (1-cyanomethylpiperidin-3-yl)methyl, (1-cyanomethylpiperidin-4-yl)methyl, 2-(methylpiperidin-3-yl)ethyl, 2-(methylpiperidin-4-yl)ethyl, 2-(1-cyanomethylpiperidin-3-yl)ethyl, 2-(1-cyanomethylpiperidin-4-yl)ethyl, 3-(methylpiperidin-3-yl)propyl, 3-(methylpiperidin-4-yl)propyl, 3-(1-cyanomethylpiperidin-3-yl)propyl, 3-(1-cyanomethylpiperidin-4-yl)propyl, 2-(ethylpiperidin-3-yl)ethyl, 2-(ethylpiperidin-4-yl)ethyl, 3-(ethylpiperidin-3-yl)propyl, 3-(ethylpiperidin-4-yl)propyl, ((2-methoxyethyl)piperidin-3-yl)methyl, ((2-methoxyethyl)piperidin-4-yl)methyl, 2-((2-methoxyethyl)piperidin-3-yl)ethyl, 2-((2-methoxyethyl)piperidin-4-yl)ethyl, 3-((2-methoxyethyl)piperidin-3-yl)propyl, 3-((2-methoxyethyl)piperidin-4-yl)propyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 1-isopropylpiperidin-2-ylmethyl, 1-isopropylpiperidin-3-ylmethyl, 1-isopropylpiperidin-4-ylmethyl, 2-(1-isopropylpiperidin-2-yl)ethyl, 2-(1-isopropylpiperidin-3-yl)ethyl, 2-(1-isopropylpiperidin-4-yl)ethyl, 3-(1-isopropylpiperidin-2-yl)propyl, 3-(1-isopropylpiperidin-3-yl)propyl, 3-(1-isopropylpiperidin-4-yl)propyl, 2-(piperidin-4-yloxy)ethyl, 3-(piperidin-4-yloxy)propyl, 2-(1-(cyanomethyl)piperidin-4-yloxy)ethyl, 3-(1-(cyanomethyl)piperidin-4-yloxy)propyl, 2-(1-(2-cyanoethyl)piperidin-4-yloxy)ethyl, 3-(1-(2-cyanoethyl)piperidin-4-yloxy)propyl, 2-(piperazin-1-yl)ethyl, 3-(piperazin-1-yl)propyl, (pyrrolidin-2-yl)methyl, 2-(pyrrolidin-1-yl)ethyl, 3-(pyrrolidin-1-yl)propyl, (2-oxo-tetrahydro-2H-pyrrolidin-5-yl)methyl, 5(R)-(2-oxo-tetrahydro-2H-pyrrolidin-5-yl)methyl, (5S)-(2-oxo-tetrahydro-2H-pyrrolidin-5-yl)methyl, (1,3-dioxolan-2-yl)methyl, 2-(1,3-dioxolan-2-yl)ethyl, 2-methoxyethylamino)ethyl, 2-(N-(2-methoxyethyl)-N-methylamino)ethyl, 2-(2-hydroxyethylamino)ethyl, 3-(2-methoxyethylamino)propyl, 3-(N-(2-methoxyethyl)-N- methylamino)propyl, 3-(2-hydroxyethylamino)propyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-pyridyl)propyl, 2-(4-pyridyloxy)ethyl, 2-(4-pyridylamino)ethyl, 2-(4-oxo-1,4-dihydro-1-pyridyl)ethyl, 2-(2-oxo-imidazolidin-1-yl)ethyl, 3-(2-oxo-imidazolidin-1-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 3-(methylsulphinyl)propyl, 3-(methylsulphonyl)propyl, 3-(ethylsulphinyl)propyl, 3-(ethylsulphonyl)propyl, 2-(5-methyl-1,2,4-triazol-1-yl)ethyl, morpholino, 2-((N-(3-morpholinopropylsulphonyl)-N-methyl)amino)ethyl, 2-((N-methyl-N-4-pyridyl)amino)ethyl, 3-(4-oxidomorpholino)propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2-((2-(pyrrolidin-1-yl)ethyl)carbamoyl)vinyl, 3-((2-(pyrrolidin-1-yl)ethyl)carbamoyl)prop-2-en-1-yl, 1-(2-pyrrolidinylethyl)piperidin-4-ylmethyl, 1-(3-pyrrolidinylpropyl)piperidin-4-ylmethyl, 1-(2-piperidinylethyl)piperidin-4-ylmethyl, 1-(3-piperidinylpropyl)piperidin-4-ylmethyl, 1-(2-morpholinoethyl)piperidin-4-ylmethyl, 1-(3-morpholinopropyl)piperidin-4-ylmethyl, 1-(2-thiomorpholinoethyl)piperidin-4-ylmethyl, 1-(3-thiomorpholinopropyl)piperidin-4-ylmethyl, 1-(2-azetidinylethyl)piperidin-4-ylmethyl or 1-(3-azetidinylpropyl)piperidin-4-ylmethyl, 3-morpholino-2-hydroxypropyl, (2R)-3-morpholino-2-hydroxypropyl, (2S)-3-morpholino-2-hydroxypropyl, 3-piperidino-2-hydroxypropyl, (2R)-3-piperidino-2-hydroxypropyl, (2S)-3-piperidino-2-hydroxypropyl, 3-pyrrolidin-1-yl-2-hydroxypropyl, (2R)-3-pyrrolidin-1-yl-2-hydroxypropyl, (2S)-3-pyrrolidin-1-yl-2-hydroxypropyl, 3-(1-methylpiperazin-4-yl)-2-hydroxypropyl, (2R)-3-(1-methylpiperazin-4-yl)-2-hydroxypropyl, (2S)-3-(1-methylpiperazin-4-yl)-2-hydroxypropyl, 3-(N,N-diethylamino)-2-hydroxypropyl, (2R)-3-(N,N-diethylamino)-2-hydroxypropyl, (2S)-3-(N,N-diethylamino)-2-hydroxypropyl, 3-(isopropylamino)-2-hydroxypropyl, (2R)-3-(isopropylamino)-2-hydroxypropyl, (2S)-3-(isopropylamino)-2-hydroxypropyl, 3-(N,N-diisopropylamino)-2-hydroxypropyl, (2R)-3-(N,N-diisopropylamino)-2-hydroxypropyl or (2S)-3-(N, N-diisopropylamino)-2-hydroxypropyl].

In another aspect $R^2$ represents ethoxy, trifluoromethoxy, 2,2,2-trifluoroethoxy, 2-hydroxyethoxy, 3-hydroxypropoxy, 2-methoxyethoxy, 3-methoxypropoxy, 2-(methylsulphinyl)ethoxy, 2-(methylsulphonyl)ethoxy, 2-(ethylsulphinyl)ethoxy, 2-(ethylsulphonyl)ethoxy, 2-(N,N-dimethylsulphamoyl)ethoxy, 2-(N-methylsulphamoyl)ethoxy, 2-sulphamoylethoxy, 2-(methylamino)ethoxy, 3-(methylamino)propoxy, 2-(ethylamino)ethoxy, 3-(ethylamino)propoxy, 2-(N,N-dimethylamino)ethoxy, 3-(N,N-dimethylamino)propoxy, 2-(N,N-diethylamino)ethoxy, 3-(N,N-diethylamino)propoxy, 2-N-methyl-N-methylsulphonylamino)ethoxy, 3-N-methyl-N-methylsulphonylamino)propoxy, 2-morpholinoethoxy, 3-morpholinopropoxy, 2-piperidinoethoxy, 3-piperidinopropoxy, 2-(methylpiperidino)ethoxy, 3-(methylpiperidino)propoxy, 2-(ethylpiperidino)ethoxy, 3-(ethylpiperidino)propoxy, 2-((2-methoxyethyl)piperidino)ethoxy, 3-((2-methoxyethyl)piperidino)propoxy, 2-((2-methylsulphonyl)ethylpiperidino)ethoxy, 3-((2-methylsulphonyl)ethylpiperidino)propoxy, piperidin-3-ylmethoxy, piperidin-4-ylmethoxy, 2-(piperidin-3-yl)ethoxy, 2-(piperidin-4-yl)ethoxy, 3-(piperidin-3-yl)propoxy, 3-(piperidin-4-yl)propoxy, 2-(piperidin-2-yl)ethoxy, 3-(piperidin-2-yl)propoxy, (1-methylpiperidin-3-yl)methoxy, (1-methylpiperidin-4-yl)methoxy, (1-cyanomethylpiperidin-3-yl)methoxy, (1-cyanomethylpiperidin-4-yl)methoxy, 2-(methylpiperidin-3-yl)ethoxy, 2-(methylpiperidin-4-yl)ethoxy, 2-(1-cyanomethylpiperidin-3-yl)ethoxy, 2-(1-cyanomethylpiperidin-4-yl)ethoxy, 3-(methylpiperidin-3-yl)propoxy, 3-(methylpiperidin-4-yl)propoxy, 3-(1-cyanomethylpiperidin-3-yl)propoxy, 3-(1-cyanomethylpiperidin-4-yl)propoxy, 2-(ethylpiperidin-3-yl)ethoxy, 2-(ethylpiperidin-4-yl)ethoxy, 3-(ethylpiperidin-3-yl)propoxy, 3-(ethylpiperidin-4yl)propoxy, ((2-methoxyethyl)piperidin-3-yl)methoxy, ((2-methoxyethyl)piperidin-4-yl)methoxy, 2-((2-methoxyethyl)piperidin-3-yl)ethoxy, 2-((2-methoxyethyl)piperidin-4-yl)ethoxy, 3-((2-methoxyethyl)piperidin-3-yl)propoxy, 3-((2-methoxyethyl)piperidin-4-yl)propoxy, (1-(2-methylsulphonylethyl)piperidin-3-yl)methoxy, (1-(2-methylsulphonylethyl)piperidin-4-yl)methoxy, 2-((2-methylsulphonylethyl)piperidin-3-yl)ethoxy, 2-((2-methylsulphonylethyl)piperidin-4-yl)ethoxy, 3-((2-methylsulphonylethyl)piperidin-3-yl)propoxy, 3-((2-methylsulphonylethyl)piperidin-4-yl)propoxy, 1-isopropylpiperidin-2-ylmethoxy, 1-isopropylpiperidin-3-ylmethoxy, 1-isopropylpiperidin-4-ylmethoxy, 2-(1-isopropylpiperidin-2-yl)ethoxy, 2-(1-isopropylpiperidin-3-yl)ethoxy, 2-(1-isopropylpiperidin-4-yl)ethoxy, 3-(1-isopropylpiperidin-2-yl)propoxy, 3-(1-isopropylpiperidin-3-yl)propoxy, 3-(1-isopropylpiperidin-4-yl)propoxy, 2-(piperidin-4-yloxy)ethoxy, 3-(piperidin-4-yloxy)propoxy, 2-(1-(cyanomethyl)piperidin-4-yloxy)ethoxy, 3-(1-(cyanomethyl)piperidin-4-yloxy)propoxy, 2-(1-(2-cyanoethyl)piperidin-4-yloxy)ethoxy, 3-(1-(2-cyanoethyl)piperidin-4-yloxy)propoxy, 2-(piperazin-1-yl)ethoxy, 3-(piperazin-1-yl)propoxy, (pyrrolidin-2-yl)methoxy, 2-(pyrrolidin-1-yl)ethoxy, 3-(pyrrolidin-1-yl)propoxy, (2-oxo-tetrahydro-2H-pyrrolidin-5-yl)methoxy, 5(R)-(2-oxo-tetrahydro-2H-pyrrolidin-5-yl)methoxy, (5S)-(2-oxo-tetrahydro-2H-pyrrolidin-5-yl)methoxy, (1,3-dioxolan-2-yl)methoxy, 2-(1,3-dioxolan-2-yl)ethoxy, 2-(2-methoxyethylamino)ethoxy, 2-(N-(2-methoxyethyl)-N-methylamino)ethoxy, 2-(2-hydroxyethylamino)ethoxy, 3-(2-methoxyethylamino)propoxy, 3-(N-(2-methoxyethyl)-N-methylamino)propoxy, 3-(2-hydroxyethylamino)propoxy, 2-(1,2,3-triazol-1-yl)ethoxy, 2-(1,2,3-triazol-2-yl)ethoxy, 2-(1,2,4-triazol-1-yl)ethoxy, 2-(1,2,4-triazol-4-yl)ethoxy, pyridylmethoxy, 2-(4-pyridyl)ethoxy, 3-(4-pyrimidyl)propoxy, 2-(4-pyridyloxy)ethoxy, 2-(4-pyridylamino)ethoxy, 2-(4-oxo-1,4-dihydro-1-pyridyl)ethoxy, 2-(2-oxo-imidazolidin-1-yl)ethoxy, 3-(2-oxo-imidazolidin-1-yl)propoxy, 2-thiomorpholinoethoxy, 3-thiomorpholinopropoxy, 2-(1,1-dioxothiomorpholino)ethoxy, 3-(1,1-dioxothiomorpholino)propoxy, 2-(2-methoxyethoxy)ethoxy, 2-(4-methylpiperazin-1-yl)ethoxy, 3-(4-methylpiperazin-1-yl)propoxy, 3-(methylsulphinyl)propoxy, 3-(methylsulphonyl)propoxy, 3-(ethylsulphinyl)propoxy, 3-(ethylsulphonyl)propoxy, 2-(5-methyl-1,2,4-triazol-1-yl)ethoxy, 2-(N-(3-morpholinopropylsulphonyl)-N-methyl)amino)ethoxy, 2-((N-methyl-N-4-pyridyl)amino)ethoxy, 3-(4-oxidomorpholino)propoxy, 2-(2-(4-methylpiperazin-1-yl)ethoxy)ethoxy, 3-(2-(4-methylpiperazin-1-yl)ethoxy)propoxy, 2-(2-morpholinoethoxy)ethoxy, 3-(2-morpholinoethoxy)propoxy, 2-(tetrahydropyran-4-yloxy)ethoxy, 3-(tetrahydropyran-4-yloxy)propoxy, 2-((2-(pyrrolidin-1-yl)ethyl)carbamoyl)vinyl, 3-((2-(pyrrolidin-1-yl)ethyl)carbamoyl)prop-2-en-1-yloxy, 1-(2-pyrrolidinylethyl)piperidin-4-ylmethoxy, 1-(3-pyrrolidinylpropyl)piperidin-4-ylmethoxy, 1-(2-piperidinylethyl)piperidin- 4-ylmethoxy, 1-(3-piperidinylpropyl)piperidin-4-ylmethoxy, 1-(2-morpholinoethyl)piperidin-4-ylmethoxy, 1-(3-morpholinopropyl)piperidin-4-ylmethoxy, 1-(2-thiomorpholinoethyl)piperidin-4-ylmethoxy, 1-(3-thiomorpholinopropyl)piperidin-4-ylmethoxy, 1-(2-azetidinylethyl)piperidin-4-ylmethoxy, 1-(3-azetidinylpropyl)piperidin-4-ylmethoxy, 3-morpholino-2-hydroxypropoxy, (2R)-3-morpholino-2-hydroxypropoxy, (2S)-3-morpholino-2-hydroxypropoxy, 3-piperidino-2-hydroxypropoxy, (2R)-3-piperidino-2-hydroxypropoxy, (2S)-3-piperidino-2-hydroxypropoxy, 3-pyrrolidin-1-yl-2-hydroxypropoxy, (2R)-3-pyrrolidin-1-yl-2-hydroxypropoxy, (2S)-3-pyrrolidin-1-yl-2-hydroxypropoxy, 3-(1-methylpiperazin-4-yl)-2-hydroxypropoxy, (2R)-3-(1-methylpiperazin-4-yl)-2-hydroxypropoxy, (2S)-3-(1-methylpiperazin-4-yl)-2-hydroxypropoxy, 3-(N,N-diethylamino)-2-hydroxypropoxy, (2R)-3-(N,N-diethylamino)-2-hydroxypropoxy, (2S)-3-(N,N-diethylamino)-2-hydroxypropoxy, 3-(isopropylamino)-2-hydroxypropoxy, (2R)-3-(isopropylamino)-2-hydroxypropoxy, (2S)-3-(isopropylamino)-2-hydroxypropoxy, 3-(N,N-diisopropylamino)-2-hydroxypropoxy, (2R)-3-N,N-diisopropylamino)-2-hydroxypropoxy or (2S)-3-(N,N-diisopropylamino)-2-hydroxypropoxy.

Where one of the $R^2$ substituents is $R^5X^1$— the substituent $R^5X^1$— is preferably at the 5- or 7-position of the quinoline ring, more preferably at the 7-position of the quinoline ring.

When one of the $R^2$ substituents is at the 6-position of the quinoline ring it is preferably hydrogen, halogeno, $C_{1-3}$alkyl, trifluoromethyl, cyano, $C_{1-3}$alkoxy, $C_{1-3}$alkylsulphanyl or —$NR^3R^4$ (wherein $R^3$ and $R^4$ are as defined hereinbefore).

When one of the $R^2$ substituents is at the 6-position of the quinoline ring it is more preferably hydrogen, $C_{1-3}$alkoxy, cyano, trifluoromethyl, $C_{1-3}$alkylsulphanyl, fluoro, chloro, bromo or nitro.

When one of the $R^2$ substituents is at the 6-position of the quinoline ring it is particularly hydrogen, methoxy or cyano, especially cyano.

In another aspect of the present invention there is provided the use of compounds of the formula Ia:

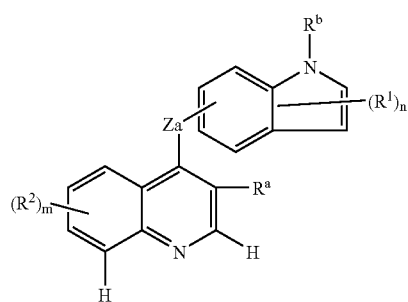

(Ia)

wherein
$R^a$, $R^b$, $R^1$, $R^2$, n and m are as defined hereinbefore and Za represents —O—, —NH— or —S—;

or a salt thereof, or a prodrug thereof for example an ester or an amide, in the manufacture of a medicament for use in the production of an antiangiogenic and/or vascular permeability reducing effect in warm-blooded animals such as humans.

In a further aspect of the present invention there is provided the use of compounds of the formula Ib:

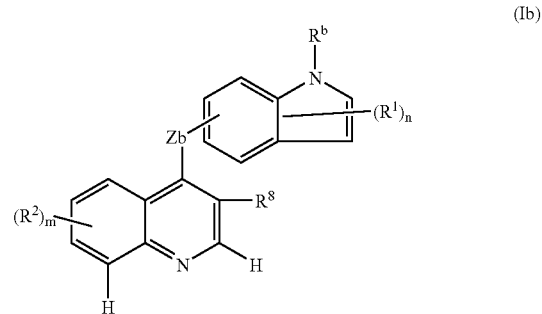

(Ib)

wherein $R^a$, $R^b$, $R^1$, $R^2$, n and m are as defined hereinbefore and Zb represents —O— or —NH—;

or a salt thereof, or a prodrug thereof for example an ester or an amide, in the manufacture of a medicament for use in the production of an antiangiogenic and/or vascular permeability reducing effect in warm-blooded animals such as humans.

In a further aspect of the present invention there is provided the use of compounds of the formula Ib as defined hereinbefore, with the proviso that $R^2$ at the 7-position of the quinoline ring cannot have any value selected from hydrogen, methyl, methoxy and chloro; or a salt thereof, or a prodrug thereof for example an ester or an amide, in the manufacture of a medicament for use in the production of an antiangiogenic and/or vascular permeability reducing effect in warm-blooded animals such as humans.

According to another aspect of the present invention there is provided a compound of the formula I as defined hereinbefore and salts thereof, and prodrugs thereof for example esters, amides and sulphides, preferably esters and amides.

According to another aspect of the present invention there is provided a compound of the formula $I^1$ as defined hereinbefore and salts thereof, and prodrugs thereof for example esters, amides and sulphides, preferably esters and amides.

According to another aspect of the present invention there is provided a compound of the formula Ia as defined hereinbefore and salts thereof, and prodrugs thereof for example esters, amides and sulphides, preferably esters and amides.

According to another aspect of the present invention there is provided a compound of the formula Ib as defined hereinbefore and salts thereof, and prodrugs thereof for example esters, amides and sulphides, preferably esters and amides.

According to another aspect of the present invention there is provided a compound of the formula I as defined hereinbefore with the proviso that $R^2$ at the 7-position of the quinoline ring cannot have any value selected from hydrogen, methyl, methoxy and chloro; and salts thereof, and prodrugs thereof for example esters, amides and sulphides, preferably esters and amides.

According to another aspect of the present invention there is provided a compound of the formula $I^1$ as defined hereinbefore with the proviso that $R^2$ at the 7-position of the quinoline ring cannot have any value selected from hydrogen, methyl, methoxy and chloro; and salts thereof, and prodrugs thereof for example esters, amides and sulphides, preferably esters and amides.

According to another aspect of the present invention there is provided a compound of the formula Ia as defined hereinbefore with the proviso that $R^2$ at the 7-position of the quinoline ring cannot have any value selected from hydrogen, methyl, methoxy and chloro; and salts thereof, and prodrugs thereof for example esters, amides and sulphides, preferably esters and amides.

According to another aspect of the present invention there is provided a compound of the formula Ib as defined hereinbefore with the proviso that $R^2$ at the 7-position of the quinoline ring cannot have any value selected from hydrogen, methyl, methoxy and chloro; and salts thereof, and prodrugs thereof for example esters, amides and sulphides, preferably esters and amides.

According to one aspect of the present invention preferred compounds are:
6-cyano-4-(2-methylindol-6-yloxy)-7-(3-(4-methylpiperazin-1-yl)propoxy)quinoline,
6-cyano-4-(2-methylindol-6-yloxy)-7-(3-(pyrrolidin-1-yl)propoxy)quinoline,
6-cyano-4-(2,3-dimethylindol-5-ylamino)-7-(2-(1,2,3-triazol-1-yl)ethoxy)quinoline,
6-cyano-7-(3-(1,1-dioxothiomorpholino)propoxy)-4-(2-methylindol-5-ylamino)quinoline,
6-cyano-4-(2,3-dimethylindol-5-ylamino)-7-(3-(1,1-dioxothiomorpholino)propoxy)quinoline,
6-cyano-4-(2,3-dimethylindol-5-yloxy)-7-(3-(1,1-dioxothiomorpholino)propoxy)quinoline,
6-cyano-7-(3-(1,1-dioxothiomorpholino)propoxy)-4-(2-methylindol-5-yloxy)quinoline,
6-cyano-4-(4-fluoro-2-methylindol-5-yloxy)-7-(2-methoxyethoxy)quinoline,
6-cyano-4-(4-fluoro-2-methylindol-5-yloxy)-7-(2-(1,2,3-triazol-1-yl)ethoxy)quinoline,
6-cyano-4-(4-fluoro-2-methylindol-5-yloxy)-7-(3-(1,2,3-triazol-1-yl)propoxy)quinoline, and
6-cyano-4-(4-fluoro-2-methylindol-5-yloxy)-7-(3-(1,1-dioxothiomorpholino)propoxy)quinoline, and salts thereof.

According to another aspect of the present invention a preferred compound is:
6-cyano-4-(4-fluoro-2-methylindol-5-yloxy)-7-((4-pyridyl)methoxy)quinoline and salts thereof.

According to one aspect of the present invention more preferred compounds are:
6-cyano-7-(3-(1,1-dioxothiomorpholino)propoxy)-4-(indol-5-ylamino)quinoline,
6-cyano-4-(indol-5-ylamino)-7-(2-(1,2,3-triazol-1-yl)ethoxy)quinoline,
6-cyano-4-(2-methylindol-5-ylamino)-7-(2-(1,2,3-triazol-1-yl)ethoxy)quinoline,
6-cyano-4-(2-methylindol-5-yloxy)-7-(3-(4-methylpiperazin-1-yl)propoxy)quinoline,
6-cyano-7-(3-(1,1-dioxothiomorpholino)propoxy)-4-(indol-5-yloxy)quinoline,
6-cyano-4-(4-fluoro-2-methylindol-5-yloxy)-7-(3-(pyrrolidin-1-yl)propoxy)quinoline,
6-cyano-4-(4-fluoro-2-methylindol-5-yloxy)-7-(3-(4-methylpiperazin-1-yl)propoxy)quinoline,
6-cyano-4-(2-methylindol-5-yloxy)-7-(3-(pyrrolidin-1-yl)propoxy)quinoline,
6-cyano-4-(indol-5-yloxy)-7-(3-(pyrrolidin-1-yl)propoxy)quinoline,
6-cyano-4-(2,3-dimethylindol-5-yloxy)-7-(3-(pyrrolidin-1-yl)propoxy)quinoline,
6-cyano-4-(1,2-dimethylindol-5-yloxy)-7-(3-(pyrrolidin-1-yl)propoxy)quinoline,
6-cyano-4-(2,3-dimethylindol-5-yloxy)-7-(3-(4-methylpiperazin-1-yl)propoxy)quinoline,
6-cyano-4-(1,2-dimethylindol-5-yloxy)-7-(3-(4-methylpiperazin-1-yl)propoxy)quinoline,
6-cyano-4-(4-fluoroindol-5-yloxy)-7-(3-(pyrrolidin-1-yl)propoxy)quinoline,
6-cyano-4-(6-fluoroindol-5-yloxy)-7-(3-(pyrrolidin-1-yl)propoxy)quinoline,
6-cyano-4-(6-fluoroindol-5-yloxy)-7-(3-(4-methylpiperazin-1-yl)propoxy)quinoline,
6-cyano-4-(indol-5-yloxy)-7-(3-(4-methylpiperazin-1-yl)propoxy)quinoline,
6-cyano-4-(4-fluoro-2-methylindol-5-ylamino)-7-(3-(pyrrolidin-1-yl)propoxy)quinoline,
6-cyano-4-(2-methylindol-5-ylamino)-7-(3-pyrrolidin-1-yl)propoxy)quinoline, and
6-cyano-4-(3-methylindol-5-yloxy)-7-(3-(pyrrolidin-1-yl)propoxy)quinoline, and salts thereof Another more preferred compound of the invention is:
6-cyano-4-(indol-5-ylamino)-7-(3-(4-methylpiperazin-1-yl)propoxy)quinoline and salts thereof.

Preferred compounds of the present invention include
6-cyano-7-(3-(1,1-dioxothiomorpholino)propoxy)-4-(indol-5-ylamino)quinoline,
6-cyano-4-(indol-5-ylamino)-7-(2-(1,2,3-triazol-1-yl)ethoxy)quinoline,
6-cyano-4-(2-methylindol-5-ylamino)-7-(2-(1,2,3-triazol-1-yl)ethoxy)quinoline,
6-cyano-4-(2,3-dimethylindol-5-ylamino)-7-(2-(1,2,3-triazol-1-yl)ethoxy)quinoline,
6-cyano-4-(2-methylindol-5-yloxy)-7-(3-(4-methylpiperazin-1-yl)propoxy)quinoline,
6-cyano-7-(3-(1,1-dioxothiomorpholino)propoxy)-4-(indol-5-yloxy)quinoline,
6-cyano-4-(4-fluoro-2-methylindol-5-yloxy)-7-(3-(pyrrolidin-1-yl)propoxy)quinoline,
6-cyano-4-(4-fluoro-2-methylindol-5-yloxy)-7-(3-(4-methylpiperazin-1-yl)propoxy)quinoline,
6-cyano-4-(2-methylindol-5-yloxy)-7-(3-(pyrrolidin-1-yl)propoxy)quinoline,
6-cyano-4-(indol-5-yloxy)-7-(3-(pyrrolidin-1-yl)propoxy)quinoline,
6-cyano-4-(2,3-dimethylindol-5-yloxy)-7-(3-(pyrrolidin-1-yl)propoxy)quinoline,
6-cyano-4-(1,2-dimethylindol-5-yloxy)-7-(3-(pyrrolidin-1-yl)propoxy)quinoline,
6-cyano-4-(2-methylindol-6-yloxy)-7-(3-(pyrrolidin-1-yl)propoxy)quinoline,
6-cyano-4-(2-methylindol-6-yloxy)-7-(3-(4-methylpiperazin-1-yl)propoxy)quinoline,
6-cyano(2,3-dimethylindol-5-yloxy)-7-(3-(4-methylpiperazin-1-yl)propoxy)quinoline,
6-cyano-4-(1,2-dimethylindol-5-yloxy)-7-(3-(4-methylpiperazin-1-yl)propoxy)quinoline,
6-cyano-4-(4-fluoroindol-5-yloxy)-7-(3-(pyrrolidin-1-yl)propoxy)quinoline,
6-cyano-4-(6-fluoroindol-5-yloxy)-7-(3-(pyrrolidin-1-yl)propoxy)quinoline,
6-cyano-4-(6-fluoroindol-5-yloxy)-7-(3-(4-methylpiperazin-1-yl)propoxy)quinoline,
6-cyano-4-(indol-5-yloxy)-7-(3-(4-methylpiperazin-1-yl)propoxy)quinoline, 6-cyano-4-(4-fluoro-2-methylindol-5-ylamino)-7-(3-(pyrrolidin-1-yl)propoxy)quinoline, and 6-cyano-4-(2-methylindol-5-ylamino)-7-(3-(pyrrolidin-1-yl)propoxy)quinoline, and salts thereof.

Another preferred compound of the invention is:
6-cyano-4-(indol-5-ylamino)-7-(3-(4-methylpiperazin-1-yl)propoxy)quinoline and salts thereof.

For the avoidance of doubt it is to be understood that where in this specification a group is qualified by 'hereinbefore defined' or 'defined hereinbefore' the said group encompasses the first occurring and broadest definition as well as each and all of the preferred definitions for that group.

In this specification unless stated otherwise the term "alkyl" includes both straight and branched chain alkyl groups but references to individual alkyl groups such as "propyl" are specific for the straight chain version only. An analogous convention applies to other generic terms. Unless otherwise stated the term "alkyl" advantageously refers to chains with 1–6 carbon atoms, preferably 1–4 carbon atoms. The term "alkoxy" as used herein, unless stated otherwise includes "alkyl"—O— groups in which "alkyl" is as hereinbefore defined. The term "aryl" as used herein unless stated otherwise includes reference to a $C_{6-10}$ aryl group which may, if desired, carry one or more substituents selected from halogeno, alkyl, alkoxy, nitro, trifluoromethyl and cyano, (wherein alkyl and alkoxy are as hereinbefore defined). The term "aryloxy" as used herein unless otherwise stated includes "aryl"—O— groups in which "aryl" is as hereinbefore defined. The term "sulphonyloxy" as used herein refers to alkylsulphonyloxy and arylsulphonyloxy groups in which "alkyl" and "aryl" are as hereinbefore defined. The term "alkanoyl" as used herein unless otherwise stated includes formyl and alkylC=O groups in which "alkyl" is as defined hereinbefore, for example $C_2$alkanoyl is ethanoyl and refers to $CH_3C=O$, $C_1$alkanoyl is formyl and refers to CHO. In this specification unless stated otherwise the term "alkenyl" includes both straight and branched chain alkenyl groups but references to individual alkenyl groups such as 2-butenyl are specific for the straight chain version only. Unless otherwise stated the term "alkenyl" advantageously refers to chains with 2–5 carbon atoms, preferably 3–4 carbon atoms. In this specification unless stated otherwise the term "alkynyl" includes both straight and branched chain alkynyl groups but references to individual alkynyl groups such as 2-butynyl are specific for the straight chain version only. Unless otherwise stated the term "alkynyl" advantageously refers to chains with 2–5 carbon atoms, preferably 3–4 carbon atoms. Unless stated otherwise the term "haloalkyl" refers to an alkyl group as defined hereinbefore which bears one or more halogeno groups, such as for example trifluoromethyl.

For the avoidance of any doubt, where $R^2$ has a value of substituted or unsubstituted $C_{1-5}$alkyl, $R^2$ has been selected from $C_{1-3}$alkyl or from a group $R^5X^1$ wherein $X^1$ is a direct bond or —$CH_2$— and $R^5$ is $C_{1-5}$alkyl which may be unsubstituted or which may be substituted with one or more groups selected from hydroxy, fluoro, chloro, bromo and amino.

Within the present invention it is to be understood that a compound of the formula I or a salt thereof may exhibit the phenomenon of tautomerism and that the formulae drawings within this specification can represent only one of the possible tautomeric forms. It is to be understood that the invention encompasses any tautomeric form which inhibits VEGF receptor tyrosine kinase activity and is not to be limited merely to any one tautomeric form utilised within the formulae drawings. The formulae drawings within this specification can represent only one of the possible tautomeric forms and it is to be understood that the specification encompasses all possible tautomeric forms of the compounds drawn not just those forms which it has been possible to show graphically herein.

It will be appreciated that compounds of the formula I or a salt thereof may possess an asymmetric carbon atom. Such an asymmetric carbon atom is also involved in the tautomerism described above, and it is to be understood that the present invention encompasses any chiral form (including both pure enantiomers, scalemic and racemic mixtures) as well as any tautomeric form which inhibits VEGF receptor tyrosine kinase activity, and is not to be limited merely to any one tautomeric form or chiral form utilised within the formulae drawings. It is to be understood that the invention encompasses all optical and diastereomers which inhibit VEGF receptor tyrosine kinase activity. It is further to be understood that in the names of chiral compounds (R,S) denotes any scalemic or racemic mixture while (R) and (S) denote the enantiomers. In the absence of (R,S), (R) or (S) in the name it is to be understood that the name refers to any scalemic or racemic mixture, wherein a scalemic mixture contains R and S enantiomers in any relative proportions and a racemic mixture contains R and S enantiomers in the ration 50:50.

It is also to be understood that certain compounds of the formula I and salts thereof can exist in solvated as well as unsolvated forms such as, for example, hydrated forms. It is to be understood that the invention encompasses all such solvated forms which inhibit VEGF receptor tyrosine kinase activity.

For the avoidance of any doubt, it is to be understood that when $X^1$ is, for example, a group of formula —$NR^6C(O)$—, it is the nitrogen atom bearing the $R^6$ group which is attached to the quinoline ring and the carbonyl (C(O)) group is attached to $R^5$, whereas when $X^1$ is, for example, a group of formula —$C(O)NR^7$—, it is the carbonyl group which is attached to the quinoline ring and the nitrogen atom bearing the $R^7$ group is attached to $R^5$. A similar convention applies to the other two atom $X^1$ linking groups such as —$NR^9SO_2$— and —$SO_2NR^8$—. When $X^1$ is —$NR^{10}$— it is the nitrogen atom bearing the $R^{10}$ group which is linked to the quinoline ring and to $R^5$. An analogous convention applies to other groups. It is further to be understood that when $X^1$ represents —$NR^{10}$— and $R^{10}$ is $C_{1-3}$alkoxy$C_{2-3}$alkyl it is the $C_{2-3}$alkyl moiety which is linked to the nitrogen atom of $X^1$ and an analogous convention applies to other groups.

For the avoidance of any doubt, it is to be understood that in a compound of the formula I when $R^5$ is, for example, a group of formula $C_{1-3}$alkyl$X^9C_{1-3}$alkyl$R^{29}$, it is the terminal $C_{1-3}$alkyl moiety which is linked to $X^1$, similarly when $R^5$ is, for example, a group of formula $C_{2-5}$alkenyl$R^{28}$ it is the $C_{2-5}$alkenyl moiety which is linked to $X^1$ and an analogous convention applies to other groups. When $R^5$ is a group 1-$R^{29}$prop-1-en-3-yl it is the first carbon to which the group $R^{29}$ is attached and it is the third carbon which is linked to $X^1$ and an analogous convention applies to other groups.

For the avoidance of any doubt, it is to be understood that in a compound of the formula I when $R^5$ is, for example, $R^{28}$ and $R^{28}$ is a pyrrolidinyl ring which bears a group —(—O—)$_f$($C_{1-4}$alkyl)$_g$ringD, it is the —O— or $C_{1-4}$alkyl which is linked to the pyrrolidinyl ring, unless f and g are both 0 when it is ring D which is linked to the pyrrolidinyl ring and an analogous convention applies to other groups.

For the avoidance of any doubt, it is to be understood that when $R^{29}$ carries a $C_{1-4}$aminoalkyl substituent it is the $C_{1-4}$alkyl moiety which is attached to $R^{29}$ whereas when $R^{29}$ carries a $C_{1-4}$alkylamino substituent it is the amino moiety which is attached to $R^{29}$ and an analogous convention applies to other groups.

For the avoidance of any doubt, it is to be understood that when $R^{28}$ carries a $C_{1-4}$alkoxy$C_{1-4}$alkyl substituent it is the $C_{1-4}$alkyl moiety which is attached to $R^{28}$ and an analogous convention applies to other groups.

For the avoidance of any doubt, it is to be understood that when $R^1$ is —$C_{1-5}$alkyl(ring B) it is the alkyl chain which is linked to the indole group and ring B is attached to the alkyl chain and an analogous convention applies to other groups.

For the avoidance of any doubt, it is to be understood that when $R^b$ is $C_{2-5}$alkenylamino$C_{1-4}$alkyl, it is the $C_{1-4}$alkyl group which is linked to the nitrogen atom of the 5-membered ring and an analogous convention applies to other groups.

The present invention relates to the compounds of formula I as hereinbefore defined as well as to the salts thereof. Salts for use in pharmaceutical compositions will be pharmaceutically acceptable salts, but other salts may be useful in the production of the compounds of formula I and their pharmaceutically acceptable salts. Pharmaceutically acceptable salts of the invention may, for example, include acid addition salts of the compounds of formula I as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. In addition where the compounds of formula I are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

A compound of the formula I, or salt thereof, and other compounds of the invention (as herein defined) may be prepared by any process known to be applicable to the preparation of chemically-related compounds. Such processes include, for example, those illustrated in International Patent Application Publication No. WO 98/13350 and in International Patent Application Publicaiton No. WO 00/47212 (Application No. PCT/GB00/00373). Such processes also include, for example, solid phase synthesis. Such processes, are provided as a further feature of the invention and are as described hereinafter. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

Thus, the following processes (a) to (f) and (i) to (vi) constitute further features of the present invention.

Synthesis of Compounds of Formula I
(a) Compounds of the formula I and salts thereof may be prepared by the reaction of a compound of the formula III:

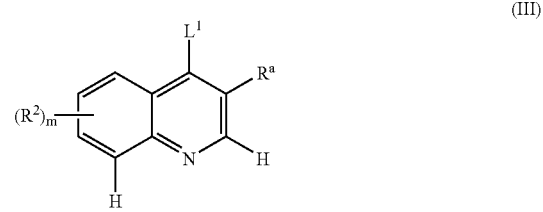

(wherein $R^a$, $R^2$ and m are as defined hereinbefore and $L^1$ is a displaceable moiety), with a compound of the formula IV:

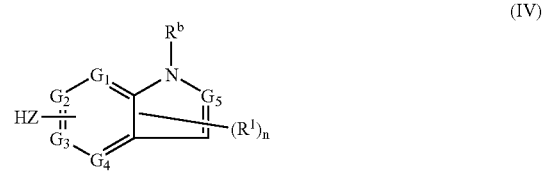

(wherein $R^b$, $R^1$, $G_1$, $G_2$, $G_3$, $G_4$, $G_5$, Z and n are as defined hereinbefore) to obtain compounds of the formula I and salts thereof. A convenient displaceable moiety $L^1$ is, for example, a halogeno, alkoxy (preferably $C_{1-4}$alkoxy), aryloxy, alkylsulphanyl, arylsulphanyl, alkoxyalkylsulphanyl or sulphonyloxy group, for example a chloro, bromo, methoxy, phenoxy, methylsulphanyl, 2-methoxyethylsulphanyl, methanesulphonyloxy or toluene-4-sulphonyloxy group.

The reaction is advantageously effected in the presence of a base. When Z is —O— such a base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, tetramethylguanidine or for example, an alkali metal or alkaline earth metal carbonate or hydroxide, for example sodium carbonate, potassium carbonate, cesium carbonate, calcium carbonate, sodium hydroxide or potassium hydroxide. Alternatively such a base is, for example, an alkali metal hydride, for example sodium hydride, or an alkali metal or alkaline earth metal amide, for example sodium amide, sodium bis(trimethylsilyl)amide, potassium amide or potassium bis(trimethylsilyl)amide. The reaction is preferably effected in the presence of an inert solvent or diluent, for example an ether such as tetrahydrofuran or 1,4-dioxan, an aromatic hydrocarbon solvent such as toluene, or a dipolar aprotic solvent such as N,N-dimethylformamide, N,N-dimethylacetamide, N-methylpyrrolidin-2-one or dimethyl sulphoxide. The reaction is conveniently effected at a temperature in the range, for example, 10 to 150° C., preferably in the range 20 to 100° C.

When Z is —NH— the reaction is advantageously effected in the presence of either an acid or a base. Such an acid is for example, an anhydrous inorganic acid such as hydrochloric acid, in the presence of a protic solvent or diluent, for example an alcohol or ester such as methanol, ethanol, 2-propanol, 2-pentanol.

When it is desired to obtain the acid salt, the free base may be treated with an acid such as a hydrogen halide, for example hydrogen chloride, sulphuric acid, a sulphonic acid, for example methane sulphonic acid, or a carboxylic acid, for example acetic or citric acid, using a conventional procedure.

(b) Production of those compounds of formula I and salts thereof wherein at least one $R^2$ is $R^5X^1$ wherein $R^5$ is as defined hereinbefore and $X^1$ is —O—, —S—, —OC(O)— or —NR$^{10}$— (wherein $R^{10}$ independently represents hydrogen, $C_{1-3}$alkyl or $C_{1-3}$alkoxyC$_{2-3}$alkyl) can be achieved by the reaction, conveniently in the presence of a base (as defined hereinbefore in process (a)) of a compound of the formula V:

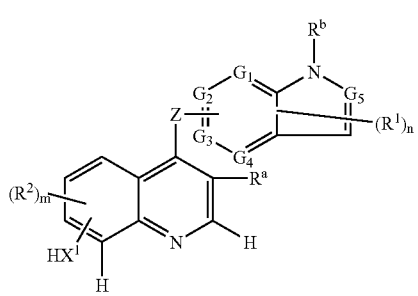

(wherein $R^a$, $R^b$, Z, $G_1$, $G_2$, $G_3$, $G_4$, $G_5$, $R^1$, $R^2$ and n are as hereinbefore defined and $X^1$ is as hereinbefore defined in this section and s is an integer from 0 to 2) with a compound of formula VI:

$R^5$-$L^1$ (VI)

(wherein $R^5$ and $L^1$ are as hereinbefore defined), $L^1$ is a displaceable moiety for example a halogeno or sulphonyloxy group such as a bromo, methanesulphonyloxy or toluene-4-sulphonyloxy group, or $L^1$ may be generated in situ from an alcohol under standard Mitsunobu conditions ("Organic Reactions", John Wiley & Sons Inc, 1992, vol 42, chapter 2, David L Hughes). The reaction is preferably effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 50° C.

(c) Compounds of the formula I and salts thereof wherein at least one $R^2$ is $R^5X^1$ wherein $R^5$ is as defined hereinbefore and $X^1$ is —O—, —S—, —OC(O)— or —NR$^{10}$— (wherein $R^{10}$ represents hydrogen, $C_{1-3}$alkyl or $C_{1-3}$alkoxyC$_{2-3}$alkyl) may be prepared by the reaction of a compound of the formula VII:

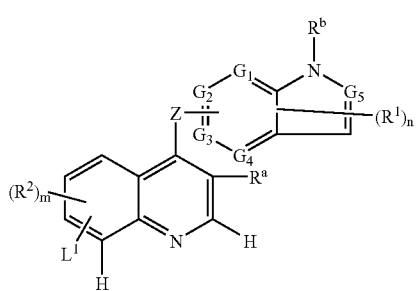

with a compound of the formula VIII:

$R^5$-$X^1$-H (VIII)

(wherein $L^1$, $R^a$, $R^b$, $R^1$, $R^2$, $R^5$, $G_1$, $G_2$, $G_3$, $G_4$, $G_5$, Z, n and s are all as hereinbefore defined and $X^1$ is as hereinbefore defined in this section). The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

(d) Compounds of the formula I and salts thereof wherein at least one $R^2$ is $R^5X^1$ wherein $X^1$ is as defined hereinbefore and $R^5$ is $C_{1-5}$alkylR$^{62}$, wherein $R^{62}$ is selected from one of the following nine groups:

1) $X^{10}C_{1-3}$alkyl (wherein $X^{10}$ represents —O—, —S—, —SO$_2$—, —NR$^{63}$C(O)— or —NR$^{64}$SO$_2$— (wherein $R^{63}$ and $R^{64}$ which may be the same or different are each hydrogen, $C_{1-3}$alkyl or $C_{1-3}$alkoxyC$_{2-3}$alkyl);

2) NR$^{65}$R$^{66}$ (wherein $R^{65}$ and $R^{66}$ which may be the same or different are each hydrogen, $C_{1-3}$alkyl or $C_{1-3}$alkoxyC$_{2-3}$alkyl);

3) $X^{11}C_{1-5}$alkylX$^5$R$^{22}$ (wherein $X^{11}$ represents —O—, —S—, —SO$_2$—, —NR$^{67}$C(O)—, —NR$^{68}$SO$_2$— or —NR$^{69}$— (wherein $R^{67}$, $R^{68}$, and $R^{69}$ which may be the same or different are each hydrogen, $C_{1-3}$alkyl or $C_{1-3}$alkoxyC$_{2-3}$alkyl) and $X^5$ and $R^{22}$ are as defined hereinbefore);

4) $R^{28}$ (wherein $R^{28}$ is as defined hereinbefore);

5) $X^{12}R^{29}$ (wherein $X^{12}$ represents —O—, —S—, —SO$_2$—, —NR$^{70}$C(O)—, NR$^{71}$SO$_2$—, or —NR$^{72}$— (wherein $R^{70}$, $R^{71}$, and $R^{72}$ which may be the same or different are each hydrogen, $C_{1-3}$alkyl or $C_{1-3}$alkoxyC$_{2-3}$alkyl) and $R^{29}$ is as defined hereinbefore); and 6) $X^{13}C_{1-3}$alkylR$^{29}$ (wherein $X^{13}$ represents —O—, —S—, —SO$_2$—, —NR$^{73}$C(O)—, —NR$^{74}$SO$_2$— or —NR$^{75}$— (wherein $R^{73}$, $R^{74}$ and $R^{75}$ each independently represents hydrogen, $C_{1-3}$alkyl or $C_{1-3}$alkoxyC$_{2-3}$alkyl) and $R^{29}$ is as defined hereinbefore);

7) $R^{29}$ (wherein $R^{29}$ is as defined hereinbefore);

8) $X^{13}C_{1-4}$alkylR$^{28}$ (wherein $X^{13}$ and $R^{28}$ are as defined hereinbefore); and 9) $R^{54}(C_{1-4}$alkyl)$_q$(X$^9$)$_r$R$^{55}$ (wherein q, r, $X^9$, $R^{54}$ and $R^{55}$ are as defined hereinbefore);

may be prepared by reacting a compound of the formula IX:

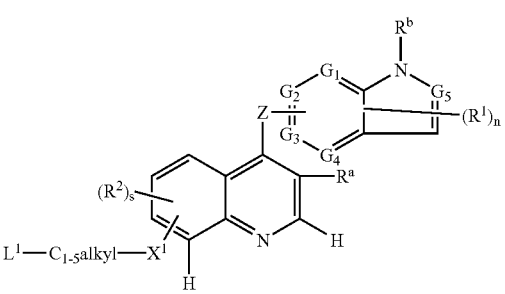

(wherein $L^1$, $X^1$, $R^a$, $R^b$, $R^1$, $R^2$, $G_1$, $G_2$, $G_3$, $G_4$, $G_5$, Z, n and s are as hereinbefore defined) with a compound of the formula X:

$R^{62}$—H (X)

(wherein $R^{62}$ is as defined hereinbefore) to give a compound of the formula I or salt thereof. The reaction may conveniently be effected in the presence of a base (as defined hereinbefore in process (a)) and advantageously in the presence of an inert solvent or diluent (as defined hereinbefore in process (a)), and at a temperature in the range, for example 0 to 150° C., conveniently at about 50° C.

Processes (a) and (b) are preferred over processes (c) and (d).

Process (a) is preferred over processes (b), (c) and (d).

(e) The production of those compounds of the formula I and salts thereof wherein one or more of the substituents $(R^2)_m$ is represented by $-NR^{76}R^{77}$, where one (and the other is hydrogen) or both of $R^{76}$ and $R^{77}$ are $C_{1-3}$alkyl, may be effected by the reaction of compounds of formula I wherein the substituent $(R^2)_m$ is an amino group and an alkylating agent, preferably in the presence of a base as defined hereinbefore. Such alkylating agents are $C_{1-3}$alkyl moieties bearing a displaceable moiety as defined hereinbefore such as $C_{1-3}$alkyl halides for example $C_{1-3}$alkyl chloride, bromide or iodide. The reaction is preferably effected in the presence of an inert solvent or diluent (as defined hereinbefore in process (a)) and at a temperature in the range, for example, 10 to 100° C., conveniently at about ambient temperature. The production of compounds of formula I and salts thereof wherein one or more of the substituents $R^2$ is an amino group may be effected by the reduction of a corresponding compound of formula I wherein the substituent(s) at the corresponding position(s) of the quinoline group is/are a nitro group(s). The reduction of the nitro group(s) may conveniently be effected by any of the procedures known for such a transformation. The reduction may be carried out, for example, by the hydrogenation of a solution of the nitro compound in the presence of an inert solvent or diluent as defined hereinbefore in the presence of a metal effective to catalyse hydrogenation reactions such as palladium or platinum. A further reducing agent is, for example, an activated metal such as activated iron (produced for example by washing iron powder with a dilute solution of an acid such as hydrochloric acid). Thus, for example, the reduction may be effected by heating the nitro compound and the activated metal in the presence of a solvent or diluent such as a mixture of water and alcohol, for example methanol or ethanol, to a temperature in the range, for example 50 to 150° C., conveniently at about 70° C. The production of a compound of formula I and salts thereof wherein the substituent(s) at the corresponding position(s) of the quinoline group is/are a nitro group(s) may be effected by the processes described hereinbefore and hereinafter in processes (a–d) and (i–v) using a compound selected from the compounds of the formulae (I–XX) in which the substituent(s) at the corresponding position(s) of the quinoline group is/are a nitro group(s).

(f) Compounds of the formula I and salts thereof wherein $X^1$ is $-SO-$ or $-SO_2-$ may be prepared by oxidation from the corresponding compound in which $X^1$ is $-S-$ or $-SO-$ (when $X^1$ is $-SO_2-$ is required in the final product). Conventional oxidation conditions and reagents for such reactions are well known to the skilled chemist.

Synthesis of Intermediates (i) The compounds of formula III and salts thereof in which $L^1$ is halogeno may for example be prepared by halogenating a compound of the formula XI:

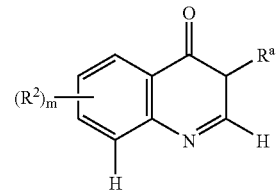

(XI)

wherein $R^a$, $R^2$ and m are as hereinbefore defined).

Convenient halogenating agents include inorganic acid halides, for example thionyl chloride, phosphorus(III) chloride, phosphorus(V)oxychloride and phosphorus(V)chloride. The halogenation reaction may be effected in the presence of an inert solvent or diluent such as for example a halogenated solvent such as methylene chloride, trichloromethane or carbon tetrachloride, or an aromatic hydrocarbon solvent such as benzene or toluene, or the reaction may be effected without the presence of a solvent. The reaction is conveniently effected at a temperature in the range, for example 10 to 150° C., preferably in the range 40 to 100° C.

The compounds of formula XI and salts thereof may, for example, be prepared by reacting a compound of the formula XII:

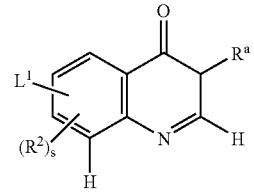

(XII)

(wherein $R^a$, $R^2$, s and $L^1$ are as hereinbefore defined) with a compound of the formula VII as hereinbefore defined. The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

Compounds of formula XI and salts thereof may also be prepared by cyclising a compound of the formula XIII:

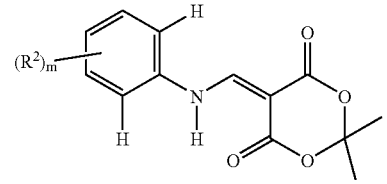

(XIII)

(wherein $R^2$ and m are as hereinbefore defined,) whereby to form a compound of formula XI or salt thereof. The cyclisation may be effected by heating a compound of the formula XIII in the presence of an inert solvent or diluent such as an ether, for example diphenyl ether, at an elevated temperature, preferably in the range 200 to 300° C.

Compounds of formula XIII may for example be prepared by reacting a compound of the formula XIV:

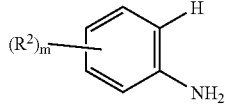
(XIV)

with a compound of the formula XV:

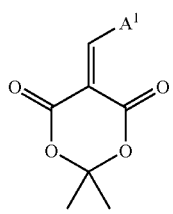
(XV)

(wherein $R^2$ and m are as hereinbefore defined and $A^1$ is an alkoxy (preferably $C_{1-4}$alkoxy) group). The reaction may conveniently be effected in the presence of an alcohol as solvent, such as ethanol and advantageously at a temperature in the range for example 20 to 100° C., preferably in the range 50 to 100° C.

The compounds of formula m and salts thereof wherein at least one $R^2$ is $R^5X^1$ and wherein $X^1$ is —O—, —S—, —$SO_2$—, —OC(O)—, —C(O)$NR^7$—, —$SO_2NR^8$— or —$NR^{10}$— (wherein $R^7$, $R^8$ and $R^{10}$ each independently represents hydrogen, $C_{1-3}$alkyl or $C_{1-3}$alkoxy$C_{2-3}$alkyl), may also be prepared for example by reacting a compound of the formula XVI:

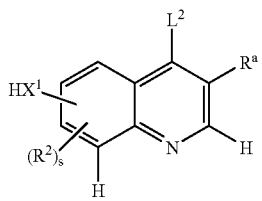
(XVI)

(wherein $R^a$, $R^2$ and s are as hereinbefore defined, $X^1$ is as hereinbefore defined in this section and $L^2$ represents a displaceable protecting moiety) with a compound of the formula VI as hereinbefore defined, whereby to obtain a compound of formula III in which $L^1$ is represented by $L^2$.

A compound of formula XVI is conveniently used in which $L^2$ represents a chloro group or a phenoxy group which may if desired carry up to 5 substituents, preferably up to 2 substituents, selected from halogeno, nitro and cyano. The reaction may be conveniently effected under conditions as described for process (b) hereinbefore.

The compounds of formula XVI and salts thereof may for example be prepared by deprotecting a compound of the formula XVII:

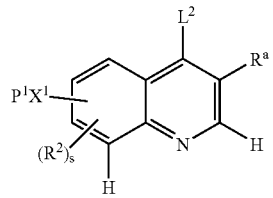
(XVII)

(wherein $R^a$, $R^2$, s and $L^2$ are as hereinbefore defined, $P^1$ is a protecting group and $X^1$ is as hereinbefore defined in the section describing compounds of the formula XVI). The choice of protecting group $P^1$ is within the standard knowledge of an organic chemist, for example those included in standard texts such as "Protective Groups in Organic Synthesis" T. W. Greene and R. G. M. Wuts, 2nd Ed. Wiley 1991, including N-sulphonyl derivatives (for example, p-toluenesulphonyl), carbamates (for example, t-butyl carbonyl), N-alkyl derivatives (for example, 2-chloroethyl, benzyl) and amino acetal derivatives (for example benzyloxymethyl). The removal of such a protecting group may be effected by any of the procedures known for such a transformation, including those reaction conditions indicated in standard texts such as that indicated hereinbefore, or by a related procedure. Deprotection may be effected by techniques well known in the literature, for example where $P^1$ represents a benzyl group deprotection may be effected by hydrogenolysis or by treatment with trifluoroacetic acid.

One compound of formula III may if desired be converted into another compound of formula III in which the moiety $L^1$ is different. Thus for example a compound of formula III in which $L^1$ is other than halogeno, for example optionally substituted phenoxy, may be converted to a compound of formula III in which $L^1$ is halogeno by hydrolysis of a compound of formula III (in which $L^1$ is other than halogeno) to yield a compound of formula XI as hereinbefore defined, followed by introduction of halide to the compound of formula XI, thus obtained as hereinbefore defined, to yield a compound of formula III in which $L^1$ represents halogen.

(ii) Compounds of formula IV may be prepared by any of the methods known in the art, such as for example those described in "Indoles Part I", "Indoles Part II", 1972 John Wiley & Sons Ltd and "Indoles Part III" 1979, John Wiley & Sons Ltd, edited by W. J. Houlihan. Compounds of formula IV may be prepared by methods given in the Examples hereinafter. Compounds of formula IV may be prepared by any of the processes described in International Patent Application Publication No. WO 00/47212, the entire content of which is included herein by reference, with particular reference to the processes described in WO 00/47212 in Examples 48, 182 237, 242, 250 and 291 therein. For example the azaindole 2-methyl-1H-pyrrolo[2,3-b]pyridin-5-ol, maybe prepared according to the method described in Reference Example 1 hereinafter.

(iii) Compounds of formula V as hereinbefore defined and salts thereof may be made by deprotecting the compound of formula XVIII:

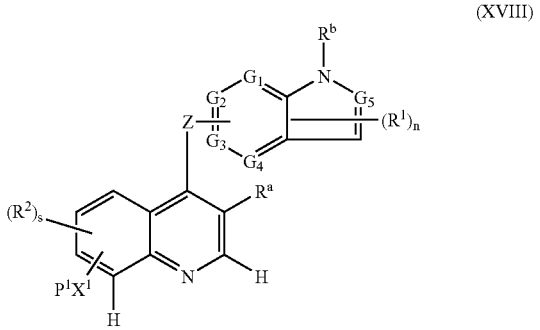

(XVIII)

(wherein Z, $R^a$, $R^b$, $R^1$, $R^2$, $G_1$, $G_2$, $G_3$, $G_4$, $G_5$, $P^1$, n and s are as hereinbefore defined and $X^1$ is as hereinbefore defined in the section describing compounds of the formula V) by a process for example as described in (i) above.

Compounds of the formula XVIII and salts thereof may be made by reacting compounds of the formulae XVII and IV as hereinbefore defined, under the conditions described in (a) hereinbefore, to give a compound of the formula XVIII or salt thereof.

(iv) Compounds of the formula VII and salts thereof may be made by reacting a compound of the formula XIX:

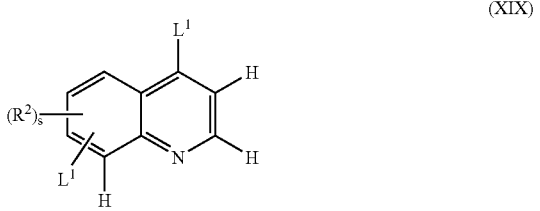

(XIX)

(wherein $R^2$, s and each $L^1$ are as hereinbefore defined and the $L^1$ in the 4-position and the other $L^1$ in a further position on the quinoline ring may be the same or different) with a compound of the formula I as hereinbefore defined, the reaction for example being effected by a process as described in (a) above.

(v) Compounds of formula IX as defined hereinbefore and salts thereof may for example be made by the reaction of compounds of formula V as defined hereinbefore with compounds of the formula XX:

$L^1$-$C_{1-5}$alkyl-$L^1$     (XX)

(wherein $L^1$ is as hereinbefore defined) to give compounds of formula IX or salts thereof. The reaction may be effected for example by a process as described in (b) above.

(vi) Intermediate compounds wherein $X^1$ is —SO— or —$SO_2$— may be prepared by oxidation from the corresponding compound in which $X^1$ is —S— or —SO— (when $X^1$ is —$SO_2$— is required in the final product). Conventional oxidation conditions and reagents for such reactions are well known to the skilled chemist.

When a pharmaceutically acceptable salt of a compound of the formula I is required, it may be obtained, for example, by reaction of said compound with, for example, an acid using a conventional procedure, the acid having a pharmaceutically acceptable anion.

Many of the intermediates defined herein, for example, those of the formulae IV, V, VII, IX and XVII are novel and these are provided as a further feature of the invention. The preparation of these compounds is as described herein and/or is by methods well known to persons skilled in the art of organic chemistry.

The identification of compounds which potently inhibit the tyrosine kinase activity associated with VEGF receptors such as Flt and/or KDR and which inhibit angiogenesis and/or increased vascular permeability is desirable and is the subject of the present invention. These properties may be assessed, for example, using one or more of the procedures set out below:

(a) In Vitro Receptor Tyrosine Kinase Inhibition Test

This assay determines the ability of a test compound to inhibit tyrosine kinase activity. DNA encoding VEGF, FGF or EGF receptor cytoplasmic domains may be obtained by total gene synthesis (Edwards M, International Biotechnology Lab 5(3), 19–25, 1987) or by cloning. These may then be expressed in a suitable expression system to obtain polypeptide with tyrosine kinase activity. For example VEGF, FGF and EGF receptor cytoplasmic domains, which were obtained by expression of recombinant protein in insect cells, were found to display intrinsic tyrosine kinase activity. In the case of the VEGF receptor Flt (Genbank accession number X51602), a 1.7 kb DNA fragment encoding most of the cytoplasmic domain, commencing with methionine 783 and including the termination codon, described by Shibuya et al (Oncogene, 1990, 5: 519–524), was isolated from cDNA and cloned into a baculovirus transplacement vector (for example pAcYM1 (see The Baculovirus Expression System: A Laboratory Guide, L. A. King and R. D. Possee, Chapman and Hall, 1992) or pAc360 or pBlueBacHis (available from Invitrogen Corporation)). This recombinant construct was co-transfected into insect cells (for example Spodoptera frugiperda 21(Sf21)) with viral DNA (eg Pharmingen BaculoGold) to prepare recombinant baculovirus. (Details of the methods for the assembly of recombinant DNA molecules and the preparation and use of recombinant baculovirus can be found in standard texts for example Sambrook et al, 1989, Molecular cloning—A Laboratory Manual, 2nd edition, Cold Spring Harbour Laboratory Press and O'Reilly et al, 1992, Baculovirus Expression Vectors—A Laboratory Manual, W. H. Freeman and Co, New York). For other tyrosine kinases for use in assays, cytoplasmic fragments starting from methionine 806 (KDR, Genbank accession number L04947), methionine 668 (EGF receptor, Genbank accession number X00588) and methionine 399 (FGF R1 receptor, Genbank accession number X51803) may be cloned and expressed in a similar manner.

For expression of cFlt tyrosine kinase activity, Sf21 cells were infected with plaque-pure cFlt recombinant virus at a multiplicity of infection of 3 and harvested 48 hours later. Harvested cells were washed with ice cold phosphate buffered saline solution (PBS) (10 mM sodium phosphate pH7.4, 138 mM sodium chloride, 2.7 mM potassium chloride) then resuspended in ice cold HNTG/PMSF (20 mM Hepes pH7.5, 150 mM sodium chloride, 10% v/v glycerol, 1% v/v Triton X100, 1.5 mM magnesium chloride, 1 mM ethylene glycol-bis(βaminoethyl ether) N,N,N',N'-tetraacetic acid (EGTA), 1 mM PMSF (phenylmethylsulphonyl fluoride); the PMSF is added just before use from a freshly-prepared 100 mM solution in methanol) using 1 ml HNTG/PMSF per 10 million cells. The suspension was centrifuged for 10 minutes at 13,000 rpm at 4° C., the supernatant (enzyme stock) was removed and stored in aliquots at −70°

C. Each new batch of stock enzyme was titrated in the assay by dilution with enzyme diluent (100 mM Hepes pH 7.4, 0.2 mM sodium orthovanadate, 0.1% v/v Triton X100, 0.2 mM dithiothreitol). For a typical batch, stock enzyme is diluted 1 in 2000 with enzyme diluent and 50 µl of dilute enzyme is used for each assay well.

A stock of substrate solution was prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100 µl of diluted substrate solution was dispensed into all wells of assay plates (Nunc maxisorp 96-well immunoplates) which were sealed and left overnight at 4° C.

On the day of the assay the substrate solution was discarded and the assay plate wells were washed once with PBST (PBS containing 0.05% v/v Tween 20) and once with 50 mM Hepes pH7.4.

Test compounds were diluted with 10% dimethylsulphoxide (DMSO) and 25 µl of diluted compound was transferred to wells in the washed assay plates. "Total" control wells contained 10% DMSO instead of compound. Twenty five microlitres of 40 mM manganese(II)chloride containing 8 µM adenosine-5'-triphosphate (ATP) was added to all test wells except "blank" control wells which contained manganese(II)chloride without ATP. To start the reactions 50 µl of freshly diluted enzyme was added to each well and the plates were incubated at room temperature for 20 minutes. The liquid was then discarded and the wells were washed twice with PBST. One hundred microlitres of mouse IgG anti-phosphotyrosine antibody (Upstate Biotechnology Inc. product 05-321), diluted 1 in 6000 with PBST containing 0.5% w/v bovine serum albumin (BSA), was added to each well and the plates were incubated for 1 hour at room temperature before discarding the liquid and washing the wells twice with PBST. One hundred microlitres of horse radish peroxidase (HRP)-linked sheep anti-mouse Ig antibody (Amersham product NXA 931), diluted 1 in 500 with PBST containing 0.5% w/v BSA, was added and the plates were incubated for 1 hour at room temperature before discarding the liquid and washing the wells twice with PBST. One hundred microlitres of 2,2'-azino-bis(3-ethylbenzthiazoline-6-sulphonic acid) (ABTS) solution, freshly prepared using one 50 mg ABTS tablet Boehringer 1204 521) in 50 ml freshly prepared 50 mM phosphate-citrate buffer pH5.0+0.03% sodium perborate (made with 1 phosphate citrate buffer with sodium perborate (PCSB) capsule (Sigma P4922) per 100 ml distilled water), was added to each well. Plates were then incubated for 20–60 minutes at room temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibtion of enzyme activity.

(b) In Vitro HUVEC Proliferation Assay

This assay determines the ability of a test compound to inhibit the growth factor-stimulated proliferation of human umbilical vein endothelial cells (HUVEC).

HUVEC cells were isolated in MCDB 131 (Gibco BRL)+ 7.5% v/v foetal calf serum (FCS) and were plated out (at passage 2 to 8), in MCDB ;131+2% v/v FCS+3 µg/ml heparin+1 µg/ml hydrocortisone, at a concentration of 1000 cells/well in 96 well plates. After a minimum of 4 hours they were dosed with the appropriate growth factor (i.e. VEGF 3 ng/ml, EGF 3 ng/ml or b-FGF 0.3 ng/ml) and compound. The cultures were then incubated for 4 days at 37° C. with 7.5% $CO_2$. On day 4 the cultures were pulsed with 1 µCi/well of tritiated-thymidine (Amersham product TRA 61) and incubated for 4 hours. The cells were harvested using a 96-well plate harvester (Tomtek) and then assayed for incorporation of tritium with a Beta plate counter. Incorporation of radioactivity into cells, expressed as cpm, was used to measure inhibition of growth factor-stimulated cell proliferation by compounds.

(c) In Vivo Solid Tumour Disease Model

This test measures the capacity of compounds to inhibit solid tumour growth.

Calu-6 tumour xenografts were established in the flank of female athymic Swiss nu/nu mice, by subcutaneous injection of $1 \times 10^6$ Calu-6 cells/mouse in 100 µl of a 50% (v/v) solution of Matrigel in serum free culture medium. Ten days after cellular implant, mice were allocated to groups of 8–10, so as to achieve comparable group mean volumes. Tumours were measured using vernier calipers and volumes were calculated as: $(l \times w) \times \sqrt{(l \times w)} \times (\pi/6)$, where l is the longest diameter and w the diameter perpendicular to the longest. Test compounds were administered orally once daily for a minimum of 21 days, and control animals received compound diluent. Tumours were measured twice weekly. The level of growth inhibition was calculated by comparison of the mean tumour volume of the control group versus the treatment group using a Student T test and/or a Mann-Whitney Rank Sum Test. The inhibitory effect of compound treatment was considered significant when $p<0.05$.

According to a further aspect of the invention there is provided a pharmaceutical composition which comprises a compound of the formula I as defined hereinbefore or a pharmaceutically acceptable salt thereof, in association with a pharmaceutically acceptable excipient or carrier.

The composition may be in a form suitable for oral administration, for example as a tablet or capsule, for parenteral injection (including intravenous, subcutaneous, intramuscular, intravascular or infusion) for example as a sterile solution, suspension or emulsion, for topical administration for example as an ointment or cream or for rectal administration for example as a suppository. In general the above compositions may be prepared in a conventional manner using conventional excipients.

The compositions of the present invention are advantageously presented in unit dosage form. The compound will normally be administered to a warm-blooded animal at a unit dose within the range 5–5000 mg per square metre body area of the animal, i.e. approximately 0.1–100 mg/kg. A unit dose in the range, for example, 1–100 mg/g, preferably 1–50 mg/kg is envisaged and this normally provides a therapeutically-effective dose. A unit dose form such as a tablet or capsule will usually contain, for example 1–250 mg of active ingredient.

According to a further aspect of the present invention there is provided a compound of the formula I or a pharmaceutically acceptable salt thereof as defined hereinbefore for use in a method of treatment of the human or animal body by therapy.

We have found that compounds of the present invention inhibit VEGF receptor tyrosine kinase activity and are therefore of interest for their antiangiogenic effects and/or their ability to cause a reduction in vascular permeability.

A further feature of the present invention is a compound of formula I, or a pharmaceutically acceptable salt thereof, for use as a medicament, conveniently a compound of formula I, or a pharmaceutically acceptable salt thereof, for use as a medicament for producing an antiangiogenic and/or vascular permeability reducing effect in a warm-blooded animal such as a human being.

Thus according to a further aspect of the invention there is provided the use of a compound of the formula I, or a pharmaceutically acceptable salt thereof in the manufacture of a medicament for use in the production of an antiangiogenic and/or vascular permeability reducing effect in a warm-blooded animal such as a human being.

According to a further feature of the invention there is provided a method for producing an antiangiogenic and/or vascular permeability reducing effect in a warm-blooded animal, such as a human being, in need of such treatment which comprises administering to said animal an effective amount of a compound of formula I or a pharmaceutically acceptable salt thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

The antiangiogenic and/or vascular permeability reducing treatment defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the antiangiogenic and/or vascular permeability reducing treatment defined hereinbefore may be: surgery, radiotherapy or chemotherapy. Such chemotherapy may cover three main categories of therapeutic agent:

(i) other antiangiogenic agents that work by different mechanisms from those defined hereinbefore (for example linomide, inhibitors of integrin αvβ3 function, angiostatin, razoxin, thalidomide), and including vascular targeting agents (for example combretastatin phosphate and the vascular damaging agents described in International Patent Application Publication No. WO 99/02166 the entire disclosure of which document is incorporated herein by reference, (for example N-acetylcolchinol-O-phosphate) and in International Patent Application Publication No. WO 00/40529 the entire disclosure of which document is incorporated herein by reference);

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophospharnide, ifosfamide, nitrosoureas, thiotepa); antimitotic agents (for example vinca alkaloids like vincristine and taxoids like taxol, taxotere); topoisomerase inhibitors (for example epipodophyllotoxins like etoposide and teniposide, amsacrine, topotecan, and also irinotecan); also enzymes (for example asparaginase); and thymidylate synthase inhibitors (for example raltitrexed); and additional types of chemotherapeutic agent include:

(iv) biological response modifiers (for example interferon); and (v) antibodies (for example edrecolomab).

For example such conjoint treatment may be achieved by way of the simultaneous, sequential or separate administration of a compound of formula I as defined hereinbefore, and a vascular targeting agent described in WO 99/02166 such as N-acetylcolchinol-O-phosphate (Exampe 1 of WO 99/02166).

As stated above the compounds defined in the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, acute and chronic nephropathies, atheroma, arterial restenosis, autoimmune diseases, acute inflammation, excessive scar formation and adhesions, lymphoedema, endometriosis, dysfunctional uterine bleeding and ocular diseases with retinal vessel proliferation. In particular such compounds of the invention are expected to slow advantageously the growth of primary and recurrent solid tumours of, for example, the colon, breast, prostate, lungs and skin. More particularly such compounds of the invention are expected to inhibit the growth of those primary and recurrent solid tumours which are associated with VEGF, especially those tumours which are significantly dependent on VEGF for their growth and spread, including for example, certain tumours of the colon, breast, prostate, lung, vulva and skin.

In addition to their use in therapeutic medicine, the compounds of formula I and their pharmaceutically acceptable salts are also useful as pharmacological tools in the development and standardisation of in vitro and in vivo test systems for the evaluation of the effects of inhibitors of VEGF receptor tyrosine kinase activity in laboratory animals such as cats, dogs, rabbits, monkeys, rats and mice, as part of the search for new therapeutic agents.

It is to be understood that where the term "ether" is used anywhere in this specification it refers to diethyl ether.

The invention will now be illustrated in the following non-limiting Examples in which, unless otherwise stated:

(i) evaporations were carried out by rotary evaporation in vacuo and work-up procedures were carried out after removal of residual solids such as drying agents by filtration;
(ii) operations were carried out at ambient temperature, that is in the range 18–25° C. and under an atmosphere of an inert gas such as argon;
(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;
(iv) yields are given for illustration only and are not necessarily the maximum attainable;
(v) melting points are uncorrected and were determined using a Mettler SP62 automatic melting point apparatus, an oil-bath apparatus or a Koffler hot plate apparatus.
(vi) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;
(vii) intermediates were not generally fully characterised and purity was assessed by thin layer chromatography (TLC), high-performance liquid chromatography (HPLC), infra-red (IR) or NMR analysis;
(viii) HPLC were run under 2 different conditions:
1) on a TSK Gel super ODS 2 μM 4.6 mm×5 cm column, eluting with a gradient of methanol in water (containing 1% acetic acid) 20 to 100% in 5 minutes. Flow rate 1.4 ml/minute. Detection: U.V. at 254 nm and light scattering detections;
2) on a TSK Gel super ODS 2 μM 4.6 mm×5 cm column, eluting with a gradient of methanol in water (containing 1% acetic acid) 0 to 100% in 7 minutes. Flow rate 1.4 ml/minute. Detection: U.V. at 254 nm and light scattering detections.
(ix) petroleum ether refers to that fraction boiling between 40–60° C.
(x) the following abbreviations have been used:
DMF N,N-dimethylformamide
DMSO dimethylsulphoxide
TFA trifluoroacetic acid
NMP 1-methyl-2-pyrrolidinone
THF tetrahydrofuran
HMDS 1,1,1,3,3,3-hexamethyldisilazane
HPLC RT HPLC retention time
DEAD diethyl azodicarboxylate
DMA dimethylacetamide
DMAP 4-dimethylaminopyridine

EXAMPLE 1

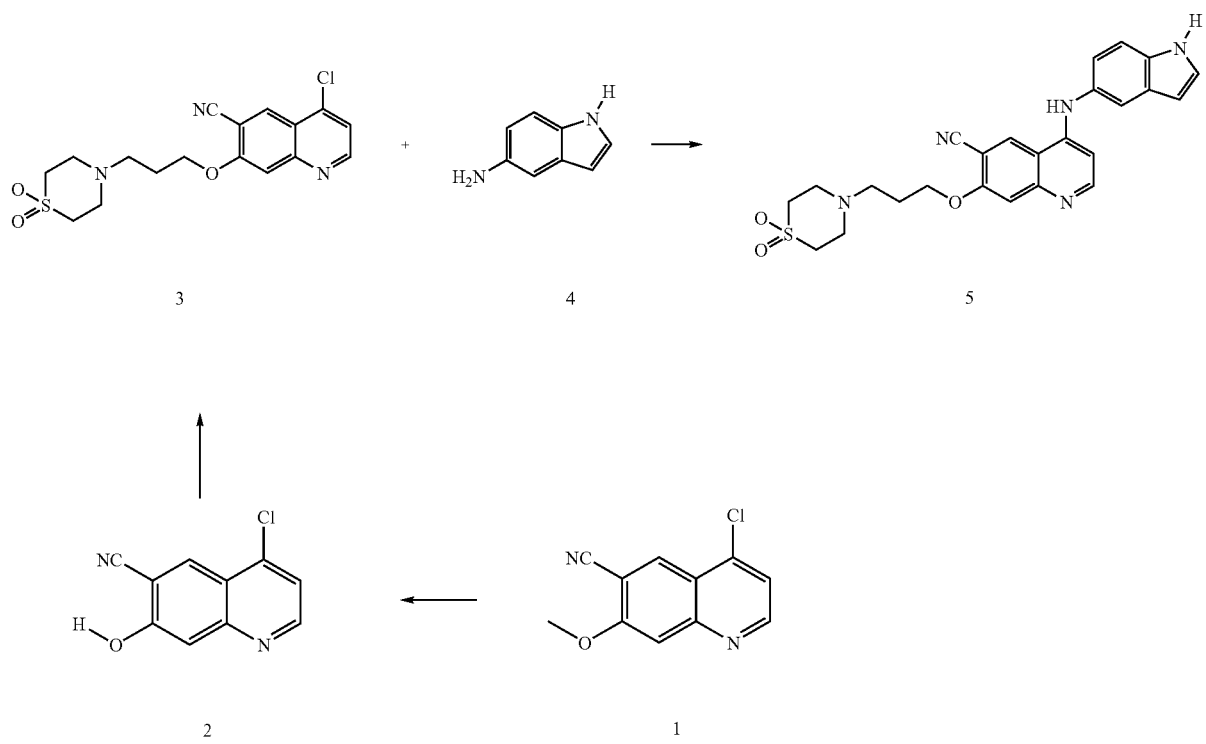

A solution of 4-chloro-6-cyano-7-(3-(1,1-dioxothiomorpholino)propoxy)quinoline (80 mg, 0.21 mmol) and 5-aminoindole (33 mg, 0.25 mmol) in 2-pentanol (2.5 ml) containing 6.2N HCl in isopropanol (40 μl) was heated at 120° C. for 3 hours. After cooling, the solid was collected by filtration, washed with isopropanol followed by ether and dried under vacuum to give 6-cyano-7-(3-(1,1-dioxothiomorpholino)propoxy)-4-(indol-5-ylamino)quinoline hydrochloride (104 mg, 90%).

¹H NMR Spectrum: (DMSOd₆, CF₃COOD) 2.3–2.45 (m, 2H) 3.52 (m, 2H); 3.7 (br s, 4H); 3.9 (br s, 4H); 4.42 (m, 2H); 6.55 (d, 1H); 6.7 (d, 1H); 7.1 (m, 1H); 7.5 (m, 2H); 7.65 (m, 2H); 8.45 (dd, 1H); 9.3 (s, 1H)

MS-ESI: 476 [MH]⁺

The starting material was prepared as follows:

A mixture of 3-amino-1-propanol (650 μl, 8.4 mmol) and vinyl sulphone (1 g, 8.4 mmol) was heated at 110° C. for 45 minutes. The mixture was allowed to cool and was purified by column chromatography eluting with methylene chloride/methanol (95/5) to give 3-(1,1-dioxothiomorpholino)propan-1-ol (800 mg, 90%).

¹H NMR Spectrum: (CDCl₃) 1.7–1.8 (m, 2H); 2.73 (t, 2H); 3.06 (br s, 8H); 3.25 (s, 1H); 3.78 (t, 2H)

MS-ESI: 194 [MH]⁺

A suspension of 4-chloro-6-cyano-7-methoxyquinoline (26.7 g, 122 mmol), (prepared by an analogous procedure to that described for the starting material in Example 1 of International Application Publication No. WO 98/13350, which document is incorporated herein by reference, but using methanol instead of 2-methoxyethanol), and aluminium trichloride (50 g, 372 mmol) in benzene (600 ml) was heated at reflux for 40 minutes. After cooling the volatiles were removed under vacuum and the residue was dissolved in ethyl acetate (1.5 l) and poured onto a mixture of ice/water (1/1, 750 ml). The organic layer was separated. The aqueous layer was adjusted to pH 4.3 with 2N NaOH and extracted with ethyl acetate. The organic layers were combined, dried (MgSO₄) and evaporated. The residue was triturated with ether, collected by filtration and dried under vacuum to give 4-chloro-6-cyano-7-hydroxyquinoline (20.5 g, 82%).

¹H NMR Spectrum: (DMSOd₆) 7.5 (s, 1H); 7.65 (d, 1H); 8.6 (s, 1H); 8.8 (d, 1H)

Mass spectrum: 227 [M⁺Na]⁺

3-(1,1-Dioxothiomorpholino)propan-1-ol (283 mg, 1.46 mmol) was added to a suspension of 4-chloro-6-cyano-7-hydroxyquinoline (200 mg, 0.97 mmol) in methylene chloride (30 ml), followed by the addition of triphenylphosphine (512 mg, 1.95 mmol) and a solution of diethyl azodicarboxylate (310 μl, 1.95 mmol) in methylene chloride (700 μl) in portions. After stirring for 5 minutes at ambient temperature, the volatiles were removed under vacuum. The residue was purified by column chromatography eluting with a mixture of methanol/ethyl acetate/methylene chloride (5/50/45). After combining the fractions containing the expected product, the solvents were removed under vacuum and the residue was triturated with methanol, collected by filtration, washed with methanol and dried under vacuum to give 4-chloro-6-cyano-7-(3-(1,1-dioxothiomorpholino)propoxy)quinoline (321 mg, 87%).

¹H No Spectrum: (CDCl₃) 2.12 (m, 2H); 2.8 (t, 2H); 3.1 (s, 8H); 4.3 (t, 2H); 7.48 (d, 1H); 7.58 (s, 1H); 8.55 (s, 1H); 8.8 (s, 1H)

EXAMPLES 2–3

Using an analogous procedure to that described in Example 1, the appropriate aminoindoles were reacted with 4-chloro-6-cyano-7-(3-(1,1-dioxothiomorpholino)propoxy)quinoline to give the corresponding compounds described in Table I:

TABLE I

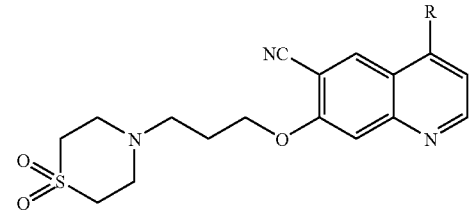

| Example | Weight (mg) | Yield (%) | MS-ESI [MH]⁺ | Note | R |
|---|---|---|---|---|---|
| 2 | 104 | 88 | 490 | a | 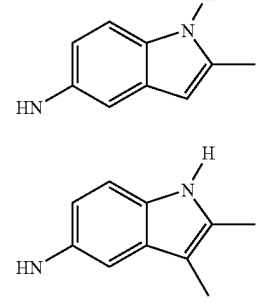 |
| 3 | 118 | 97 | 504 | b | | a) 4-Chloro-6-cyano-7-(3-(1,1-dioxothiomorpholino)propoxy)quinoline was reacted with 5-amino-2-methylindole (37 mg) to give 6-cyano-7-(3-(1,1-dioxothiomorpholino)propoxy-4-(2-methylindol-5-ylamino)quinoline hydrochloride.
¹H NMR Spectrum: (DMSOd₆, CF₃COOD) 2.4(s, 3H); 2.3–2.45(m, 2H); 3.5(t, 2H); 3.7(br s, 4H); 3.85(br s, 4H); 4.42(br s, 2H); 6.22(0.5H, partly exchanged); 6.65(d, 1H); 7.02(dd, 1H); 7.45(m, 2H); 7.5(s, 1H); 8.4(d, 1H); 9.3(s, 1H)
b) 4-Chloro-6-cyano-7-(3-(1,1-dioxothiomorpholino)propoxy)quinoline was reacted with 5-amino-2,3-dimethylindole (40 mg) to give 6-cyano-4-(2,3-dimethylindol-5-ylamino)-7-(3-(1,1-dioxothiomorpholino)propoxy)quinoline hydrochloride.
¹H NMR Spectrum: (DMSOd₆) 2.2(s, 3H); 2.35(s, 3H); 3.35–3.9(m, 10H); 4.42(t, 2H); 6.62(d, 1H); 7.02(d, 1H); 7.4(d, 1H); 7.42(s, 1H); 7.58(s, 1H); 8.4(s, 1H); 9.35(s, 1H); 11.03(s, 1H); 11.2(s, 1H)

EXAMPLE 4

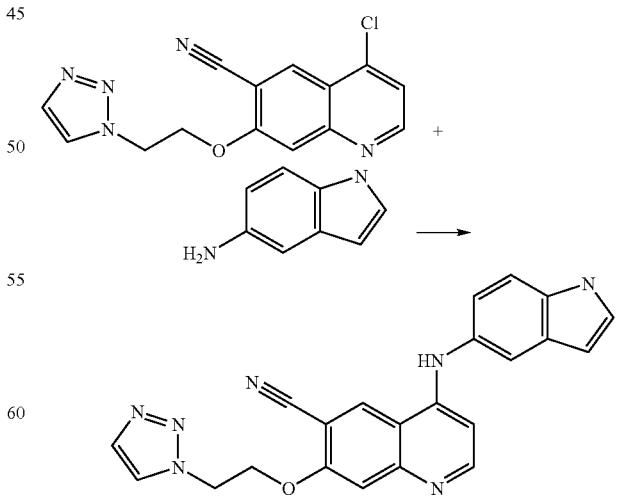

9

Using an analogous procedure to that described in Example 1, 4-chloro-6-cyano-7-(2-(1,2,3-triazol-1-yl)ethoxy)quinoline (60 mg, 0.2 mmol) was reacted with 5-aminoindole (32 mg, 0.25 mmol) to give 6-cyano-4-(indol-5-ylamino)-7-(2-(1,2,3-triazol-1-yl)ethoxy)quinoline (74 mg, 86%).

$^1$H NMR Spectrum: (DMSOd$_6$) 4.76 (t, 2H); 5.0 (t, 2H); 6.55 (s, 1H); 6.65 (d, 1H); 7.12 (d, 1H); 7.5 (m, 2H); 7.6 (d, 1H); 7.65 (s, H); 7.82 (s, 1H); 8.22 (s, 1H); 8.4 (d, 1H); 9.3 (s, 1H); 10.12 (s, 1H); 10.42 (s, 1H)

MS-ESI: 396 [MH]$^+$

The starting material was prepared as follows:

A solution of diethyl azodicarboxylate (1.15 ml, 7.3 mmol) in methylene chloride (2 ml) was added in portions to a suspension of 4-chloro-6-cyano-7-hydroxyquinoline (1 g, 4.9 mmol), (prepared as described for the starting material in Example 1), 2-(1,2,3-triazol-1-yl)-ethan-1-ol (663 mg, 5.9 mmol), (J. Antib. 1993, 46, 177), and triphenylphosphine (1.92 g, 7.3 mmol) in methylene chloride (150 ml). After stirring for 10 minutes at ambient temperature, triphenylphosphine (256 mg, 0.98 mmol) was added followed by diethyl azodicarboxylate (154 µl, 0.98 mmol). The reaction mixture was stirred for 30 minutes and the volatiles were removed under vacuum and the residue was purified by column chromatography eluting with methylene chloride/ethyl acetate/methanol (45/50/5). The fractions containing the expected product were combined and evaporated under vacuum. The residue was triturated with ether, collected by filtration, washed with ether and dried under vacuum to give 4-chloro-6-cyano-7-(2-(1,2,3-triazol-1-yl)ethoxy)quinoline (470 mg, 32%).

$^1$H NMR Spectrum: (DMSOd$_6$) 4.76 (t, 2H); 4.95 (t, 2H); 7.6–7.8 (m, 3H), 8.2 (s, 1H); 8.7 (s, 1H); 8.9 (d, 1H)

EXAMPLES 5–6

Using an analogous procedure to that described in Example 4, the appropriate aminoindoles were reacted with 4-chloro-6-cyano-7-(2-(1,2,3-triazol-1-yl)ethoxy)quinoline to give the corresponding compounds described in Table II:

TABLE II

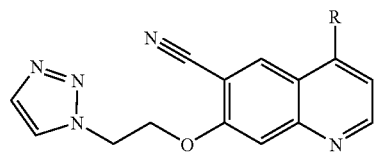

| Example | Weight (mg) | Yield (%) | MS-ESI [MH]$^+$ | Note | R |
|---|---|---|---|---|---|
| 5 | 61 | 68 | 410 | a | |
| 6 | 65 | 71 | 424 | b | |

TABLE II-continued

| Example | Weight (mg) | Yield (%) | MS-ESI [MH]$^+$ | Note | R |
|---|---|---|---|---|---| a) 4-Chloro-6-cyano-7-(2-(1,2,3-triazol-1-yl)ethoxy)quinoline was reacted with 5-amino-2-methylindole (35 mg) to give 6-cyano-4-(2-methylindol-5-ylamino)-7-(2-(1,2,3-triazol-1-yl)ethoxy)quinoline hydrochloride.
$^1$H NMR Spectrum: (DMSOd$_6$) 2.42(s, 3H); 4.75(t, 2H); 5.02(t, 2H); 6.25 (s, 1H); 6.62(d, 1H); 7.02(d, 1H); 7.5(m, 3H); 7.8(s, 1H); 8.2(s, 1H); 8.4 (d, 1H); 9.3(s, 1H); 11.1(s, 1H); 11.3(s, 1H)
b) 4-Chloro-6-cyano-7-(2-(1,2,3-triazol-1-yl)ethoxy)quinoline was reacted with 5-amino-2,3-dimethylindole (38 mg) to give 6-cyano-4-(2,3-dimethylindol-5-ylainino)-7-(2-(1,2,3-triazol-1-yl)ethoxy)quinoline hydrochloride.
$^1$H NMR Spectrum: (DMSOd$_6$) 2.15(s, 3H); 2.35(s, 3H); 4.75(t, 2H); 5.0 (t, 2H); 6.6(d, 1H); 7.0(d, 1H); 7.4(m, 2H); 7.5(s, 1H) ; 7.8(s, 1H); 8.2(s, 1H); 8.4(d, 1H); 9.3(s, 1H); 11.0(s, 1H); 11.2(s, 1H)

EXAMPLE 7

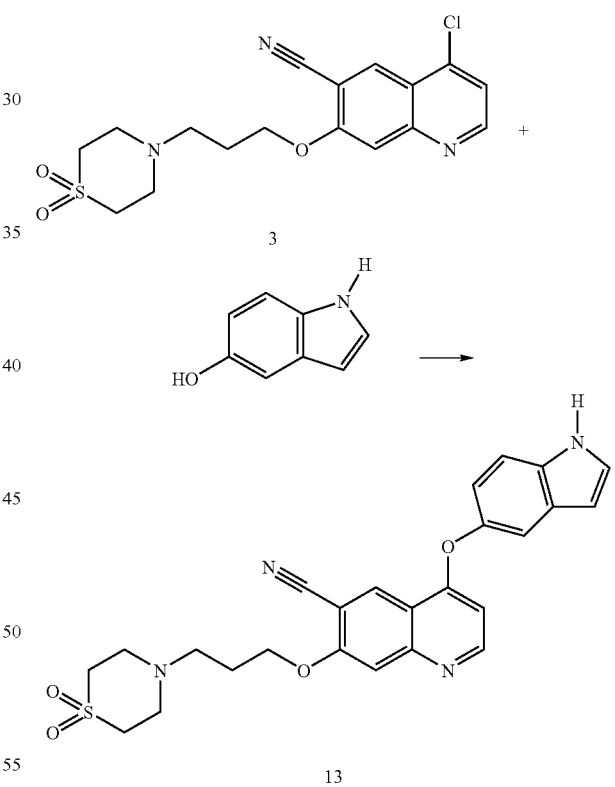

A suspension of 4-chloro-6-cyano-7-(3-(1,1-dioxothiomorpholino)propoxy)quinoline (100 mg, 0.26 mmol), (prepared as described for the starting material in Example 1), 5-hydroxyindole (42 mg, 0.32 mmol) and cesium carbonate (129 mg, 0.39 mmol) in DMF (1 ml) was stirred for 10 minutes at ambient temperature followed by 1.5 hours at 70° C. After cooling, water (5 ml) was added. The precipitate was filtered, washed with water and dried under vacuum. The solid was purified by column chromatography, eluting with methanol/methylene chloride/ethyl acetate (5/45/50) to give 6-cyano-7-(3-(1,1-dioxothiomorpholino)propoxy)-4-(indol-5-yloxy)quinoline (28 mg, 22%).

¹H NMR Spectrum: (DMSOd₆) 2.05 (m, 2H); 2.75 (m, 2H); 2.95 (br s, 4H); 3.15 (br s, 4H); 4.4 (t, 2H); 6.48 (d, 1H); 6.5 (s, 1H); 7.02 (d, 1); 7.5 (br s, 2H); 7.55 (d, 1H); 7.65 (s, 1H); 8.7 (d, 1H); 8.85 (s, 1H); 11.35 (s, 1H)

MS-ESI: 477 [MH]⁺

EXAMPLE 8

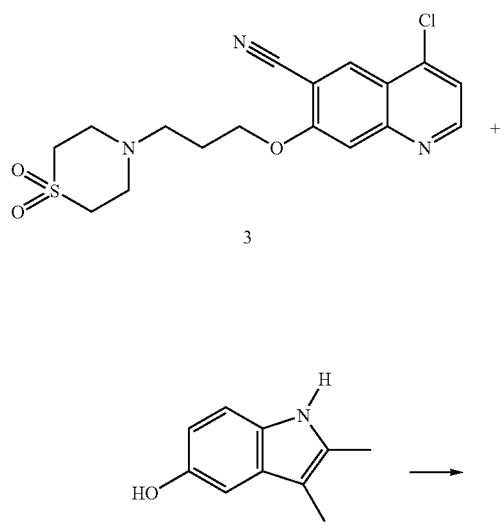

3

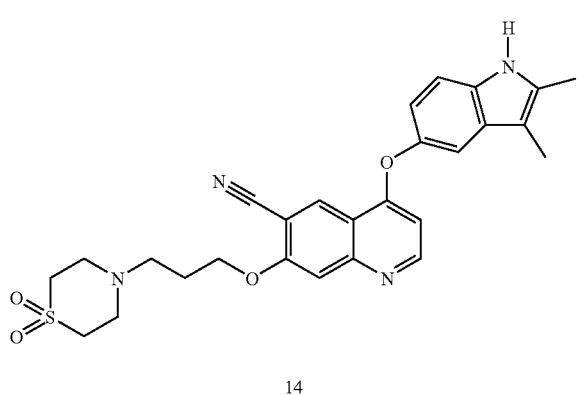

14

Using an analogous procedure to that described in Example 7, 4chloro-6-cyano-7-(3-(1,1-dioxothiomorpholino)propoxy)quinoline (100 mg, 0.26 mmol) was reacted with 2,3-dimethyl-5-hydroxyindole (51 mg, 0.32 mmol), (Arch. Pharm. 1972, 305, 159), to give 6-cyano-4-(2,3-dimethylindol-5-yloxy)-7-(3-(1,1-dioxothiomorpholino)propoxy)quinoline (85 mg, 64%).

¹H NMR Spectrum: (DMSOd₆) 2.05 (t, 2H); 2.15 (s, 3H); 2.35 (s, 3H); 2.75 (t, 2H); 2.95 (br s, 4H); 3.15 (br s, 4H); 4.4 (t, 2H); 6.45 (d, 1H); 6.9 (d, 1H); 7.3 (s, 1H); 7.4 (d, 1H); 7.65 (s, 1H); 8.7 (d, 1H); 8.8 (s, 1H); 10.9 (s, 1H)

MS-ESI: 505 [MH]⁺

EXAMPLE 9

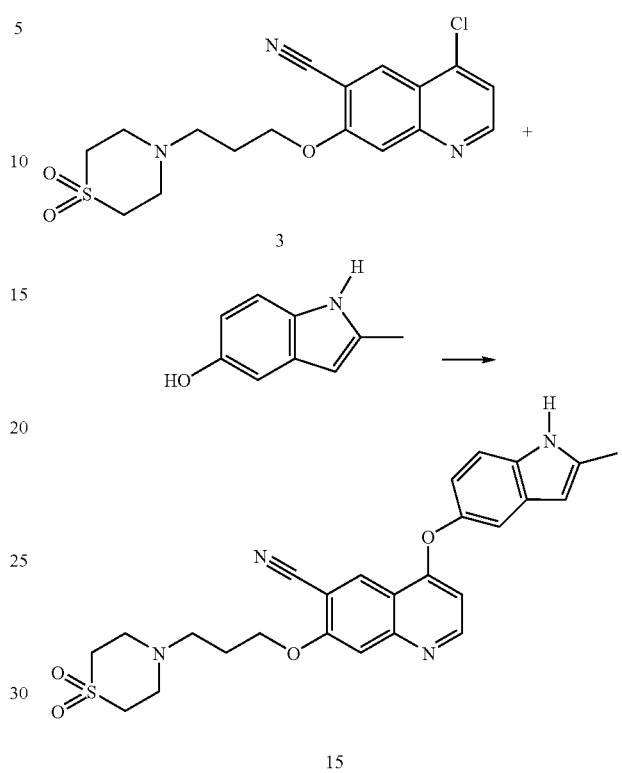

A suspension of 4-chloro-6-cyano-7-(3-(1,1-dioxothiomorpholino)propoxy)quinoline (100 mg, 0.26 mmol), (prepared as described for the starting material in Example 1), 5-hydroxy-2-methylindole (46 mg, 0.32 mmol) and cesium carbonate (129 mg, 0.39 mmol) in DMF (1 ml) was stirred for 10 minutes at ambient temperature followed by 1.5 hours at 70° C. After cooling, water (5 ml) was added. The mixture was extracted with ethyl acetate. The organic layer was separated, washed with water, brine, dried (MgSO₄) and evaporated. The residue was purified by column chromatography eluting with methanol/methylene chloride/ethyl acetate (5/45/50) to give 6cyano-7-(3-(1,1-dioxothiomorpholino)propoxy)-4-(2-methylindol-5-yloxy)quinoline (30 mg, 23%).

¹H NMR Spectrum: (DMSOd₆) 2.0 (m, 2H); 2.4 (s, 3H); 2.7 (t, 2H); 2.9 (br s, 4H); 3.1 (br s, 4H); 4.35 (t, 2H); 6.15 (s, 1H); 6.4 (d, 1H); 6.9 (dd, 1H); 7.3 (s, 1H); 7.4 (d, 1H); 7.6 (s, 1H); 8.65 (d, 1H); 8.8 (s, 1H); 11.12 (s, 1H)

MS-ESI: 491 [MH]⁺

EXAMPLE 10

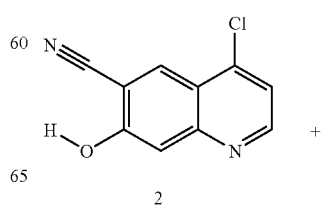

2

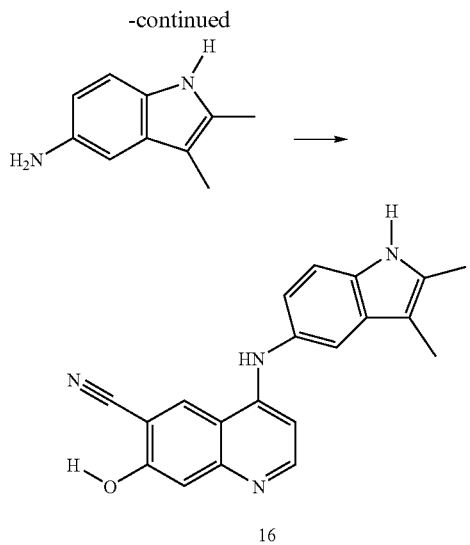

16

A solution of 4-chloro-6-cyano-7-hydroxyquinoline (852 mg, 4.2 mmol), (prepared as described for the starting material in Example 1), and 5-amino-2,3-dimethylindole (800 mg, 5 mmol) in isopropanol (25 ml) containing 6.2N HCl in isopropanol was heated at 80° C. for 2 hours. After cooling, the solid was collected by filtration, washed with isopropanol followed by ether and dried under vacuum. The solid was partitioned between acetonitrile/ethyl acetate (1/1) and water. The pH of the aqueous layer was adjusted to 7–8 with saturated aqueous sodium hydrogen carbonate followed by 1N citric acid. The organic layer was separated, washed with water, brine, dried (MgSO$_4$) and evaporated to give 6-cyano-4-(2,3-dimethylindol-5-ylamino)-7-hydroxyquinoline (650 mg, 47%).

$^1$H NMR Spectrum: (DMSOd$_6$) 2.15 (s, 3H); 2.35 (s, 3H); 6.25 (br s, 1H); 6.9 (d, 1H); 7.3 (m, 2H); 8.05 (br s, 1H); 8.8 (br s, 1H); 9.3–9.7 (br s, 1H); 10.8 (br s, 1H)

MS-ESI: 329 [MH]$^+$

EXAMPLE 11

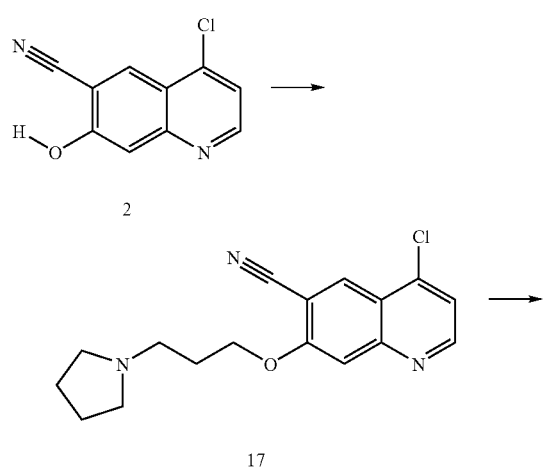

A suspension of 4-chloro-6-cyano-7-(3-(pyrrolidin-1-yl)propoxy)quinoline (500 mg, 1.58 mmol), 4-fluoro-5-hydroxy-2-methylindole (314 mg, 1.9 mmol) and cesium carbonate (775 mg, 2.38 mmol) in DMF (15 ml) was heated at 95° C. for 2 hours. After removal of the volatiles by evaporation under vacuum, the residue was dissolved in methylene chloride and poured onto a column of silica and eluted with a mixture of methylene chloride/methanol (90/10) followed by methylene chloride/methanol/methanol saturated with ammonia (88/10/2). The fractions containing the expected product were combined and evaporated to give 6-cyano-4-(4-fluoro-2-methylindol-5-yloxy)-7-(3-(pyrrolidin-1-yl)propoxy)quinoline (558 mg, 79%).

$^1$H NMR Spectrum: (DMSOd$_6$) 1.7 (br s, 4H); 2.05 (m, 2H); 2.45 (s, 3H); 2.55 (s, 4H); 2.65 (t, 2H); 4.38 (t, 2H); 6.3 (s, 1H); 6.48 (d, 1H); 7.05 (dd, 1H); 7.25 (d, 1H); 7.62 (s, 1H); 8.72 (d, 1H); 8.85 (s, 1H)

MS-ESI: 445 [MH]$^+$

The starting material was prepared as follows:

Pyrrolidine (50 g, 700 mmol), 3-chloropropanol (58.5 ml, 700 mmol) and potassium carbonate (145 g, 1.05 mol) were refluxed in acetonitrile (1 l) for 20 hours. Upon cooling to ambient temperature the precipitate was filtered off and rinsed with acetonitrile. The solvent was evaporated off and the residual oil purified by distillation under vacuum to give 3-(pyrrolidin-1-yl)propan-1-ol (62.1 g, 69%).

$^1$H NMR Spectrum: (CDCl$_3$) 1.75 (m, 6H); 2.55 (m, 4H); 2.75 (t, 2H); 3.85 (t, 2H); 5.50 (br s, (1H)

To a suspension of 4-chloro-6-cyano-7-hydroxyquinoline (10.22 g, 50 mmol), (prepared as described for the starting material in Example 1), 3-(pyrrolidin-1-yl)propan-1-ol (8.1 ml, 60 mmol) and triphenylphosphine (26.2 g, 100 mmol) in methylene chloride (200 ml) was added diethyl azodicarboxylate (16.4 ml, 100 mmol) in portions. After stirring the reaction mixture for 2 hours at ambient temperature, the volatiles were removed under vacuum and the residue was purified by column chromatography eluting with ethyl acetate/methylene chloride (1/1) followed by methanol/ethyl acetate/methylene choride (1/4/5 followed by 1/0/9) followed by methanol saturated with ammonia/methylene chloride (1/9 followed by 2/8). The fractions containing the expected product were combined and the volatiles were removed under vacuum. The residue was triturated with ether, collected by filtration, washed with ether and dried under vacuum to give 4-chloro-6-cyano-7-(3-(pyrrolidin-1-yl)propoxy)quinoline (14.3 g, 90%).

$^1$H NMR Spectrum: (DMSOd$_6$) 1.8–2.0 (m, 2H); 2.0–2.15 (m, 2H); 2.2–2.3 (m, 2H); 3.05–3.2 (m, 2H); 3.35–3.45 (t, 2H); 3.68 (m, 2H); 4.45 (t, 2H); 7.74 (s, 1H); 7.77 (d, 1H); 8.73 (s, 1H); 8.96 (d, 1H)

To a solution of 2-fluoro-4-nitroanisole (9.9 g, 58 mmol) and 4-chlorophenoxyacetonitrile (10.7 g, 64 mmol) in DMF (50 ml) cooled at −15° C. was added potassium tert-butoxide (14.3 g, 127 mmol) in DMF (124 ml). After stirring for 30 minutes at −15° C., the mixture was poured onto cooled 1N hydrochloric acid. The mixture was extracted with ethyl acetate. The organic layer was washed with 1N sodium hydroxide, brine, dried (MgSO$_4$) and evaporated. The residue was purified by column chromatography eluting with methylene chloride. The fractions containing the expected product were combined and evaporated. The residue was dissolved in ethanol (180 ml) and acetic acid (24 ml) containing 10% palladium on charcoal (600 mg) and the mixture was hydrogenated under 3 atmospheres pressure for 2 hours. The mixture was filtered, and the volatiles were removed under vacuum. The residue was partitioned between ethyl acetate and water. The organic layer was separated, and washed with saturated sodium hydrogen carbonate followed by brine, dried (MgSO$_4$) and evaporated. The residue was purified by column chromatography eluting with methylene chloride to give a mixture of 4-fluoro-5-methoxyindole and 6-fluoro-5-methoxyindole (5.64 g, 59%) in a ratio 1/2.

$^1$H NMR Spectrum: (DMSOd$_6$) 3.85 (s, 3H); 6.38 (s, 1H, 6-Fluoro); 6.45 (s, 1H; 4-Fluoro); 6.9–7.4 (m, 3H)

A solution of 4-fluoro-5-methoxyindole and 6-fluoro-5-methoxyindole in a ratio 1/2 (496 mg, 3 mmol), di-tertbutyl dicarbonate (720 mg, 3.3 mmol) in acetonitrile (12 ml) containing DMAP (18 mg, 0.15 mmol) was stirred at ambient temperature for 24 hours. The volatiles were removed under vacuum. The residue was dissolved in ethyl acetate, washed with 1N hydrochloric acid, followed by water, brine, dried (MgSO$_4$) and evaporated to give a mixture of 4-fluoro-5-methoxy-1-tert-butoxycarbonylindole and 6-fluoro-5-methoxy-1-tert-butoxycarbonylindole in a ratio 1/2 (702 mg, 88%).

$^1$H NMR Spectrum: (DMSOd$_6$) 1.65 (s, 9H); 3.9 (s, 3H); 6.6 (d, 1H, 6-fluoro); 6.72 (d, 1H, 4-fluoro); 7.2 (t, 1H, 6-fluoro); 7.4 (d, 1H, 4-fluoro); 7.62 (d, 1H, 6-fluoro); 7.68 (d, 1H, 4-fluoro); 7.78 (s, 1H, 4-fluoro); 7.85 (s, 1H, 6-fluoro)

To a solution of 4-fluoro-5-methoxy-1-tert-butoxycarbonylindole and 6-fluoro-5-methoxy-1-tert-butoxycarbonylindole in a ratio 1/2 (8.1 g, 30.5 mmol) in THF (100 ml) cooled at −65° C. was added tert-butyllithium (1.7 M) (23 ml, 35.7 mmol). After stirring for 4 hours at −70° C., methyl iodide (8.66 g, 61 mmol) was added and the mixture was left to warm-up to ambient temperature. Water was added and the mixture was extracted with ether. The organic layer was washed with water, brine, dried (MgSO$_4$) and evaporated and was used directly in the next step.

The crude product was dissolved in methylene chloride (100 ml) and TFA (25 ml) was added. After stirring for 1 hour at ambient temperature, the volatiles were removed under vacuum. The residue was dissolved in ethyl acetate and the organic layer was washed with 1N sodium hydroxide, followed by water, brine, dried (MgSO$_4$) and evaporated. The residue was purified by column chromatography, eluting with ethyl acetate/petroleum ether (3/7) to give 6-fluoro-5-methoxy-2-methylindole (1.6 g) and 4-fluoro-5-methoxy-2-methylindole (0.8 g, 48%).

6-fluoro-5-methoxy-2-methylindole:

MS-ESI: 180 [MH]$^+$ $^1$H NMR Spectrum: (DMSOd$_6$) 2.35 (s, 3H); 3.8 (s, 3H); 6.05 (s, 1); 7.1 (s, 1H); 7.12 (s, 1H); 10.8 (s, 1H)

4-fluoro-5-methoxy-2-methylindole:

MS-ESI: 180 [MH]$^+$ $^1$H NMR Spectrum: (DMSOd$_6$) 2.35 (s, 3H); 3.8 (s, 3H); 6.15 (s, 1H); 6.9 (t, 1H); 7.05 (d, 1H); 11.0 (s, 1H)

To a solution of 4-fluoro-5-methoxy-2-methylindole (709 mg, 3.95 mmol) in methylene chloride (9 ml) cooled at −30° C. was added a solution of boron tribromide (2.18 g, 8.7 mmol) in methylene chloride (1 ml). After stirring for 1 hour at ambient temperature, the mixture was poured onto water and was diluted with methylene chloride. The pH of the aqueous layer was adjusted to 6. The organic layer was separated, washed with water, brine, dried (MgSO$_4$) and evaporated. The residue was purified by column chromatography, eluting with ethyl acetate/petroleum ether (3/) to give 4-fluoro-5-hydroxy-2-methylindole (461 mg, 70%).

MS-ESI: 166 [MH]$^+$ $^1$H NMR Spectrum: (DMSOd$_6$) 2.35 (s, 3H); 6.05 (s, 1H); 6.65 (dd, 1H); 6.9 (d, 1H); 8.75 (s, 1); 10.9 (s, 1H)

$^{13}$C NMR Spectrum: (DMSOd$_6$) 13.5; 94,0; 106,0; 112; 118.5 (d); 132 (d); 136 (d); 136.5; 142.5 (d)

Alternatively the 4-fluoro-5-hydroxy-2-methylindole may be prepared as follows:

To a suspension of sodium hydride (5.42 g, 226 mmol) (prewashed with pentane) in THF (100 ml) cooled at 10° C. was added ethyl acetoacetate (29.4 g, 226 mmol) while keeping the temperature below 15° C. After completion of addition, the mixture was further stirred for 15 minutes and cooled to 5° C. A solution of 1,2,3-trifluoro-4-nitrobenzene (20 g, 113 mmol) in THF (150 ml) was added while keeping the temperature below 5° C. The mixture was then left to warm up to ambient temperature and stirred for 24 hours. The volatiles were removed under vacuum and the residue was partitioned between ethyl acetate and 2N aqueous hydrochloric acid. The organic layer was washed with water, brine, dried (MgSO$_4$) and evaporated. The residue was dissolved in concentrated hydrochloric acid (650 ml) and acetic acid (600 ml) and the mixture was refluxed for 15 hours. After cooling, the volatiles were removed under vacuum and the residue was partitioned between aqueous sodium hydrogen carbonate (5%) and ethyl acetate. The organic layer was washed with sodium hydrogen carbonate, water, brine, dried (MgSO$_4$) and evaporated. The residue was purified by column chromatography eluting with ethyl acetate/petroleum ether (75/25) to give 3-acetylmethyl-1,2-difluoro-4-nitrobenzene (17.5 g, 72%).

$^1$H NMR Spectrum: (CDCl$_3$) 2.4 (s, 3H); 4.25 (s, 2H); 7.25 (dd, 1H); 8.0 (dd, 1H)

A solution of 3-acetylmethyl-1,2-difluoro-4-nitrobenzene (500 mg, 2.3 mmol) in methylene chloride (5 ml) containing montmorillonite K10 (1 g) and trimethyl orthoformate (5 ml) was stirred for 24 hours at ambient temperature. The solid was filtered, washed with methylene chloride and the filtrate was evaporated to give 1,2-difluoro-3-(2,2-dimethoxypropyl)-4-nitrobenzene (534 mg, 88%).

$^1$H NMR Spectrum: (CDCl$_3$) 1.2 (s, 3H); 3.2 (s, 6H); 3.52 (s, 2H); 7.18 (dd, 1H); 7.6 (m, 1H)

To a solution of benzyl alcohol (221 mg, 2.05 mmol) in DMA (1.5 ml) was added 60% sodium hydride (82 mg, 2.05 mmol). The mixture was stirred for 1 hour at ambient temperature. A solution of 1,2-difluoro-3-(2,2-dimethoxypropyl)-4-nitrobenzene (534 mg, 2.05 mmol) in DMA (1.5 ml) was added and the mixture was stirred for 3 hours at ambient temperature. The mixture was diluted with 1N hydrochloric acid (10 ml) and extracted with ethyl acetate. The organic layer was evaporated and the residue was dissolved in THF (2 ml) and 6N hydrochloric acid (0.3 ml) was added. The mixture was stirred for 1 hour at ambient temperature and the solvents were removed under vacuum. The residue was partitioned between ethyl acetate and water. The organic layer was separated, washed with brine, dried (MgSO$_4$) and evaporated. The solid was triturated with ether, filtered, washed with ether and dried under vacuum to give 3-acetylmethyl-1-benzyloxy-2-fluoro-4-nitrobenzene (350 mg, 56%).

$^1$H NMR Spectrum: (CDCl$_3$) 2.35 (s, 3H); 4.25 (s, 2H); 5.25 (s, 2H); 7.0 (dd, 1H); 7.32–7.5 (m, 5H); 8.0 (dd, 1H)

A solution of 3-acetylmethyl-1-benzyloxy-2-fluoro-4-nitrobenzene (300 mg, 0.99 mmol) in ethanol (10 ml) and acetic acid (1 ml) containing 10% palladium on charcoal (30 mg) was hydrogenated at 2 atmospheres pressure for 2 hours. The mixture was filtered and the filtrate was evaporated. The residue was dissolved in ethyl acetate and the organic layer was washed with aqueous sodium hydrogen carbonate, brine and evaporated to give 4-fluoro-5-hydroxy-2-methylindole. The residue was purified by column chromatography eluting with ethyl acetate/petroleum ether (3/7) to give 4-fluoro-5-hydroxy-2-methylindole (63 mg, 30%). Analytical data as above.

Alternatively the 4-fluoro-5-methoxy-2-methylindole can be prepared as follows:

A solution of sodium methoxide (freshly prepared from sodium (1.71 g) and methanol (35 ml)) was added to a solution of 1,2-difluoro-3-(2,2-dimethoxypropyl)-4-nitrobenzene (16.2 g, 62 mmol), (prepared as described above), in methanol (200 ml) cooled at 5° C. The mixture was left to warm to ambient temperature and was stirred for 3 days. The volatiles were removed under vacuum and the residue was partitioned between ethyl acetate and 2N hydrochloric acid (1 ml). The organic layer was concentrated to a total volume of 100 ml and THF (100 ml) and 6N hydrochloric acid (25 ml) were added. The mixture was stirred for 1 hour at ambient temperature. The volatiles were removed under vacuum and the residue was partitioned between ethyl acetate and water. The organic layer was separated, washed with water, brine, dried (MgSO$_4$) and evaporated. The residue was purified by column chromatography eluting with ethyl acetate/petroleum ether (3/7) to give 3-acetylmethyl-2-fluoro-1-methoxy-4-nitrobenzene (12.7 g, 90%).

MS-ESI: 250 [MNa]+

$^1$H NMR Spectrum: (CDCl$_3$) 2.38 (s, 3H); 4.0 (s, 3H); 4.25 (s, 2H); 7.0 (dd, 1H); 8.05 (d, 1H)

To a solution of 3-acetylmethyl-2-fluoro-1-methoxy-4-nitrobenzene (11.36 g, 50 mmol) in acetone (200 ml) was added 4M aqueous ammonium acetate (700 ml) followed by a solution of titanium trichloride (15% in water, 340 ml) dropwise. The mixture was stirred for 10 minutes at ambient temperature and the mixture was extracted with ether. The organic layer was washed with 0.5N aqueous sodium hydroxide followed by water, brine, dried MgSO$_4$) and the volatiles were removed under vacuum. The residue was purified by column chromatography eluting with methylene chloride to give 4-fluoro-5-methoxy-2-methylindole (8.15 g, 90%).

$^1$H NMR Spectrum: (DMSO) 2.35 (s, 3H); 3.8 (s, 3H); 6.1 (s, 1H); 6.85 (dd, 1H); 7.02 (d, 1H)

Cleavage of 4-fluoro-5-methoxy-2-methylindole with boron tribromide to give 4-fluoro-5-hydroxy-2-methylindole is described above.

EXAMPLE 12

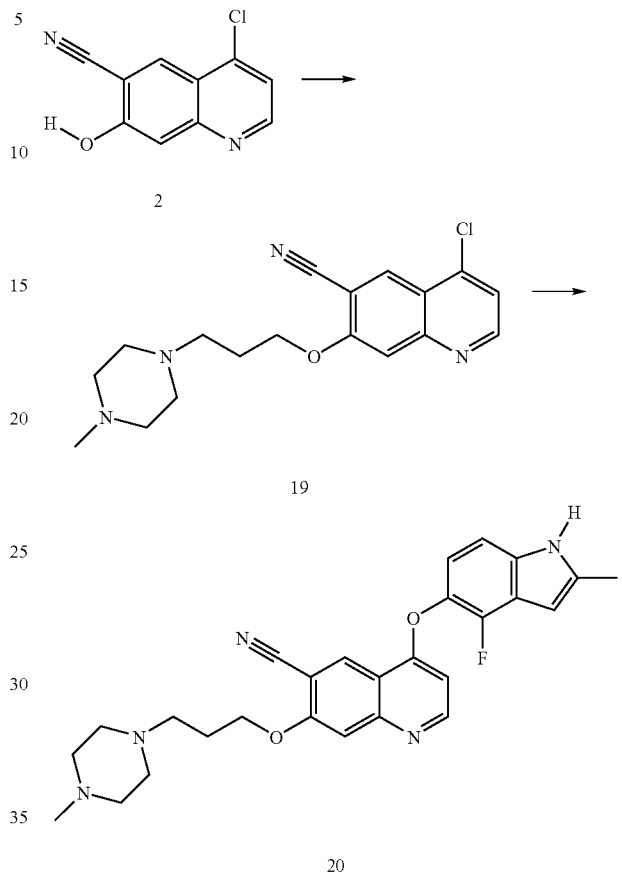

Using an analogous procedure to that described in Example 11, 4-chloro-6-cyano-7-(3-(4-methylpiperazin-1-yl)propoxy)quinoline (500 mg, 1.45 mmol) was reacted with 4-fluoro-5-hydroxy-2-methylindole (287 mg, 1.74 mmol), (prepared as described for the starting material in Example 11), in DMF (1 ml) to give 6-cyano-4-(4-fluoro-2-methylindol-5-yloxy)-7-(3-(4-methylpiperazin-1-yl)propoxy)quinoline (304 mg, 44%).

$^1$H NMR Spectrum: (DMSOd$_6$, CF$_3$COOD) 2.3–2.4 (m, 2H); 2.4 (s, 3H); 2.97 (s, 3H); 3.3–4.1 (m, 8H); 3.5 (m, 2H); 4.5 (m, 2H); 6.3 (s, 0.5 H, partly exchanged); 7.02 (d, 1H); 7.05 (dd, 1H); 7.3 (d, 1H); 7.82 (s, 1H); 9.1 (d, 1H); 9.22 (s, 1H)

MS-ESI: 474 [MM]+

The starting material was prepared as follows:

Using an analogous procedure to that described for the preparation of 4-chloro-6-cyano-7-(3-(pyrrolidin-1-yl)propoxy)quinoline, (starting material in Example 11), 4-chloro-6-cyano-7-hydroxyquinoline (8.2 g, 40 mmol), (prepared as described for the starting material in Example 1), was reacted with 1-(3-hydroxypropyl)-4-methylpiperazine (7.6 g, 48 mmol) to give 4-chloro-6-cyano-7-(3-(4-methylpiperazin-1-yl)propoxy)quinoline (12.4 g, 90%).

$^1$H NMR Spectrum: (DMSOd$_6$, CF$_3$COOD) 2.3 (m, 2H); 2.9 (s, 3H); 3.45 (t, 2H); 3.2–3.9 (m, 10H); 4.42 (t, 2H); 7.75 (m, 2H); 8.69 (s, 1H); 8.92 (d, 1H)

MS-ESI: 345–347 [MH]+

3-Bromopropan-1-ol (20 ml, 20 mmol) was added dropwise to a solution of 1-methylpiperazine (29 ml, 26 mmol) in ethanol (200 ml). Potassium carbonate (83 gr, 60 mmol) was added and the mixture was refluxed for 20 hours. After cooling, the solid was filtered and the filtrate was evaporated. The residue was triturated with ether, filtrate and evaporated. The residue was distilled at about 60–70° C. under about 0.2 mm Hg to give 1-(3-hydroxypropyl)-4-methylpiperazine (17 g, 53%).

$^1$H NMR Spectrum: (CDCl$_3$) 1.72 (m, 2H); 2.3 (s, 3H); 2.2–2.8 (m, 8H); 2.6 (t, 2H); 3.8 (t, 2H); 5.3 (br s, 1H)

EXAMPLE 13

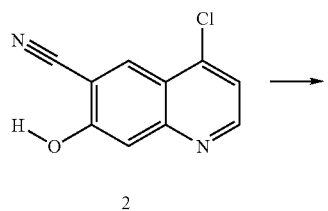

2

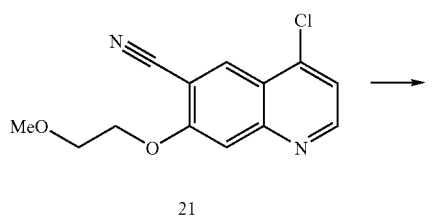

21

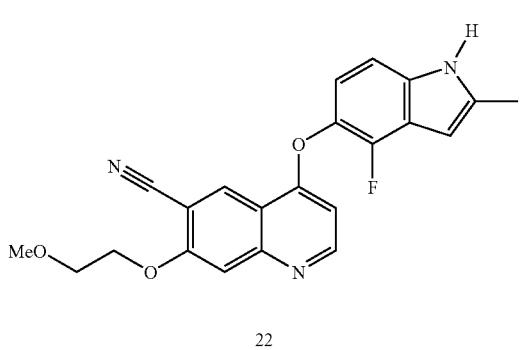

22

Using an analogous procedure to that described in Example 12, 4-chloro-6-cyano-7-(2-methoxyethoxy)quinoline (200 mg, 0.76 mmol) was reacted with 4-fluoro-5-hydroxy-2-methylindole (150 mg, 0.91 mmol), (prepared as described for the starting material in Example 11), in DMF (6 ml) to give 6-cyano-4-(4-fluoro-2-methylindol-5-yloxy)-7-(2-methoxyethoxy)quinoline (170 mg, 57%).

$^1$H NMR Spectrum: (DMSOd$_6$) 2.45 (s, 3H); 3.4 (s, 3H); 3.82 (t, 2H); 4.48 (t, 2); 6.3 (s, 1H); 6.48 (d, 1H); 7.05 (dd, 1H); 7.25 (d, 1H); 7.7 (s, 1H); 8.72 (d, 1H); 8.87 (s, 1H);

MS-ESI: 392 [MH]$^+$

EXAMPLE 14

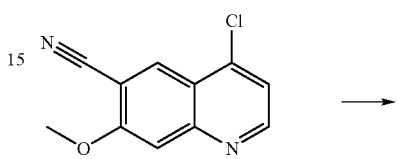

23

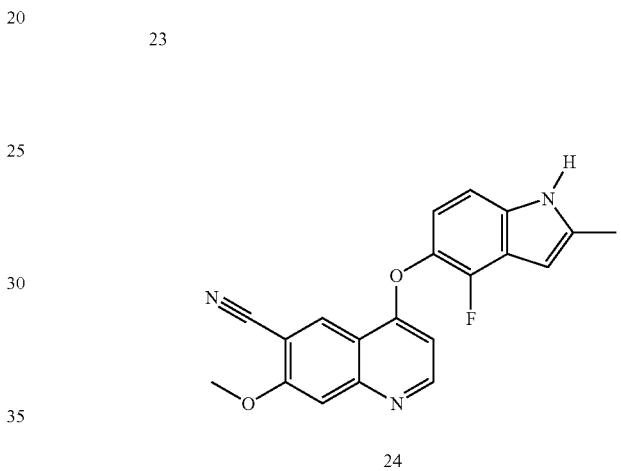

24

A suspension of 4-chloro-6-cyano-7-methoxyquinoline (200 mg, 0.91 mmol), (prepared as described for the starting material in Example 1), 4-fluoro-5-hydroxy-2-methylindole (181 mg, 1.1 mmol), (prepared as described for the starting material in Example 11), and cesium carbonate (444 mg, 1.36 mmol) in DMF (6 ml) was heated at 95° C. for 2.5 hours. After cooling, the mixture was filtered, the filtrate was evaporated under vacuum and the residue was purified by column chromatography eluting with methylene chloride, followed by methanol/ethyl acetate/methylene chloride (2/10/88 followed by 5/15/80) to give 6-cyano-4-(4-fluoro-2-methylindol-5-yloxy)-7-methoxyquinoline (111 mg, 35%).

$^1$H NMR Spectrum: (DMSOd$_6$) 2.45 (s, 3H); 4.1 (s, 3H); 6.3 (s, 1H); 6.48 (d, 1H); 7.05 (dd, 1H); 7.25 (d, 1H); 7.62 (s, 1H); 8.72 (d, 1H); 8.85 (s, 1H)

MS-ESI: 348 [MH]$^+$

EXAMPLES 15–19

Using an analogous procedure to that described in Example 14, 4-fluoro-5-hydroxy-2-methylindole was reacted with the appropriate chloroquinoline to give the corresponding compounds described in Table III:

TABLE III

[Structure: 4-(4-fluoro-2-methylindol-5-yloxy)-6-cyano-7-R-quinoline core]

| Example | Weight (mg) | Yield (%) | MS-ESI [MH]⁺ | Note | R |
|---|---|---|---|---|---|
| 15 | 116 | 42 | 462 | a | (tetrahydropyran-4-yloxy)ethoxy- |
| 16 | 141 | 51 | 454 | b | Me-SO$_2$—(CH$_2$)$_3$—O |
| 17 | 75 | 35 | 429 | c | 2-(1,2,3-triazol-1-yl)ethoxy- |
| 18 | 28 | 26 | 443 | d | 3-(1,2,3-triazol-1-yl)propoxy- |
| 19 | 29 | 39 | 509 | e | 3-(1,1-dioxothiomorpholin-4-yl)propoxy- | a 4-Fluoro-5-hydroxy-2-methylindole (119 mg) was reacted with 4-chloro-6-cyano-7-(2-(tetrahydropyran-4-yloxy)ethoxy)quinoline (200 mg), to give 6-cyano-4-(4-fluoro-2-methylindol-5-yloxy)-7-(2-(tetrahydropyran-4-yloxy)ethoxy)quinoline.
¹H NMR Spectrum: (DMSOd$_6$) 1.4–1.55 (m, 2H); 1.85–1.97(m, 2H); 2.45(s, 3H); 3.4(m, 2H); 3.7(m, 1H); 3.85(td, 2H); 3.92(m, 2H); 4.45(t, 2H); 6.3(s, 1H); 6.5(d, 1H); 7.05(dd, 1H); 7.25(d, 1H). 7.7(s, 1H); 8.72(d, 1H); 8.85(s, 1H)

The starting material was prepared as follows:

Tetrahydropyran-4-ol (19.72 g; 0.193 mol) was added dropwise (rapid addition) to a suspension of sodium hydride (8.5 g; 0.213 mol) in DMF (200 ml) under argon. The mixture was heated at 50° C. for 40 minutes then cooled to ambient temperature. 2-tert-Butoxyethyl bromide (35 g, 0.193 mol), (J. Med. Chem. 1966, 361), was added dropwise followed by sodium iodide (approximately 1 g) and 15-crown-5 (20 drops). The mixture was heated at 105° C. for 1 hour. Upon cooling to ambient temperature the mixture was poured into a saturated solution of ammonium chloride and extracted with ether (2×1 l). The organic phase was washed with water, brine, dried (MgSO$_4$) and the solvent evaporated off to give 4-(2-tert-butoxyethoxy)tetrahydropyran (25 g, 64%) as a light brown oil.
¹H NMR Spectrum: (CDCl$_3$) 1.20 (s, 9H); 1.60 (m, 2H); 1.90 (m, 2H); 3.50 (m, 7H); 3.95 (m, 2H)

4-(2-tert-Butoxyethoxy)tetrahydropyran (24 g, 0.12 mol) was stirred in a mixture of methylene chloride/trifluoroacetic acid (150 ml/150 ml) at ambient temperature overnight. The solvents were evaporated off and the residual trifluoroacetic acid was azeotroped off with, toluene. The crude oil was purified by flash chromatography using successively petroleum ether, petroleum ether/methylene chloride (1/1) and methylene chloride. The organic phase was washed with water, brine, dried (MgSO$_4$), filtered and the solvent evaporated. Evaporation of the solvent gave 4-(2-trifluoroacetoxyethoxy)tetrahydropyran which was hydrolysed with potassium hydrogen carbonate (48 g, 0.48 mol) in methanol (700 ml) and water (300 ml) at ambient temperature for 3 hours. The solution was neutralised to pH 7 and the solvents evaporated off. The residue was extracted with ethyl acetate, the organic phase washed with water and brine, dried (MgSO$_4$) and the solvent evaporated off to give 4-(2-hydroxyethoxy)tetrahydropyran (6 g, 35%) as a light brown oil.

¹H NMR Spectrum: (CDCl$_3$, acetic acid) 1.60 (m, 2H); 1.95 (m, 2H); 3.45 (m, 2H); 3.55 (m, 1H); 3.60 (t, 2H); 3.75 (t, 2H); 3.95 (m, 2H)

To a suspension of 4-chloro-6-cyano-7-hydroxyquinoline (400 mg, 1.95 mmol), (prepared as described for the starting material in Example 1), 4-(2-hydroxyethoxy)tetrahydropyran (371 mg, 2.54 mmol) and triphenylphosphine (820 mg, 3.12 mmol) in methylene choride (15 ml) was added diethyl azodicarboxylate (492 μl, 3.12 mmol) in portions. After stirring for 30 minutes, triphenylphosphine (512 mg, 1.95 mmol), 4-(2-hydroxyethoxy)-tetrahydropyran (142 mg, 0.98 mmol) and diethyl azodicarboxylate (308 μl, 1.95 mmol) were added. The volatiles were removed under vacuum and the residue was purified by column chrolatography eluting with methylene chloride/ethyl actetate/methanol (60/40/0 followed by 50/50/0, 40/60/0, 60/39/1, 60/38/2 and 50/46/4) to give 4-chloro-6-cyano-7-(2-(tetrahydropyran-4-yloxy)ethoxy)quinoline (519 mg, 65%).

¹H NMR Spectrum: (CDCl₃) 1.6–1.75 (m, 2H); 1.9–2.05 (m, 2H); 3.5 (dt, 2H); 3.65–3.75 (m, 1H); 3.9–4.1 (m, 4H); 4.4 (t, 2H); 7.45 (d, 1H); 7.55 (s, 1H); 8.55 (s, 1H); 8.8 (d, 1H)

MS-ESI: 333 [MH]+ b) 4-Fluoro-5-hydroxy-2-methylindole (122 mg) was reacted with 4-chloro-6-cyano-7-(3-methylsulphonylpropoxy)quinoline (200 mg) to give 6-cyano-4-(4-fluoro-2-methylindol-5-yloxy)-7-(3-methylsulphonylpropoxy)quinoline.

¹H NMR Spectrum: (DMSOd₆): 2.25–2.4 (m, 2H); 2.45 (s, 3H); 3.1 (s, 3H); 4.48 (t, 2H); 6.3 (s, 1H); 6.5 (d, 1H); 7.05 (dd, 1H); 7.25 (d, 1H); 7.65 (s, 1H); 8.75 (d, 1H); 8.9 (s, 1H)

The starting material was prepared as follows:

Using an analogous procedure to that described for the preparation of the starting material in Example 15, (see note a) above), 4-chloro-6-cyano-7-hydroxyquinoline (300 mg, 1.46 mmol), (prepared as described for the starting material in Example 1), was reacted with 3-(methylsulphonyl)-1-propanol (263 mg, 1.9 mmol) and the crude product was purified using a gradient of methylene chloride/ethyl acetate (1/1) to (2/8) to give 4-chloro-6-cyano-7-(3-methylsulphonylpropoxy)quinoline (428 mg, 90%)

¹H NMR Spectrum: (CDCl₃) 2.5 (m, 2H); 3.02 (s, 3H); 3.35 (t, 2H); 4.4 (m, 2H); 7.45 (d, 1H); 7.52 (s, 1H); 8.52 (s, 1H); 8.82 (d, 1H)

MS-ESI: 347–349 [MNa]+

A solution of 3-(methylthio)-1-propanol (5.3 g, 50 mmol) in methanol (500 ml) was added to a solution of OXONE, (trade mark of E. I. du Pont de Nemours & Co., Inc), (30 g) in water (150 ml) and the mixture stirred at ambient temperature for 24 hours. The precipitated solid was removed by filtration and the methanol removed from the filtrate by evaporation. The aqueous residue was saturated with sodium chloride and extracted with methylene chloride (4×25 ml). The aqueous residue was then saturated with ammonium chloride and extracted with ethyl acetate (4×25 ml). The extracts were combined, dried (MgSO₄) and the solvent removed by evaporation to give 3-(methylsulphonyl)-1-propanol (610 mg, 9%) as an oil.

¹H NMR Spectrum: (CDCl₃) 2.10 (m, 2H); 2.96 (s, 3H); 3.20 (t, 2H); 3.80 (t, 2H);

MS-ESI: 139 [MH]⁺

Alternatively the 3-(methylsulphonyl)-1-propanol may be prepared as follows:

m-Chloroperoxybenzoic acid (67%, 25 g, 97.2 mmol) was added in portions to 3-(methylthio)-1-propanol (5 ml, 48.6 mmol) in solution in dichloromethane. Some m-chlorobenzoic acid precipitated out and was removed by filtration. The filtrate was evaporated and the residue was purified over alumina using first dichloromethane (100%) then dichloromethane/methanol (95/5) to give 3-(methylsulphonyl)-1-propanol (4.18 g, 62%) as an oil.

c) 4-Fluoro-5-hydroxy-2-methylindole (99 mg) was reacted with 4-chloro-6-cyano-7-(2-(1,2,3-triazol-1-yl)ethoxy)quinoline (150 mg), (prepared as described for the starting material in Example 4), to give 6-cyano-4-(4-fluoro-2-methylindol-5-yloxy)-7-(2-(1,2,3-triazol-1-yl)ethoxy)quinoline.

¹H NMR Spectrum: (DMSOd₆) 2.45 (s, 3H); 4.8 (t, 2H); 4.97 (t, 2H); 6.3 (s, 1H); 6.5 (d, 1H); 7.05 (dd, 1H); 7.25 (d, 1H); 7.7 (s, 1H); 7.8 (s, 1H); 8.22 (s, 1H); 8.75 (d, 1H); 8.85 (s, 1H)

d) 4-Fluoro-5-hydroxy-2-methylindole (47 mg) was reacted with 4-chloro-6-cyano-7-(3-(1,2,3-triazol-1-yl)propoxy)quinoline (75 mg) to give 6-cyano-4-(4-fluoro-2-methylindol-5-yloxy)-7-(3-(1,2,3-triazol-1-yl)propoxy)quinoline.

¹H NMR Spectrum: (DMSOd₆) 2.45 (s, 3H); 2.45–2.5 (m, 2H) 4.32 (t, 2H); 4.68 (t, 2H); 6.32 (s, 1H); 6.5 (d, 1H); 7.05 (dd, 1H); 7.25 (d, 1H); 7.65 (s, 1H); 7.8 (s, 1H); 8.25 (s, 1H); 8.75 (d, 1H); 8.9 (s, 1H)

The starting material was prepared as follows:

Using an analogous procedure to that described for the preparation of the starting material in Example 15 (see note a) above), 4-chloro-6-cyano-7-hydroxyquinoline (300 mg, 1.46 mmol), (prepared as described for the starting material in Example 1), was reacted with 3-(1,2,3-triazol-1-yl)propan-1-ol (242 mg, 1.9 mmol) to give 4chloro-6-cyano-7-(3-(1,2,3-triazol-1-yl)propoxy)quinoline (349 mg, 86%).

¹H NMR Spectrum: (CDCl₃) 2.6 (m, 2H); 4.2 (t, 2H); 4.75 (t, 2H); 7.45 (d, 1H); 7.45 (s, 1H); 7.65 (s, 1H); 7.7 (s, 1H); 8.6 (s, 1H); 8.8 (d, 1H)

MS-ESI: 314–316 [MH]+

A mixture of 1,2,3-triazole (5 g, 72.4 mmol) and ethyl acrylate (7.8 ml, 72.4 mmol) containing pyridine (50 drops) was heated at 90° C. for 4 hours. After cooling, the volatiles were removed under vacuum and the residue was purified by column chromatography eluting with methylene chloride/ether to give ethyl (1H-1,2,3-triazol-1-yl)propanoate (8.96 g, 73%).

¹H NMR Spectrum: (CDCl₃) 1.25 (t, 3H); 2.95 (t, 2H); 4.15 (q, 2H); 4.7 (t, 2H); 7.65 (s, 1H); 7.7 (s, 1H)

A solution of ethyl (1H-1,2,3-triazol-1-yl)propanoate (8.96 g, 53 mmol) in THF (50 ml) was added dropwise to a suspension of lithium aluminium hydride (3 g, 79 mmol) in THF (250 ml) cooled at 0° C. After stirring for 1 hour at 5° C., the mixture was stirred for 1 hour at ambient temperature. The mixture was cooled at 0° C. and 4N sodium hydroxide (30 ml) was added dropwise. The mixture was filtered and the solid was washed with THF followed by ethyl acetate. The filtrate was dried (MgSO₄) and evaporated. The residue was purified by column chromatography, eluting with methylene chloride/methanol (94/6) to give 3-(1,2,3-triazol-1-yl)propan-1-ol (6.2 g, 92%).

¹H NMR Spectrum: (CDCl₃): 2.1–2.2 (m, 3H); 3.65 (m, 2H); 4.6 (t, 2H); 7.6 (s, 1H); 7.72 (s, 1H)

e) 4-Fluoro-5-hydroxy-2-methylindole (29 mg), was reacted with 4-chloro-6-cyano-7-(3-(1,1-dioxothiomorpholino)propoxy)quinoline (55 mg), (prepared as described for the starting material in Example 1), to give 6-cyano-4-(4-fluoro-2-methylindol-5-yloxy)-7-(3-(1,1-dioxothiomorpholino)propoxy)quinoline.

1H NMR Spectrum: (DMSOd₆) 2.0–2.1 (m, 2H); 2.42 (s, 3H); 2.72 (t, 2H); 2.95 (br s, 4H); 3.15 (br s, 4H); 4.38 (t, 2H); 6.3 (s, 1H); 6.45 (d, 1H); 7.05 (dd, 1H); 7.25 (d, 1H); 7.65 (s, 1H); 8.7 (d, 1H); 8.85 (s, 1H)

EXAMPLE 20

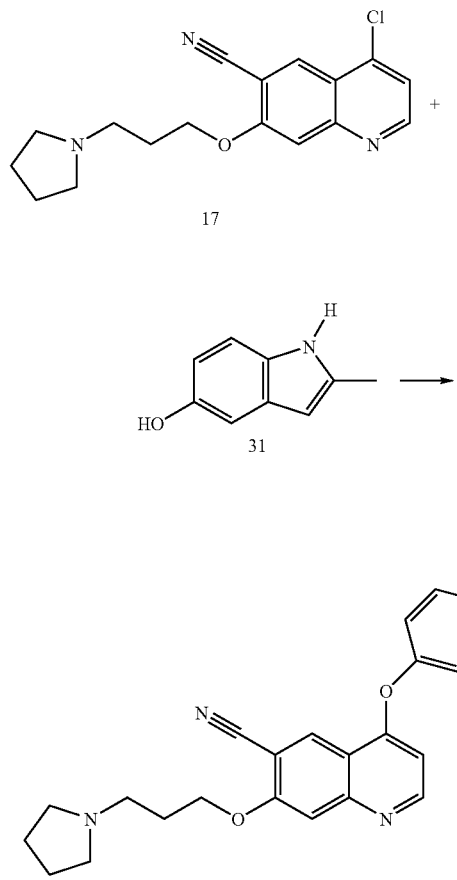

A suspension of 4-chloro-6-cyano-7-(3-(pyrrolidin-1-yl) propoxy)quinoline (150 mg, 0.48 mmol), (prepared as described for the starting material in Example 11), 5-hydroxy-2-methylindole (84 mg, 0.57 mmol) and cesium carbonate (200 mg, 0.72 mmol) in DMF (6 ml) was heated at 95° C. for 2 hours. After cooling, the mixture was filtered and the filtrate was evaporated under vacuum. The residue was purified by column chromatography eluting with methylene chloride, followed by ethyl acetate, followed by methanol/methylene chloride (1/9) followed by methylene chloride/methanol saturated with ammonia (9/1 followed by 85/15) to give 6-cyano-((2-methylindol-5-yloxy)-7-(3-(pyrrolidin-1-yl)propoxy)quinoline (112 mg, 46%).

$^{1}$H NMR Spectrum: (DMSOd$_{6}$) 1.7 (br s, 4H); 2.02 (m, 2H); 2.4 (s, 3H); 2.45 (br s, 4H); 2.62 (t, 2); 4.35 (t, 2H); 6.18 (s, 1H); 6.45 (d, 1H); 6.9 (dd, 1H); 7.3 (s, 1H); 7.4 (d, 1H); 7.6 (s, 1H); 8.68 (d, 1H),; 8.8 (s, 1H)

EXAMPLES 21–26

Using an analogous procedure to that described in Example 20, 4-chloro-6-cyano-7-(3-(pyrrolidin-1-yl)propoxy)quinoline was reacted with the appropriate hydroxyindole to give the corresponding compounds described in Table IV:

TABLE IV

| Example | Weight (mg) | Yield (%) | Note | R |
|---|---|---|---|---|
| 21 | 140 | 58 | a | 6-hydroxy-2-methylindol-yl |
| 22 | 100 | 42 | b | indol-5-yloxy |
| 23 | 108 | 43 | c | 2,3-dimethylindol-5-yloxy |
| 24 | 126 | 50 | d | 2,3-dimethylindol-5-yloxy (isomer) |
| 25 | 6 | 2 | e | 4-fluoroindol-5-yloxy |
| 26 | 20 | 8 | f | 6-fluoroindol-5-yloxy | a) 4-Chloro-6-cyano-7-(3-(pyrrolidin-1-yl)propoxy)quinoline was reacted with 6-hydroxy-2-methylindole (84 mg), (Eur. J. Med. Chem. 1975, 10, 187), to give 6-cyano-4-(2-methylindol-6-yloxy)-7-(3-(pyrrolidin-1-yl)propoxy)quinoline.
$^{1}$H NMR Spectrum: (DMSOd$_{6}$) 1.7(br s, 4H); 2.05(m, 2H); 2.4(s, 3H); 2.48(br s, 4H); 2.62(t, 2H); 4.35(t, 2H); 6.2(s, 1H); 6.48(d, 1H); 6.85(d, 1H); 7.2(s, 1H); 7.5(d, 1H); 7.6(s, 1H); 8.7(d, 1H); 8.8(s, 1H)
b) 4-Chloro-6-cyano-7-(3-(pyrrolidin-1-yl)propoxy)quinoline was reacted with 5-hydroxyindole (76 mg) to give 6-cyano-4-(indol-5-yloxy)-7-(3-(pyrrolidin-1-yl)propoxy)quinoline.
$^{1}$H NMR Spectrum: (DMSOd$_{6}$) 1.7(br s, 4H); 2.05(m, 2H); 2.45 (br s, 4H); 2.6(t, 2H); 4.35(t, 2H); 6.45(d, 1H); 6.5(s, 1H); 7.0(dd, 1H); 7.48(br s, 2H); 7.55(d, 1H); 7.6(s, 1H); 8.7(d, 1H); 8.8(s, 1H)
c) 4-Chloro-6-cyano-7-(3-(pyrrolidin-1-yl)propoxy)quinoline was reacted with 2,3-dimethyl-5-hydroxyindole (92 mg), (Arch. Pharm. 1972, 305, 159), to give 6-cyano-4-(2,3-dimethylindol-5-yloxy)-7-(3-(pyrrolidin-1-yl)propoxy)quinoline.

TABLE IV-continued

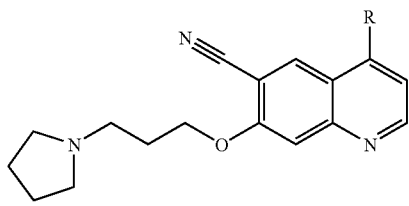

| Example | Weight (mg) | Yield (%) | Note | R |
|---|---|---|---|---|

$^1$H NMR Spectrum: (DMSOd$_6$) 1.7(br s, 4H); 2.02(m, 2H); 2.15(s, 3H); 2.35(s, 3H); 2.48(br s, 4H); 2.65(t, 2H); 4.35(t, 2H); 6.45(d, 1H); 6.9(d, 1H); 7.28(s, 1H); 7.35(d, 1H); 7.6(s, 1H); 8.68(d, 1H); 8.8(s, 1H)

d) 4-Chloro-6-cyano-7-(3-(pyrrolidin-1-yl)propoxy)quinoline was reacted with 1,2-dimethyl-5-hydroxyindole (92 mg), (Tetrahedron 1994, 50, 13433), to give 6-cyano-4-(1,2-dimethylindol-5-yloxy)-7-(3-(pyrrolidin-1-yl)propoxy)quinoline.

$^1$H NMR Spectrum: (DMSOd$_6$) 1.7(br s, 4H); 2.02(m, 2H); 2.45(s, 3H); 2.5(br s, 4H); 2.65(t, 2H); 3.7(s, 3H); 4.35(t, 2H); 6.28(s, 1H); 6.42(d, 1H); 7.0(dd, 1H); 7.35(s, 1H); 7.52(d, 1H); 7.6(s, 1H); 8.68(d, 1H); 8.8(s, 1H)

e) 4-Chloro-6-cyano-7-(3-(pyrrolidin-1-yl)propoxy)quinoline was reacted with 4-fluoro-5-hydroxyindole (86 mg). After purification by column chromatography, the residue was repurified by preparative LC-MS eluting with a gradient of water/methanol saturated with ammonia/acetonitrile (65/5/30 to 0/5/95) to give after combination of the fractions containing the expected product and removal of the volatiles, 6-cyano-4-(4-fluoroindol-5-yloxy)-7-(3-(pyrrolidin-1-yl)propoxy)quinoline.

$^1$H NMR Spectrum: (DMSOd$_6$) 1.7(br s, 4H); 2.05(m, 2H); 2.5(br s, 4H); 2.6(t, 2H); 4.35(t, 2H); 6.5(d, 1H); 6.6(s, 1H); 7.15(dd, 1H); 7.4(d, 1H); 7.52(s, 1H); 7.65(s, 1H); 8.7(d, 1H); 8.85(s, 1H)

The starting material was prepared as follows:

A mixture of 2-fluoro-4-nitrophenol (15 g, 95.5 mmol) and benzyl bromide (18 g, 105 mmol) in acetone (125 ml) containing potassium carbonate (26.5 g, 190 mmol) was refluxed for 2 hours. The volatiles were removed and the residue was partitioned between 2N hydrochloric acid and ethyl acetate. The organic layer was separated, washed with water, brine, dried (MgSO$_4$) and the volatiles were removed under vacuum. The solid was triturated with petroleum ether to give 2-fluoro-4-nitro-benzyloxybenzene (23 g, 97%).

$^1$H NMR Spectrum: (CDCl$_3$) 5.3 (s, 2H); 7.1 (t, 1H); 7.35–7.55 (m, 5H); 8.0 (m, 2H)

To a solution of potassium tert-butoxide (1.72 g, 15.4 mmol) in DMF (15 ml) cooled at −30° C., was added dropwise a solution of 2-fluoro-4-nitro-benzyloxybenzene (1.73 g, 7 mmol) and 4-chlorophenoxyacetonitrile (1.29 g, 7.7 mmol) while maintaining the temperature below −25° C. After completion of addition, the mixture was stirred for 30 minutes at −20° C. and then poured onto a mixture of cold 1N hydrochloric acid and ether. The organic layer was separated, washed with 1N sodium hydroxide, followed by water, brine, dried (MgSO$_4$). The volatiles were removed under vacuum and the residue was purified by column chromatography eluting with methylene chloride/petroleum ether (3/1) to give a mixture of 3-cyanomethyl-2-fluoro-4-nitrobenzyloxybenzene and 5-cyanomethyl-2-fluoro-4-nitrobenzyloxybenzene (1.2 g, 60%).

$^1$H NMR Spectrum: (DMSOd$_6$) 4.22 (s, 2H, 3-cyanomethyl isomer); 4.3 (s, 2H, 5-cyanomethyl isomer); 5.32 (s, 2H, 5-cyanomethyl isomer); 5.36 (s, 2H, 3-cyanomethyl isomer); 7.3–7.7 (m, 6H); 8.1 (d, 1H, 3-cyanomethyl isomer); 8.2 (d, 1H, 5-cyanomethyl isomer)

A solution of a mixture of 3-cyanomethyl-2-fluoro-4-nitrobenzyloxybenzene and 5-cyanomethyl-2-fluoro-4-nitrobenzyloxybenzene (23 g, 80.4 mmol) in ethanol (220 ml) and acetic acid (30 ml) containing 10% palladium on charcoal (600 mg) was hydrogenated under 3 atmospheres pressure until hydrogen uptake ceased. The mixture was filtered and the filtrate was evaporated under vacuum. The residue was purified on column chromatography using a Prochrom® equipment eluting with methylene chloride/petroleum ether (20/80) to give 4-fluoro-5-hydroxyindole (2.48 g) and 6-fluoro-5-hydroxyindole (3.5 g).

4-fluoro-5-hydroxyindole:

$^1$H NMR Spectrum: (DMSOd$_6$) 6.32 (s, 1H); 6.75 (dd, 1H); 7.0 (d, 1H); 7.28 (dd, 1H); 8.8 (br s, 1H); 11.05 (br s, 1H)

6-fluoro-5-hydroxyindole:

$^1$H NMR Spectrum: (DMSOd$_6$) 6.25 (s, 1H); 7.0 (d, 1); 7.12 (d, 1H); 7.2 (dd, 1H); 9.0 (br s, 1H)

f) 4-Chloro-6-cyano-7-(3-(pyrrolidin-1-yl)propoxy)quinoline was reacted with 6-fluoro-5-hydroxyindole (86 mg), (prepared as described for the preparation of the starting material in Example 25). The crude product was purified as described in the synthesis of Example 25 to give 6-cyano-4-(6-fluoroindol-5-yloxy)-7-(3-(pyrrolidin-1-yl)propoxy)quinoline.

$^1$H NMR Spectrum: (DMSOd$_6$) 1.7 (br s, 4H); 2.05 (m, 2H); 2.5 (br s, 4H); 2.65 (t, 2H); 4.35 (t, 2H); 6.5 (d, 1H); 6.55 (s, 1H); 7.48 (s, 1H); 7.5 (d, 1H); 7.62 (s, 1H); 7.65 (d, 1H); 8.7 (d, 1H); 8.85 (s, 1H)

EXAMPLE 27

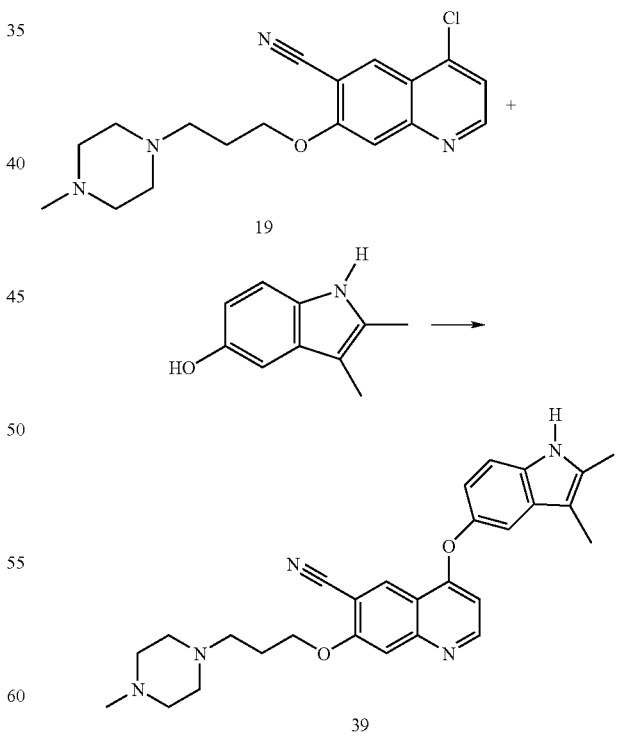

Using an analogous procedure to that described in Example 20, 4-chloro-6-cyano-7-(3-(4methylpiperazin-1-yl)propoxy)quinoline (150 mg, 0.44 mmol), (prepared as described for the starting material in Example 12), was reacted with 2,3-dimethyl-5-hydroxyindole (84 mg, 0.52 mmol), (Arch. Pharm. 1972, 305, 159), to give 6-cyano-4-(2,3-dimethylindol-5-yloxy)-7-(3-(4-methylpiperazin-1-yl)propoxy)quinoline (146 mg, 60%).

$^1$H NMR Spectrum: (DMSOd$_6$) 2.0 (m, 2H); 2.13 (s, 3H); 2.17 (s, 3H); 2.33 (s, 3H); 2.2–2.6 (m, 10 H); 4.35 (t, 2H); 6.42 (d, 1H); 6.9 (dd, 1H); 7.28 (s, 1H); 7.35 (d, 1H); 8.7 (d, 1H); 8.8 (s, 1H)

EXAMPLES 28–32

Using an analogous procedure to that described in Example 27, 4-chloro-6-cyano-7-(3-(4-methylpiperazin-1-yl)propoxy)quinoline was reacted with the appropriate hydroxyindoles to give the corresponding compounds described in Table V:

TABLE V

| Example | Weight (mg) | Yield (%) | MS-ESI [MH]$^+$ | Note | R |
|---|---|---|---|---|---|
| 28 | 121 | 51 | | a | 5-hydroxy-2-methylindole |
| 29 | 143 | 60 | | b | 6-hydroxy-2-methylindole |
| 30 | 129 | 53 | | c | 1,2-dimethyl-5-hydroxyindole |
| 31 | 12.5 | 5 | | d | 6-fluoro-5-hydroxyindole |
| 32 | 18 | 8 | | e | 5-hydroxyindole | a) 4-Chloro-6-cyano-7-(3-(4-methylpiperazin-1-yl)propoxy)quinoline was reacted with 5-hydroxy-2-methylindole (77 mg) to give 6-cyano-4-(2-methylindol-5-yloxy)-7-(3-(4-methylpiperazin-1-yl)propoxy)quinoline.
$^1$H NMR Spectrum: (DMSOd$_6$) 2.0(m, 2H); 2.15(s, 3H); 2.2–2.6 (m, 10H); 2.45(s, 3H); 4.32(t, 2H); 6.2(s, 1H); 6.45(d, 1H); 6.9(dd, 1H); 7.3(s, 1H); 7.4(d, 1H); 7.58(s, 1H); 8.7(d, 1H); 8.8(s, 1H)
b) 4-Chloro-6-cyano-7-(3-(4-methylpiperazin-1-yl)propoxy)quinoline was reacted with 6-hydroxy-2-methylindole(77 mg), (Eur. J. Med. Chem. 1975, 10, 187), to give 6-cyano-4-(2-methylindol-6-yloxy)-7-(3-(4-methylpiperazin-1-yl)propoxy)quinoline.
$^1$H NMR Spectrum: (DMSOd$_6$) 2.0(m, 2H); 2.15(s, 3H); 2.2–2.6 (m, 10H); 2.4(s, 3H); 4.35(t, 2H); 6.2(s, 1H); 6.48 (d, 1H); 6.85(d, 1H); 7.2(s, 1H); 7.5(d, 1H); 7.6(s, 1H); 8.7(d, 1H); 8.8(s, 1H)
c) 4-Chloro-6-cyano-7-(3-(4-methylpiperazin-1-yl)propoxy)quinoline was reacted with 1,2-dimethyl-5-hydroxyindole (84 mg), (Tetrahedron 1994, 50, 13433), to give 6-cyano-4-(1,2-dimethylindol-5-yloxy)-7-(3-(4-methylpiperazin-1-yl)propoxy)quinoline.
$^1$H NMR Spectrum: (DMSOd$_6$) 2.0(m, 2H); 2.15(s, 3H); 2.45(s, 3H); 2.2–2.6(m, 10H); 3.71(s, 3H); 4.35(t, 2H); 6.28(s, 1H); 6.4(d, 1H); 6.98(d, 1H); 7.33(s, 1H); 7.52(d, 1H); 7.58(s, 1H); 8.66(d, 1H); 8.79(s, 1H)
d 4-Chloro-6-cyano-7-(3-(4-methylpiperazin-1-yl)propoxy)quinoline was reacted with 6-fluoro-5-hydroxy indole (79 mg), (prepared as described for the preparation of the starting material in Example 25). The product was purified as described in Example 25 to give 6-cyano-4-(6-fluoroindol-5-yloxy)-7-(3-(4-methylpiperazin-1-yl)propoxy)quinoline.
$^1$H NMR Spectrum: (DMSOd$_6$) 2.0(m, 2H); 2.15(s, 3H); 2.2–2.6 (m, 10H); 4.35(t, 2H); 6.5(d, 1H); 6.52(s, 1H); 7.5(m, 2H); 7.62(s, 1H); 7.65 (d, 1H); 8.72(d, 1H); 8.85(s, 1H)
e) 4-Chloro-6-cyano-7-(3-(4-methylpiperazin-1-yl)propoxy)quinoline was reacted with 5-hydroxyindole (70 mg) and the product was purified as described in Example 25 to give 6-cyano-4-(indol-5-yloxy)-7-(3-(4-methylpiperazin-1-yl)propoxy)quinoline.
$^1$H NMR Spectrum: (DMSOd$_6$) 2.0(m, 2H); 2.15(s, 3H); 2.2–2.6(m, 10H); 4.35(t, 2H); 6.45(d, 1H); 6.5(s, 1H); 7.0(dd, 1H); 7.5(m, 2H); 7.55(d, 1H); 7.6(s, 1H); 8.7(d, 1H); 8.8(s, 1H)

EXAMPLE 33

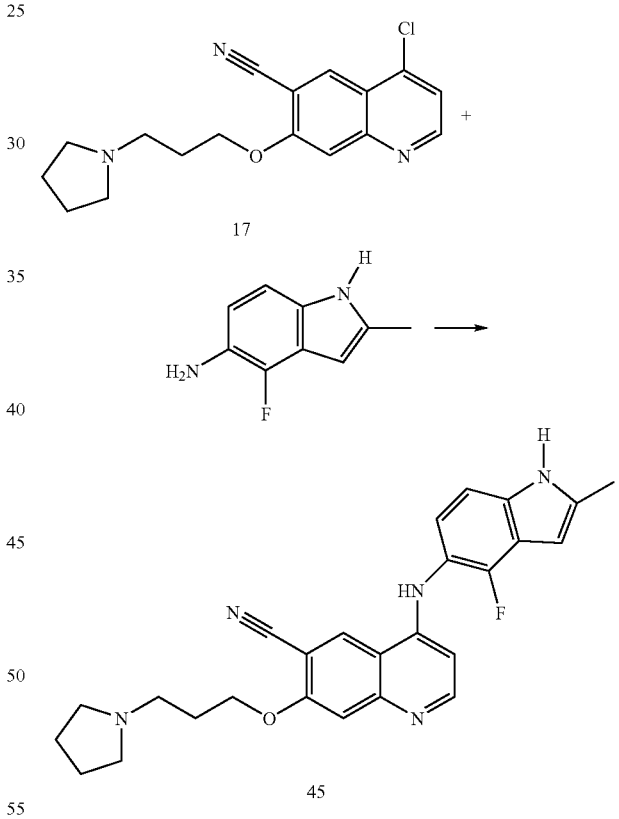

A suspension of 4-chloro-6-cyano-7-(3-(pyrrolidin-1-yl)propoxy))quinoline (100 mg, 0.31 mmol), (prepared as described for the starting material in Example 11), and 5-amino-4-fluoro-2-methylindole (57 mg, 0.35 mmol) in 2-pentanol (4 ml) containing 2N HCl in isopropanol (58 μl) was heated at 120° C. for 1.5 hours. After cooling, the solid was filtered, washed with ether and dried under vacuum to give 6-cyano-4-(4-fluoro-2-methylindol-5-ylamino)-7-(3-(pyrrolidin-1-yl)propoxy)quinoline hydrochloride (118 mg, 72%).

¹H NMR Spectrum: (DMSOd₆) 1.9–2.1 (m, 4H); 2.35 (m, 2H); 2.45 (s, 3H); 3.05 (m, 2H); 3.6 (m, 3); 4.45 (t, 2H); 6.35 (s, 1H); 6.4 (d, 1H); 7.01 (dd, 1H); 7.3 (d, 1H); 7.65 (s, 1H); 8.45 (d, 1H); 9.42 (s, 1H)

MS-ESI: 444 [MH]⁺

The starting material was prepared as follows:

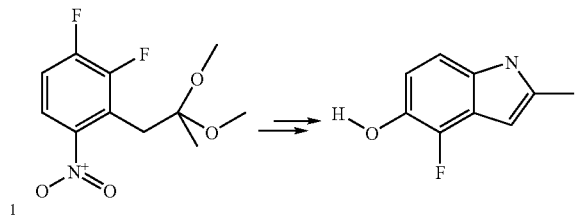

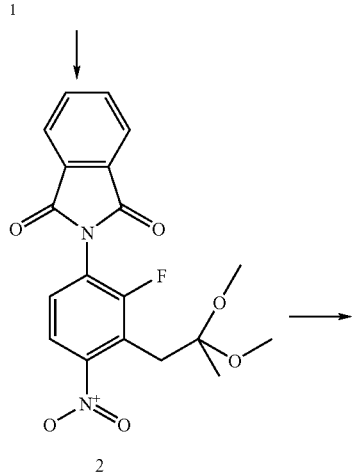

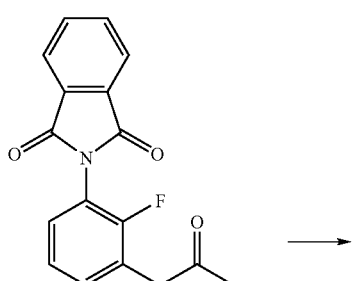

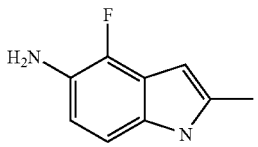

To a solution of phthalimide (4.4 g; 30 mmol) in anhydrous DMF (40 ml) cooled to 0° C. was added sodium hydride (1.29 g, 32 mmol, 60% in oil). The mixture was stirred at this temperature for 30 minutes before the addition of 1,2-difluoro-3-(2,2-dimethoxypropyl)-4-nitrobenzene (6 g, 23 mmol), (prepared as described for the starting material in Example 11). The reaction mixture was heated at 100° C. for 3 hours under argon. Upon cooling to ambient temperature, the reaction mixture was poured over ice/water (200 ml) and the formed precipitate was collected by filtration and washed with water and ether. The solid was purified by flash chromatography using methylene chloride/methanol (99/1). Evaporation of the solvent gave 2-(2,2-dimethoxypropyl)-3-fluoro-4-phthalimidonitrobenzene (5.6 g, 63%) as a yellow solid.

¹H NMR Spectrum: (CDCl₃) 1.25 (s, 3H); 3.15 (s, 6H); 3.50 (s, 2H); 7.40 (dd, 1H); 7.70 (dd, 1H); 7.85 (dd, 2H); 8.0 (dd, 1H)

2-(2,2-Dimethoxypropyl)-3-fluoro-4-phthalimidonitrobenzene (5.5 g, 14 mmol) was suspended in a mixture of THF (200 ml) and methanol (100 ml). HCl 2N (1 ml) was added and the mixture was stirred at ambient temperature for 30 minutes. The solvents were evaporated off and the residue redissolved in methylene chloride, dried (MgSO₄), filtered and the solvent evaporated off. The residue was triturated in pentane and collected by filtration to give 2-(acetylmethyl)-3-fluoro-4-phthalimidonitrobenzene (4.8 g, 100%) as a pale yellow solid.

¹H NMR Spectrum: (CDCl₃) 2.35 (s, 3H); 4.25 (s, 2H); 7.55 (dd, 1H); 7.85 (dd, 2H); 8.0 (dd, 2H); 8.05 (dd, 1H)

2-(Acetylmethyl)-3-fluoro-4-phthalimidonitrobenzene (4.7 g, 14 mmol) was dissolved in acetone (80 ml). Ammonium acetate (210 ml of a freshly prepared 4M aqueous solution) was added followed by titanium trichloride (140 ml, 140 mmol, 15% aqueous solution). The mixture was stirred vigorously for 30 minutes then extracted with ethyl acetate. The organic phase was washed with a hydrogen carbonate solution, brine, dried (MgSO₄), filtered and the solvent evaporated off. The residue was purified by flash chromatography using 0.5% methanol in methylene chloride. Evaporation of the solvent gave 4-fluoro-2-methyl-5-phthalimidoindole (1.27 g; 31%).

¹H NMR Spectrum: DMSOd₆ 2.45 (s, 3H); 6.35 (s, 1H); 7.05 (t, 1H); 7.25 (d, 1H); 8.0 (m, 4H); 11.5 (br s, 1H)

4-Fluoro-2-methyl-5-phthalimidoindole (1.2, 4 mmol) was dissolved in methanol (30 ml). Hydrazine monohydrate (260 µl, 5.3 mmol) was added and the reaction mixture was stirred at ambient temperature for 2 hours. The solvent was evaporated off and the residue taken up in methylene chloride. The phthalhydrazide by-product was removed by filtration and the filtrate purified by flash chromatography 0.5% methanol in methylene chloride. Evaporation of the solvent gave a white solid which contained traces of phthalhydrazide. Further purification was done by dissolving it in ethyl acetate, washing the organic phase with NaOH 2N and brine, drying over MgSO₄. Rotary evaporation of the solvent gave 5-amino-4-fluoro-2-methylindole (500 mg, 76%).

¹H NMR Spectrum: (DMSOd₆) 2.35 (s, 3H); 4.30 (s, 2H); 5.95 (s, 1H); 6.55 (t, 1H); 6.85 (d, 1H); 10.70 (br s, 1H)

MS (ESI): 165 [MH]⁺

EXAMPLE 34

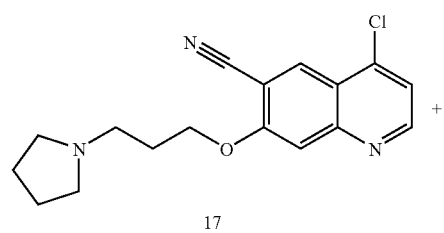

17

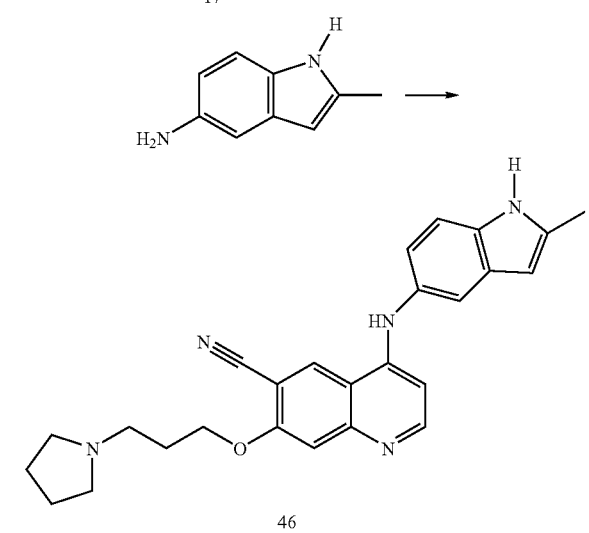

46

Using an analogous procedure to that described in Example 33, 4-chloro-6-cyano-7-(3-(pyrrolidin-1-yl)propoxy)quinoline (100 mg), (prepared as described for the starting material in Example 11), was reacted with 5-amino-2-methylindole (51 mg) to give 6-cyano-4-(2-methylindol-5-ylamino)-7-(3-(pyrrolidin-1-yl)propoxy)quinoline hydrochloride (58 mg, 37%).

¹H NMR Spectrum: (DMSOd₆) 1.85–2.1 (m, 4H); 2.32 (m, 2H); 2.42 (s, 3H); 3.05 (m, 2H); 3.62 (m, 2H); 4.42 (t, 2H); 6.22 (s, 1H); 6.61 (d; 1H); 7.02 (d, 1H); 7.45 (d, 1H); 7.47 (s, 1H); 7.6 (s, 1H); 8.4 (d, 1H); 9.38 (s, 1H)

Mass spectrum: 426 [MH]⁺

EXAMPLE 35

A solution of 4-chloro-6-cyano-7-(3-(pyrrolidin-1-yl)propoxy)quinoline (200 mg, 0.63 mmol), (prepared as described for the starting material in Example 11), potassium carbonate (131 mg, 0.95 mmol) and 3-methyl-5-hydroxyindole (102.5 mg, 0.69 mmol), (Can. J. Chem. 1964, 42, 514), in DMF (6 ml) was stirred at 95° C. for 2 hours. After cooling, silica was added and the volatiles was removed under vacuum. The product was eluted with methylene chloride followed by methylene chloride/ethyl acetate (containing 20% methanol) (9/1 followed by 8/2) followed by methylene chloride/methanol (saturated with ammonia) (9/1 followed by 8/2). The fractions containing the expected product were combined and evaporated. The residue was triturated with ether, filtered and dried under vacuum to give 6-cyano-4-(3-methylindol-5-yloxy)-7-(3-(pyrrolidin-1-yl)propoxy)quinoline (151 mg, 56%).

¹H NMR Spectrum: (DMSOd₆, CF₃COOD) 1.9 (m, 2H); 2.1 (m, 2H); 2.25 (s, 3H); 2.35 (m, 2H); 3.12 (m, 2H); 3.4 (m, 2H); 3.7 (m, 2H); 4.5 (m, 2H); 6.95 (d, 1H); 7.08 (d, 1H); 7.3 (s, 1H); 7.5 (d, 1H); 7.55 (d, 1H); 7.8 (s, 1H); 9.05 (d, 1H); 9.15 (s, 1H)

MS: 427.5 [M+H]+

EXAMPLE 36

The following illustrate representative pharmaceutical dosage forms containing the compound of formula I, or a pharmaceutically acceptable salt thereof (hereafter compound X), for therapeutic or prophylactic use in humans:

| (a) Tablet I | mg/tablet |
|---|---|
| Compound X | 100 |
| Lactose pH.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium staerate | 3.0 |

| (c) Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph.Eur | 488.5 |
| Magnesium stearate | 1.5 |

| (e) Injection I | (50 mg/ml) |
|---|---|
| Compound X | 5.0% w/v |
| 1 N Sodium hydroxide solution | 15.0% w/v |
| 0.1 N Hydrochloric acid (to adjust pH to 7.6) | |
| Polyethylene glycol 400 | 4.5% w/v |
| Water for injection to 100% | |

| (f) Injection II | 10 mg/ml) |
|---|---|
| Compound X | 1.0% w/v |
| Sodium phosphate BP | 3.6% w/v |
| 0.1 N Sodium hydroxide solution | 15.0% w/v |
| Water for injection to 100% | |

| (g) Injection III | (1 mg/ml, buffered to pH 6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

The above formulations may be obtained by conventional procedures well known in the pharmaceutical art. The tablets (a)–(c) may be enteric coated by conventional means, for example to provide a coating of cellulose acetate phthalate.

REFERENCE EXAMPLE 1

2-methyl-1H-pyrrolo[2,3-b]pyridin-5-ol

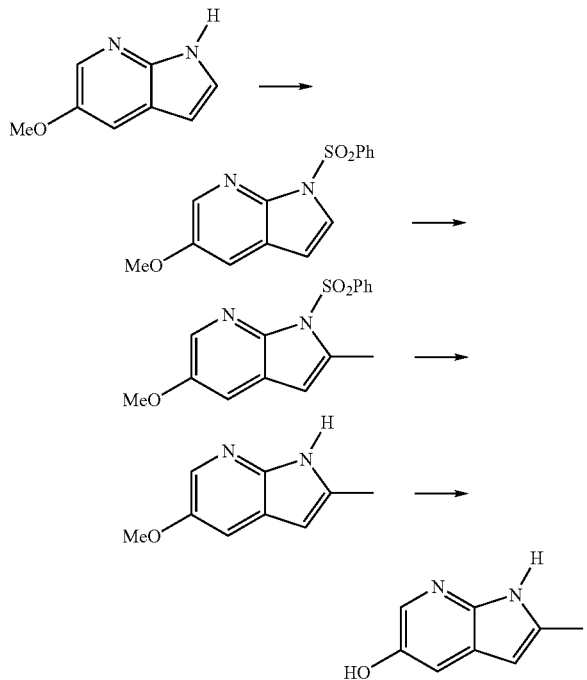

To a solution of 5-methoxy-1H-pyrrolo[2,3-b]pyridine (920 mg, 6.2 mmol) (Heterocycles 50, (2) 1065–1080, 1999) in methylene chloride (20 ml) was added benzyltriethylammonium chloride (37 mg, 0.16 mmol) followed by sodium hydroxide powder (771 mg, 19.2 mmol). The mixture was cooled to 0° C. and benzylsulfonyl chloride (991 µl, 7.77 mmol) was added dropwise. The mixture was stirred at 0° C. for 15 minutes followed by 2 hours at ambient temperature. The mixture was filtered over diatomaceous earth and the filtrate was evaporated under vacuum. The residue was purified by column chromatography eluting with ethyl acetate/petroleum ether (20/80 followed by 30/70). The fractions containing the expected product were combined and evaporated to give 5-methoxy-1-(phenylsulfonyl)-1H-pyrrolo[2,3-b]pyridine (1.69 g; 94%)

$^1$H NMR Spectrum: (DMSO $d_6$) 3.86 (s, 3H); 6.78 (d, 1H); 7.6–7.7 (m, 3H); 7.72 (dd, 1H); 7.88 (d, 1H); 8.02–8.12 (m, 3H)

MS: 289.47 [M+H]+

A solution of 5-methoxy-1-(phenylsulfonyl)-1H-pyrrolo[2,3-b]pyridine (900 mg, 3.12 mmol) in THF (22.5 ml) was added dropwise to a solution of lithium diisopropylamide (prepared from nBu-Li (2.5M in hexane); 2.5 ml) and diisopropylamine (874 µl) in THF (13.5 ml)) cooled at −25° C. and the mixture was stirred for 30 minutes. Methyl iodide (215 µl, 3.44 mmol) in THF (9 ml) was then added dropwise and the mixture was stirred for 10 minutes at −25° C., left to warm up to ambient temperature and stirred for 15 minutes. The mixture was then poured onto ice/water. The mixture was then extracted with ethyl acetate. The organic layer was separated, washed with water, brine, dried (MgSO$_4$), filtered and evaporated. The residue was purified by column chromatography, eluting with ethyl acetate/petroleum ether (20/80 followed by 30/70). The fractions containing the expected product were combined and evaporated to give 5-methoxy-2-methyl-1-(phenylsulfonyl)-1H-pyrrolo[2,3-b]pyridine (805 mg, 85%).

$^1$H NMR Spectrum: (DMSOd$_6$) 2.7 (s, 3H); 3.82 (s, 3H); 6.51 (d, 1H); 7.49 (d, 1H); 7.59 (dd, 2H);7.7 (m, 1H); 8.0–8.1 (m, 3H)

MS: 303.5 [M+H]+

A solution of 5-methoxy-2-methyl-1-(phenylsulfonyl)-1H-pyrrolo[2,3-b]pyridine (950 mg, 3.14 mmol) and 40% aqueous sodium hydroxyde (106 ml) in methanol (160 ml) was heated at reflux for 30 minutes. After cooling, the mixture was poured onto cooled water and extracted with ethyl acetate. The organic layer was separated, washed with water, brine, dried (MgSO$_4$), filtered and evaporated. The residue was purified by column chromatography eluting with ethyl acetate/petroleum ether (1/1). The fractions containing the expected product were combined and evaporated to give 5-methoxy-2-methyl-1H-pyrrolo[2,3-b]pyridine (462 mg, 91%).

$^1$H NMR Spectrum: (DMSO $d_6$) 2.38 (s, 3H); 3.8 (s, 3H); 6.06 (d, 1H); 7.39 (d, 1H); 7.82 (d, 1H)

MS: 163.3 [M+H]+

A solution of boron tribromide (64 µl, 0.68 mmol) in methylene chloride (200 µl) was added to a solution of 5-methoxy-2-methyl-1H-pyrrolo[2,3-b]pyridine (50 mg, 0.308 mmol) in methylene chloride (4 ml) cooled at −30° C. The mixture was left to warm up to ambient temperature and further stirred for 3 hours. The mixture was poured onto ice. The pH was adjusted to 6.2 with 6N aqueous sodium hydroxide followed by 2 N aqueous hydrogen chloride. The mixture was extracted with ethyl acetate. The organic layer was washed with water, followed by brine and dried (MgSO$_4$), filtered and the filtrate was evaporated. The residue was purified by column chromatography, eluting with with methylene chloride followed by methylene chloride/methanol (98/2 followed by 95/5). The fractions containing the expected product were combined and evaporated to give 2-methyl-1H-pyrrolo[2,3-b]pyridin-5-ol (45 mg, quantitative).

$^1$H NMR Spectrum: (DMSO $d_6$) 2.4 (s, 3H); 5.96 (s, 1H); 7.12 (d, 1H); 7.69 (d, 1H); 8.9 (s, 1H); 11.07 (br s, 1H)

MS: 149.2 [M+H]+

What is claimed is:

1. A compound of the formula I:

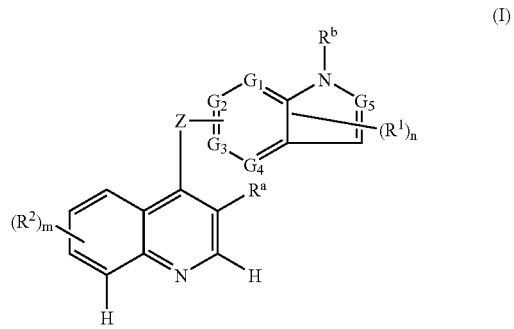

wherein:

$G_1$, $G_2$, $G_3$, $G_4$ and $G_5$ are all —CH— so as to form an indole group;

Z is —O—, —NH—, —S—, —CH$_2$— or a direct bond;
Z is linked to any one of G$_1$, G$_2$, G$_3$ and G$_4$ which is a free carbon atom;
R$^b$ is hydrogen or methyl;
R$^1$ is methyl or fluoro;
n is 0, 1 or 2 such that
the group of formula II:

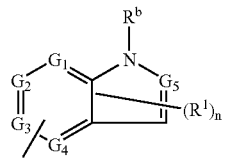

(II)

is a substituted indole selected from:
4-fluoro-2-methylindol-5-yl, 2-methylindol-5-yl, 2-methylindol-6-yl, 2,3-dimethylindol-5-yl, 1-methylindol-5-yl, 1,2-dimethylindol-5-yl, 4-fluoroindol-5-yl, 6-fluoroindol-5-yl and 3-methylindol-5-yl;
m is an integer from 0 to 3;
R$^a$ represents hydrogen or fluoro;
R$^2$ represents hydrogen, hydroxy, halogeno, cyano, nitro, trifluoromethyl, C$_{1-3}$alkyl, C$_{1-3}$alkoxy, C$_{1-3}$alkylsulphanyl, —NR$^3$R$^4$ (wherein R$^3$ and R$^4$, which may be the same or different, each represents hydrogen or C$_{1-3}$alkyl), or R$^5$X$^1$—, wherein X$^1$ represents a direct bond, —O—, —CH$_2$—, —OC(O)—, —C(O)—, —S—, —SO—, —SO$_2$—, —NR$^6$C(O)—, —C(O)NR$^7$—, —SO$_2$NR$^8$—, —NR$^9$SO$_2$— or —NR$^{10}$— (wherein R$^6$, R$^7$, R$^8$, R$^9$ and R$^{10}$ each independently represents hydrogen, C$_{1-3}$alkyl or C$_{1-3}$alkoxyC$_{2-3}$alkyl), and R$^5$ is selected from one of the following twenty-two groups:

1) hydrogen, oxiranylC$_{1-4}$alkyl or C$_{1-5}$alkyl which may be unsubstituted or which may be substituted with one or more groups selected from hydroxy, fluoro, chloro, bromo and amino;

2) C$_{1-5}$alkylX$^2$C(O)R$^{11}$ (wherein X$^2$ represents —O— or —NR$^{12}$— (in which R$^{12}$ represents hydrogen, C$_{1-3}$alkyl or C$_{1-3}$alkoxyC$_{2-3}$alkyl) and R$^{11}$ represents C$_{1-3}$alkyl, —NR$^{13}$R$^{14}$ or —OR$^{15}$ (wherein R$^{13}$, R$^{14}$ and R$^{15}$ which may be the same or different each represents hydrogen, C$_{1-5}$alkyl or C$_{1-3}$alkoxyC$_{2-3}$alkyl));

3) C$_{1-5}$alkylX$^3$R (wherein X$^3$ represents —O—, —S—, —SO—, —SO$_2$—, —OC(O)—, —NR$^{17}$C(O)—, —C(O)NR$^{18}$—, —SO$_2$NR$^{19}$—, —NR$^{20}$SO$_2$— or —NR$^{21}$— (wherein R$^{17}$, R$^{18}$, R$^{19}$, R$^{20}$ and R$^{21}$ each independently represents hydrogen, C$_{1-3}$alkyl or C$_{1-3}$alkoxyC$_{2-3}$alkyl) and R$^{16}$ represents hydrogen, C$_{1-3}$alkyl, cyclopentyl, cyclohexyl or a 4-, 5- or 6-membered saturated heterocyclic group with 1–2 heteroatoms, selected independently from O, S and N, which C$_{1-3}$alkyl group may bear 1 or 2 substituents selected from oxo, hydroxy, halogeno and C$_{1-4}$alkoxy and which cyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkoxyC$_{1-4}$alkyl, C$_{1-4}$alkylsulphonylC$_{1-4}$alkyl, C$_{1-4}$alkoxycarbonyl, C$_{1-4}$aminoalkyl, C$_{1-4}$alkylamino, di(C$_{1-4}$alkyl)amino, C$_{1-4}$alkylaminoC$_{1-4}$alkyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy and a group —(—O—)$_f$(C$_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from C$_{1-4}$alkyl));

4) C$_{1-5}$alkylX$^4$C$_{1-5}$alkylX$^5$R$^{22}$ (wherein X$^4$ and X$^5$ which may be the same or different are each —O—, —S—, —SO—, —SO$_2$—, —NR$^{23}$C(O)—, —C(O)NR$^{24}$—, —SO$_2$NR$^{25}$—, NO$^{26}$SO$_2$— or —NR$^{27}$— (wherein R$^{23}$, R$^{24}$, R$^{25}$, R$^{26}$ and R$^{27}$ each independently represents hydrogen, C$_{1-3}$alkyl or C$_{1-3}$alkoxyC$_{2-3}$alkyl) and R$^{22}$ represents hydrogen, C$_{1-3}$alkyl or C$_{1-3}$alkoxyC$_{2-3}$alkyl);

5) R$^{28}$ (wherein R$^{28}$ is a 4-, 5- or 6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkanoyl, C$_{1-4}$alkoxyC$_{1-4}$alkyl, C$_{1-4}$alkylsulphonyl, C$_{1-4}$alkylsulphonylC$_{1-4}$alkyl, C$_{1-4}$alkoxycarbonyl, C$_{1-4}$aminoalkyl, C$_{1-4}$alkylamino, di(C$_{1-4}$alkyl)amino, C$_{1-4}$alkylaminoC$_{1-4}$alkyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy and a group —(—O—)$_f$(C$_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from C$_{1-4}$alkyl));

6) C$_{1-5}$alkylR$^{28}$ (wherein R$^{28}$ is as defined herein);
7) C$_{2-5}$alkenylR$^{28}$ (wherein R$^{28}$ is as defined herein);
8) C$_{2-5}$alkynylR$^{28}$ (wherein R$^{28}$ is as defined herein);
9) R$^{29}$ (wherein R$^{29}$ represents a pyridone group, a phenyl group or a 5–6-membered aromatic heterocyclic group (linked via carbon or nitrogen) with 1–3 heteroatoms selected from O, N and S, which pyridone, phenyl or aromatic heterocyclic group may carry up to 5 substituents selected from hydroxy, halogeno, amino, C$_{1-4}$alkyl, C$_{1-4}$alkoxy, C$_{1-4}$hydroxyalkyl, C$_{1-4}$aminoalkyl, C$_{1-4}$alkylamino, C$_{1-4}$hydroxyalkoxy, carboxy, trifluoromethyl, cyano, —C(O)NR$^{30}$R$^{31}$, —NR$^{32}$C(O)R$^{33}$ (wherein R$^{30}$, R$^{31}$, R$^{32}$ and R$^{33}$, which may be different, each represents hydrogen, C$_{1-4}$alkyl or C$_{1-3}$alkoxyC$_{2-3}$alkyl) and a group —(—O—)$_f$(C$_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from C$_{1-4}$alkyl));

10) C$_{1-5}$alkylR$^{29}$ (wherein R$^{29}$ is as defined herein);
11) C$_{2-5}$alkenylR$^{29}$ (wherein R$^{29}$ is as defined herein);
12) C$_{2-5}$alkynylR$^{29}$ (wherein R$^{29}$ is as defined herein);
13) C$_{1-5}$alkylX$^6$R$^{29}$ (wherein X$^6$ represents —O—, —S—, —SO—, —SO$_2$—, —NR$^{34}$C(O)—, —C(O)NR$^{35}$—, —SO$_2$NR$^{36}$—, —NR$^{37}$SO$_2$— or —NR$^{38}$— (wherein R$^{34}$, R$^{35}$, R$^{36}$, R$^{37}$ and R$^{38}$ each independently represents hydrogen, C$_{1-3}$alkyl or C$_{1-3}$alkoxyC$_{2-3}$alkyl) and R$^{29}$ is as defined herein);
14) C$_{2-5}$alkenylX$^7$R$^{29}$ (wherein X$^7$ represents —O—, —S—, —SO—, —SO$_2$—, —NR$^{39}$C(O)—, —C(O)NR$^{40}$—, —SO$_2$NR$^{41}$—, —NR$^{42}$SO$_2$— or —NR — (wherein R$^{39}$, R$^{40}$, R$^{41}$, R$^{42}$ and R$^{43}$ each independently represents hydrogen, $C_{1-3}$alkyl or $C_{1-3}$alkoxy$C_{2-3}$alkyl) and $R^{29}$ is as defined herein);

15) $C_{2-5}$alkynyl$X^8R^{29}$ (wherein $X^8$ represents —O—, —S—, —SO—, —SO$_2$—, —NR$^{44}$C(O)—, —C(O)NR$^{45}$—, —SO$_2$NR$^{46}$—, —NR$^{47}$SO$_2$— or —NR$^{48}$— (wherein $R^{44}$, $R^{45}$, $R^{46}$, $R^{47}$ and $R^{48}$ each independently represents hydrogen, $C_{1-3}$alkyl or $C_{1-3}$alkoxy$C_{2-3}$alkyl) and $R^{29}$ is as defined herein);

16) $C_{1-4}$alkyl$X^9C_{1-4}$alkyl$R^{29}$ (wherein $X^9$ represents —O—, —S—, —SO—, —SO$_2$—, —NR$^{49}$C(O)—, —C(O)NR$^{50}$—, —SO$_2$NR$^{51}$—, —NR$^{52}$SO$_2$— or —NR$^{53}$— (wherein $R^{49}$, $R^{50}$, $R^{51}$, $R^{52}$ and $R^{53}$ each independently represents hydrogen, $C_{1-3}$alkyl or $C_{1-3}$alkoxy$C_{2-3}$alkyl) and $R^{29}$ is as defined herein);

17) $C_{1-4}$alkyl$X^9C_{1-4}$alkyl$R^{28}$ (wherein $X^9$ and $R^{28}$ are as defined herein);

18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

20) $C_{2-5}$alkenyl$X^9C_{1-4}$alkyl$R^{28}$ (wherein $X^9$ and $R^{28}$ are as defined herein);

21) $C_{2-5}$alkynyl$X^9C_{1-4}$alkyl$R^{28}$ (wherein $X^9$ and $R^{28}$ are as defined herein); and 22) $C_{1-4}$alkyl$R^{54}(C_{1-4}$alkyl$)_q(X^9)_rR^{55}$ (wherein $X^9$ is as defined herein, q is 0 or 1, r is 0 or 1, and $R^{54}$ and $R^{55}$ are each independently selected from hydrogen, $C_{1-3}$alkyl, cyclopentyl, cyclohexyl and a 4-, 5- or 6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 4-, 5- or 6-membered saturated heterocyclic group with 1–2 heteroatoms, selected independently from O, S and N, which cyclic group may bear one or more substituents selected from $C_{1-4}$alkyl), with the proviso that $R^{54}$ cannot be hydrogen);

and additionally wherein any $C_{1-5}$alkyl, $C_{2-5}$alkenyl or $C_{2-5}$alkynyl group in $R^5X^1$— may bear one or more substituents selected from hydroxy, halogeno and amino;

with the proviso that $R^2$ at the 7-position of the quinoline ring cannot have any value selected from hydrogen, methyl, methoxy and chloro;

or a salt thereof.

2. A compound of the formula I according to claim 1 wherein Z is —O—, —NH— or —S—.

3. A compound according to claim 1 wherein $R^2$ represents hydroxy, halogeno, nitro, trifluoromethyl, $C_{1-3}$alkyl, cyano, amino or $R^5X^1$—, wherein $X^1$ is as defined in claim 1 and $R^5$ is selected from one of the following twenty groups:

1) $C_{1-3}$alkyl which may be unsubstituted or which may be substituted with one or more groups selected from fluoro, chloro and bromo, or $C_{2-3}$alkyl which may be unsubstituted or substituted with one or more groups selected from hydroxy and amino;

2) 2-(3,3-dimethylureido)ethyl, 3-(3,3-dimethylureido)propyl, 2-(3-methylureido)ethyl, 3-(3-methylureido)propyl, 2-ureidoethyl, 3-ureidopropyl, 2-(N,N-dimethylcarbamoyloxy)ethyl, 3-(N,N-dimethylcarbamoyloxy)propyl, 2-(N-methylcarbamoyloxy)ethyl, 3-(N-methylcarbamoyloxy)propyl, 2-(carbamoyloxy)ethyl, 3-(carbamoyloxy)propyl, or 2-(N-methyl-N-(butoxycarbonyl)amino)ethyl;

3) $C_{2-3}$alkyl$X^3R^{16}$ (wherein $X^3$ is as defined in claim 1 and $R^{16}$ is a group selected from $C_{1-3}$alkyl, cyclopentyl, cyclohexyl, pyrrolidinyl, piperidinyl, piperazinyl, azetidinyl, imidazolidinyl and tetrahydropyranyl which group is linked to $X^3$ through a carbon atom and which $C_{1-3}$alkyl group may bear 1 or 2 substituents selected from hydroxy, halogeno and $C_{1-2}$alkoxy and which cyclopentyl, cyclohexyl, pyrrolidinyl, piperidinyl, piperazinyl, azetidinyl, imidazolidinyl or tetrahydropyranyl group may bear one substituent selected from oxo, hydroxy, halogeno, cyano, $C_{1-2}$cyanoalkyl, $C_{1-2}$alkyl, $C_{1-2}$hydroxyalkyl, $C_{1-2}$alkoxy, $C_{1-2}$alkoxy$C_{1-3}$alkyl, $C_{1-2}$alkylsulphonyl$C_{1-3}$alkyl, $C_{1-2}$alkoxycarbonyl, $C_{1-3}$alkylamino, di($C_{1-3}$alkyl)amino, $C_{1-3}$allcylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino));

4) $C_{2-3}$alkyl$X^4C_{2-3}$alkyl$X^5R^{22}$ (wherein $X^4$ and $X^5$ are as defined in claim 1 and $R^{22}$ represents hydrogen or $C_{1-2}$alkyl);

5) $R^{28}$ (wherein R is as defined in claim 1);

6) $C_{1-3}$alkyl$R^{59}$ (wherein $R^{59}$ is a group selected from pyrrolidinyl, piperazinyl, piperidinyl, azetidinyl, imidazolidinyl, 1,3-dioxolan-2-yl, 1,3-dioxan-2-yl, 1,3-dithiolan-2-yl and 1,3-dithian-2-yl, which group is linked to $C_{1-3}$alkyl through a carbon atom and which group may bear 1 or 2 substituents selected from oxo, hydroxy, halogeno, cyano, $C_{1-2}$cyanoalkyl, $C_{1-2}$alkyl, $C_{1-2}$hydroxyalkyl, $C_{1-2}$alkoxy, $C_{1-2}$alkanoyl, $C_{1-2}$alkoxy$C_{1-3}$alkyl, $C_{1-2}$alkylsulphonyl, $C_{1-2}$alkylsulphonyl$C_{1-3}$alkyl, $C_{1-2}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino)) or $C_{2-3}$alkyl$R^{60}$ (wherein $R^{60}$ is a group selected from morpholino, thiomorpholino, azetidin-1-yl, pyrrolidin-1-yl, piperazin-1-yl and piperidino which group may bear 1 or 2 substituents selected from oxo, hydroxy, halogeno, cyano, $C_{1-2}$cyanoalkyl, $C_{1-2}$alkyl, $C_{1-2}$hydroxyalkyl, C$_{1-2}$alkoxy, C$_{1-2}$alkanoyl, C$_{1-2}$alkoxyC$_{1-3}$alkyl, C$_{1-2}$alkylsulphonyl, C$_{1-2}$alkylsulphonylC$_{1-3}$alkyl, C$_{1-2}$alkoxycarbonyl, C$_{1-3}$alkylamino, di(C$_{1-3}$alkyl)amino, C$_{1-3}$alkylaminoC$_{1-3}$alkyl, di(C$_{1-3}$alkyl)aminoC$_{1-3}$alkyl, C$_{1-3}$alkylaminoC$_{1-3}$alkoxy, di(C$_{1-3}$alkyl)aminoC$_{1-3}$alkoxy and a group —(—O—)$_f$(C$_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino));

7) R$^{29}$ (wherein R$^{29}$ is as defined in claim 1);
8) C$_{1-4}$alkylR$^{29}$ (wherein R$^{29}$ is as defined in claim 1);
9) 1-R$^{29}$but-2-en-4-yl (wherein R$^{29}$ is as defined in claim 1);
10) 1-R$^{29}$but-2-yn-4-yl (wherein R$^{29}$ is as defined in claim 1);
11) C$_{1-3}$alkylX$^6$R$^{29}$ (wherein X$^6$ and R$^{29}$ are as defined in claim 1);
12) 1-(R$^{29}$X$^7$)but-2-en-4-yl (wherein X$^7$ and R$^{29}$ are as defined in claim 1);
13) 1-(R$^{29}$X$^8$)but-2-yn-4-yl (wherein X$^8$ and R$^{29}$ are as defined in claim 1);
14) C$_{2-3}$alkylX$^9$C$_{1-3}$alkylR$^{29}$ (wherein X$^9$ and R$^{29}$ are as defined in claim 1);
15) C$_{2-3}$alkylX$^9$C$_{1-3}$alkylR$^{28}$ (wherein X$^9$ and R$^{28}$ are as defined in claim 1);
16) C$_{2-5}$alkenyl which may be unsubstituted or which may be substituted with one or more fluorine atoms or with one or two groups selected from hydroxy, fluoro, amino, C$_{1-4}$alkylamino, N,N-di(C$_{1-4}$alkyl)amino, aminosulphonyl, N—C$_{1-4}$alkylaminosulphonyl and N,N-di(C$_{1-4}$alkyl)aminosulphonyl;
17) C$_{2-5}$alkynyl which may be unsubstituted or which may be substituted with one or more fluorine atoms or with one or two groups selected from hydroxy, fluoro, amino, C$_{1-4}$alkylamino N,N-di(C$_{1-4}$alkyl)amino, aminosulphonyl, N—C$_{1-4}$alkylaminosulphonyl and N,N-di(C$_{1-4}$alkyl)aminosulphonyl;
18) C$_{2-3}$alkenylX$^9$C$_{1-3}$alkylR$^{28}$ (wherein X$^9$ and R$^{28}$ are as defined in claim 1);
19) C$_{2-3}$alkynylX$^9$C$_{1-3}$alkylR$^{28}$ (wherein X$^9$ and R$^{28}$ are as defined in claim 1); and
20) C$_{1-3}$alkylR$^{54}$(C$_{1-3}$alkyl)$_q$(X$^9$)$_r$R$^{55}$ (wherein X$^9$, q, r, R$^{54}$ and R$^{55}$ are as defined in claim 1);
and additionally wherein any C$_{1-5}$alkyl, C$_{2-5}$alkenyl or C$_{2-5}$alkynyl group in R$^5$X$^1$— may bear one or more substituents selected from hydroxy, halogeno and amino.

4. A compound according to claim 1 wherein one of the R$^2$ substituents is R$^5$X$^1$—, wherein R$^5$ and X$^1$ are as defined in claim 1, and the substituent R$^5$X$^1$— is at the 7-position of the quinoline ring.

5. A compound according to claim 3 wherein one of the R$^2$ substituents is R$^5$X$^1$—, wherein R$^5$ and X$^1$ are as defined in claim 3, and the substituent R$^5$X$^1$— is at the 7-position of the quinoline ring.

6. A compound according to claim 4 wherein the R$^2$ substituent at the 6-position of the quinoline ring is hydrogen, methoxy or cyano.

7. A compound selected from:
6-cyano-4-(2-methylindol-5-ylamino)-7-(2-(1,2,3-triazol-1-yl)ethoxy)quinoline,
6-cyano-4-(2-methylindol-5-yloxy)-7-(3-(4-methylpiperazin-1-yl)propoxy)quinoline,
6-cyano-4-(4-fluoro-2-methylindol-5-yloxy)-7-(3-(pyrrolidin-1-yl)propoxy)quinoline,
6-cyano-4-(4-fluoro-2-methylindol-5-yloxy)-7-(3-(4-methylpiperazin-1-yl)propoxy)-quinoline,
6-cyano-4-(2-methylindol-5-yloxy)-7-(3-(pyrrolidin-1-yl)propoxy)quinoline,
6-cyano-4-(2,3-dimethylindol-5-yloxy)-7-(3-(pyrrolidin-1-yl)propoxy)quinoline,
6-cyano-4-(1,2-dimethylindol-5-yloxy)-7-(3-(pyrrolidin-1-yl)propoxy)quinoline,
6-cyano-4-(2,3-dimethylindol-5-yloxy)-7-(3-(4-methylpiperazin-1-yl)propoxy)quinoline,
6-cyano-4-(1,2-dimethylindol-5-yloxy)-7-(3-(4-methylpiperazin-1-yl)propoxy)quinoline,
6-cyano-4-(4-fluoroindol-5-yloxy)-7-(3-(pyrrolidin-1-yl)propoxy)quinoline,
6-cyano-4-(6-fluoroindol-5-yloxy)-7-(3-(pyrrolidin-1-yl)propoxy)quinoline,
6-cyano-4-(6-fluoroindol-5-yloxy)-7-(3-(4-methylpiperazin-1-yl)propoxy)quinoline,
6-cyano-4-(4-fluoro-2-methylindol-5-ylamino)-7-(3-(pyrrolidin-1-yl)propoxy)quinoline,
6-cyano-4-(2-methylindol-5-ylamino)-7-(3-(pyrrolidin-1-yl)propoxy)quinoline, and
6-cyano-4-(3-methylindol-5-yloxy)-7-(3-(pyrrolidin-1-yl)propoxy)quinoline,
or a salt thereof.

8. A compound selected from:
6-cyano-4-(2-methylindol-6-yloxy)-7-(3-(4-methylpiperazin-1-yl)propoxy)quinoline,
6-cyano-4-(2-methylindol-6-yloxy)-7-(3-(pyrrolidin-1-yl)propoxy)quinoline,
6-cyano-4-(2,3-dimethylindol-5-ylamino)-7-(2-(1,2,3-triazol-1-yl)ethoxy)quinoline,
6-cyano-7-(3-(1,1-dioxothiomorpholino)propoxy-4-(2-methylindol-5-ylamino)quinoline,
6-cyano-4-(2,3-dimethylindol-5-ylamino)-7-(3-(1,1-dioxothiomorpholino)propoxy)-quinoline,
6-cyano-4-(2,3-dimethylindol-5-yloxy)-7-(3-(1,1-dioxothiomorpholino)propoxy)-quinoline,
6-cyano-7-(3-(1,1-dioxothiomorpholino)propoxy-4-(2-methylindol-5-yloxy)quinoline,
6-cyano-4-(4-fluoro-2-methylindol-5-yloxy)-7-(2-methoxyethoxy)quinoline,
6-cyano-4-(4-fluoro-2-methylindol-5-yloxy)-7-(2-(1,2,3-triazol-1-yl)ethoxy)quinoline,
6-cyano-4-(4-fluoro-2-methylindol-5-yloxy)-7-(3-(1,2,3-triazol-1-yl)propoxy)quinoline, and
6-cyano-4-(4-fluoro-2-methylindol-5-yloxy)-7-(3-(1,1-dioxothiomorpholino)propoxy)-quinohne,
or a salt thereof.

9. A process for the preparation of a compound as claimed in claim 1 or a salt thereof which comprises:
(a) the reaction of a compound of the formula III:

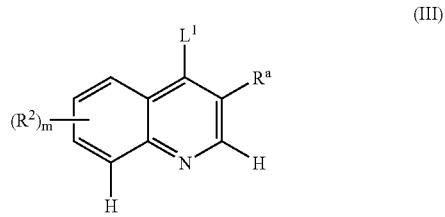

(III)

(wherein R$^a$, R$^2$ and m are as defined in claim 1 and L$^1$ is a displaceable moiety), with a compound of the formula IV:

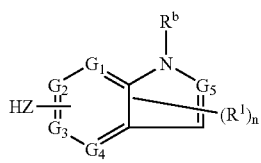

(wherein the substituted indole group and Z are as defined in claim 1);

(b) a compound of formula I or a salt thereof wherein at least one $R^2$ is $R^5X^1$ wherein $R^5$ is as defined in claim 1 and $X^1$ is —O—, —S—, —OC(O)— or —NR$^{10}$— (wherein $R^{10}$ independently represents hydrogen, $C_{1-3}$alkyl or $C_{1-3}$alkoxy$C_{2-3}$alkyl) may be prepared by the reaction of a compound of the formula V:

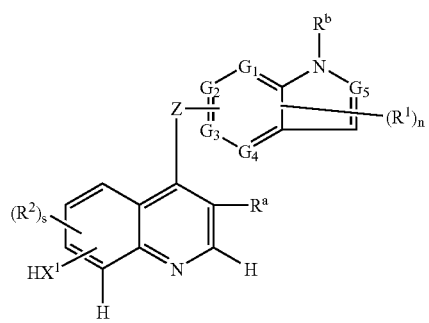

(wherein $R^a$, Z, the substituted indole group and $R^2$ are as defined in claim 1 and $X^1$ is as herein defined in this section and s is an integer from 0 to 2) with a compound of formula VI:

$$R^5\text{—}L^1 \quad (VI)$$

(wherein $R^5$ is as defined in claim 1 and $L^1$ is as defined herein);

(c) a compound of formula I or a salt thereof wherein at least one $R^2$ is $R^5X^1$ wherein $R^5$ is as defined in claim 1 and $X^1$ is —O—, —S—, —OC(O)— or —NR$^{10}$— (wherein $R^{10}$ represents hydrogen, $C_{1-3}$alkyl or $C_{1-3}$alkoxy$C_{2-3}$alkyl) may be prepared by the reaction of a compound of the formula VII:

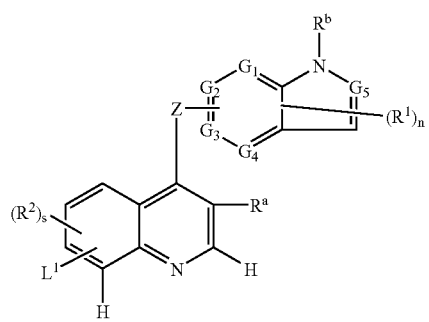

with a compound of the formula VIII:

$$R^5\text{—}X^1\text{—}H \quad (VIII)$$

(wherein $R^a$, $R^2$, $R^5$, the substituted indole group and Z are all as defined in claim 1, $L^1$ and s are as defined herein and $X^1$ is as herein defined in this section);

(d) a compound of formula I or a salt thereof wherein at least one $R^2$ is $R^5X^1$ wherein $X^1$ is as defined in claim 1 and $R^5$ is $C_{1-5}$alkyl$R^{62}$, wherein $R^{62}$ is selected from one of the following nine groups:

1) $X^{10}C_{1-3}$alkyl (wherein $X^{10}$ represents —O—, —S—, —SO$_2$—, —NR$^{63}$C(O)— or —NR$^{64}$SO$_2$— (wherein $R^{63}$ and $R^{64}$ which may be the same or different are each hydrogen, $C_{1-3}$alkyl or $C_{1-3}$alkoxy$C_{2-3}$alkyl);

2) NR$^{65}$R$^{66}$ (wherein $R^{65}$ and $R^{66}$ which may be the same or different are each hydrogen, $C_{1-3}$alkyl or $C_{1-3}$alkoxy$C_{2-3}$alkyl);

3) $X^{11}C_{1-5}$alkyl$X^5R^{22}$ (wherein $X^{11}$ represents —O—, —S—, —SO$_2$—, —NR$^{67}$C(O)—, —NR$^{68}$SO$_2$— or —NR$^{69}$— (wherein $R^{67}$, $R^{68}$, and $R^{69}$ which may be the same or different are each hydrogen, $C_{1-3}$alkyl or $C_{1-3}$alkoxy$C_{2-3}$alkyl) and $X^5$ and $R^{22}$ are as defined in claim 1);

4) $R^{28}$ (wherein $R^{28}$ is as defined in claim 1);

5) $X^{12}R^{29}$ (wherein $X^{12}$ represents —O—, —S—, —SO$_2$—, —NR$^{70}$C(O)—, —NR$^{71}$SO$_2$—, or —NR$^{72}$— (wherein $R^{70}$, $R^{71}$, and $R^{72}$ which may be the same or different are each hydrogen, $C_{1-3}$alkyl or $C_{1-3}$alkoxy$C_{2-3}$alkyl) and $R^{29}$ is as defined in claim 1); and 6) $X^{13}C_{1-3}$alkyl$R^{29}$ (wherein $X^{13}$ represents —O—, —S—, —SO$_2$—, —NR$^{73}$C(O)—, —NR$^{74}$SO$_2$— or —NR$^{75}$— (wherein $R^{73}$, $R^{74}$ and $R^{75}$ each independently represents hydrogen, $C_{1-3}$alkyl or $C_{1-3}$alkoxy$C_{2-3}$alkyl) and $R^{29}$ is as defined in claim 1);

7) $R^{29}$ (wherein $R^{29}$ is as defined in claim 1);

8) $X^{13}C_{1-4}$alkyl$R^{28}$ (wherein $X^{13}$ and $R^{28}$ are as defined in claim 1); and 9) $R^{54}(C_{1-4}$alkyl$)_q(X^9)_rR^{55}$ (wherein q, r, $X^9$, $R^{54}$ and $R^{55}$ are as defined in claim 1); may be prepared by reacting a compound of the formula IX:

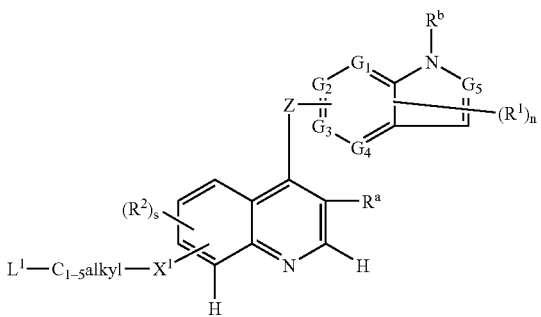

(wherein $X^1$, $R^a$, the substituted indole group $R^2$ and Z and n are as defined in claim 1 and $L^1$ and s are as defined herein) with a compound of the formula X:

$$R^{62}\text{—}H \quad (X)$$

(wherein $R^{62}$ is as defined herein);

(e) a compound of formula I or a salt thereof wherein one or more of the substituents $(R^2)_m$ is represented by —NR$^{76}$R$^{77}$, where one (and the other is hydrogen) or both of $R^{76}$ and $R^{77}$ are $C_{1-3}$alkyl, may be effected by the reaction of compounds of formula I wherein the substituent $(R^2)_m$ is an amino group and an alkylating agent;

(f) a compound of formula I or a salt thereof wherein $X^1$ is —SO— or —SO$_2$— may be prepared by oxidation from the corresponding compound in which $X^1$ is —S— or —SO— (when $X^1$ is —SO$_2$— is required in the final product);

and optionally reacting the compound obtained with an acid or base whereby to obtain a salt of a compound of formula I.

10. A compound according to claim 5, wherein the $R^2$ substituent at the 6-position of the quinoline ring is hydrogen, methoxy or cyano.

11. A compound according to claim 6, wherein the $R^2$ substituent at the 6-position of the quinoline ring is cyano.

12. A compound according to claim 10 wherein the $R^2$ substituent at the 6-position of the quinoline ring is cyano.

13. A compound according to any one of claims 1, 2, 3 to 7, 8 and 10–12 in the form of a pharmaceutically acceptable salt.

14. A pharmaceutical composition which comprises a compound of the formula I as defined in any one of claims 1, 2, 3 to 7, 8 and 10–12 or a pharmaceutically acceptable salt thereof, in association with a pharmaceutically acceptable excipient or carrier.

15. A method for producing an antiangiogenic and/or vascular permeability reducing effect in a warm-blooded animal in need of such treatment which comprises administering to said animal an effective amount of a compound of formula I as defined in any one of claims 1, 2, 3 to 7, 14 and 10–12 or a pharmaceutically acceptable salt thereof.

* * * * *